United States Patent
Meissner et al.

(10) Patent No.: US 12,195,802 B2
(45) Date of Patent: Jan. 14, 2025

(54) UNIVERSAL EARLY CANCER DIAGNOSTICS

(71) Applicants: President and Fellows of Harvard College, Cambridge, MA (US); Dana-Farber Cancer Institute, Inc., Boston, MA (US)

(72) Inventors: Alexander Meissner, Cambridge, MA (US); Zachary D. Smith, Cambridge, MA (US); Franziska Michor, Cambridge, MA (US); Jiantao Shi, Jamaica Plain, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 19 days.

(21) Appl. No.: 16/613,114

(22) PCT Filed: May 14, 2018

(86) PCT No.: PCT/US2018/032612
§ 371 (c)(1),
(2) Date: Nov. 12, 2019

(87) PCT Pub. No.: WO2018/209361
PCT Pub. Date: Nov. 15, 2018

(65) Prior Publication Data
US 2020/0109456 A1    Apr. 9, 2020

Related U.S. Application Data

(60) Provisional application No. 62/560,660, filed on Sep. 19, 2017, provisional application No. 62/511,648, (Continued)

(51) Int. Cl.
   *C12Q 1/6886*    (2018.01)
(52) U.S. Cl.
   CPC ..... *C12Q 1/6886* (2013.01); *C12Q 2600/154* (2013.01)
(58) Field of Classification Search
   None
   See application file for complete search history.

(56) References Cited

U.S. PATENT DOCUMENTS

2012/0202202 A1    8/2012  Wang et al.
2014/0179770 A1*   6/2014  Zhang .................... C12N 15/63
                                                 514/44 R
(Continued)

FOREIGN PATENT DOCUMENTS

EP         3011031 A1    4/2016
WO    WO-2014/043763 A1  3/2014
(Continued)

OTHER PUBLICATIONS

Du et al.Twin Research and Human genetics. 2015. 18(6): 670-679 (Year: 2015).*
(Continued)

*Primary Examiner* — Carla J Myers
(74) *Attorney, Agent, or Firm* — Morse, Barnes-Brown & Pendleton, P.C.; Lisa M. Warren, Esq.; Daniel L. Branson, Esq.

(57) ABSTRACT

Methods for quantifying DNA methylation that may be utilized for screening for diseases (e.g., cancer), diagnosing diseases (e.g., cancer type), monitoring progression of a disease, and monitoring response to a therapeutic treatment.

16 Claims, 45 Drawing Sheets
(42 of 45 Drawing Sheet(s) Filed in Color)
Specification includes a Sequence Listing.

Related U.S. Application Data filed on May 26, 2017, provisional application No. 62/505,647, filed on May 12, 2017.

(56) References Cited

U.S. PATENT DOCUMENTS

| | | |
|---|---|---|
| 2015/0011403 A1 | 1/2015 | Lo et al. |
| 2016/0210403 A1 | 7/2016 | Zhang et al. |
| 2016/0326593 A1 | 11/2016 | Clement et al. |
| 2018/0087105 A1 | 3/2018 | Larson et al. |
| 2018/0237863 A1 | 8/2018 | Namsaraev et al. |
| 2020/0087731 A1 | 3/2020 | Zhang et al. |
| 2020/0109456 A1 | 4/2020 | Meissner et al. |
| 2020/0131582 A1 | 4/2020 | Zhou et al. |

FOREIGN PATENT DOCUMENTS

| | | |
|---|---|---|
| WO | WO-2015/181804 A2 | 12/2015 |
| WO | WO-2017/090724 A1 | 6/2017 |
| WO | WO-2017/181146 A1 | 10/2017 |
| WO | WO-2017/190215 A1 | 11/2017 |
| WO | WO-2017/201606 A1 | 11/2017 |
| WO | WO-2019/200410 A1 | 10/2019 |

OTHER PUBLICATIONS

ThermoFisher Scientific, "Circulating, Cell-Free Tumor DNA Detection with Ion PGM Sequencing." Retrieved from the Internet on Oct. 11, 2018: < URL: https://www.thermofisher.com/blog/behindthebench/circulating-cell-free-tumor-dna-detection-with-ion-pgm-sequencing/ >; pp. 1-3.

Smith, et al., "Epigenetic Restriction of Extraembryonic Lineages Mirrors the Somatic Transition to Cancer," *Nature*, 549(7673:543-547, (Sep. 28, 2017).

Smith, et al., "DNA Methylation: Roles in Mammalian Development," *Nat. Rev. Genet.*, 14(3):204-220, (Mar. 2013).

International Search Report from PCT/US2018/032612, dated Nov. 30, 2018.

Jurkowski, et al., "Synthetic Epigenetics Towards Intelligent Control of Epigenetic States and Cell Identify," *Clinical Epigenetics*, 7(1): p. 18, XP021214618, (Mar. 4, 2015).

Liggett, et al., "Differential Methylation of Cell-Free Circulating DNA Among Patients With Pancreatic Cancer Versus Chronic Pancreatitis," *Cancer*, 116(7) :1674-1680, (Apr. 1, 2010).

Mueller, et al., "Methylated DNA as a Possible Screening Marker for Neoplastic Disease in Several Body Fluids," *Expert Reviews in Molecular Diagnostics*, 3(4):443-458, (Jul. 1, 2003).

Qin, et al., "Cell-Free Circulating Tumor DNA in Cancer," *Chinese Journal of Cancer*, 35(1):XP055618341, (Apr. 7, 2016).

Warton, et al., "Methylated Circulating Tumor DNA in Blood: Power in Cancer Prognosis and Response," *Endocrine-Related Cancer*, 23(3):R157-R171, (Jan. 13, 2016).

International Search Report for PCT/US2021/064210, dated Mar. 8, 2022.

Jahr, et al., "DNA Fragments in the Blood Plasma of Cancer Patients: Quantitations and Evidence for Their Origin from Apoptotic and Necrotic Cells," *Cancer Research, American Association for Cancer Research*, 61(4):1659-1665, (Feb. 15, 2001).

Volik, et al., "Cell-Free DNA (cfDNA): Clinical Significance and Utility in Cancer shaped by Emerging Technologies," *Molecular Cancer Research*, 14(10):898-908, (Jul. 15, 2016).

Lokk, et al., "DNA methylome profiling of human tissues identifies global and tissue specificmethylation patterns," Genome Biology, vol. 15, No. 4, p. R54, 2014.

Loricz, et al., "Evidence for Converging DNA Methylation Pathways in Placenta and Cancer," Developmental Cell, vol. 43, No. 3, pp. 257-258, 2017.

\* cited by examiner

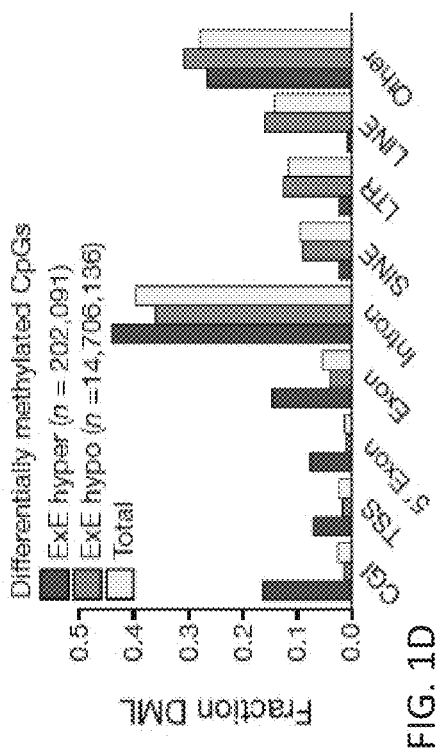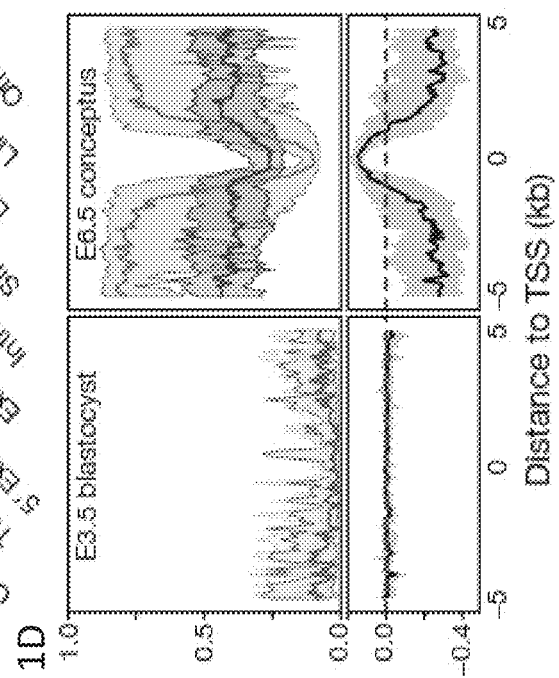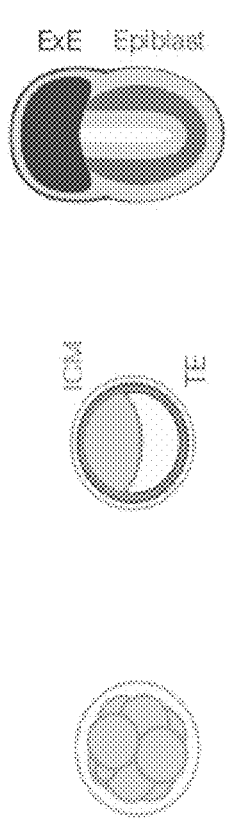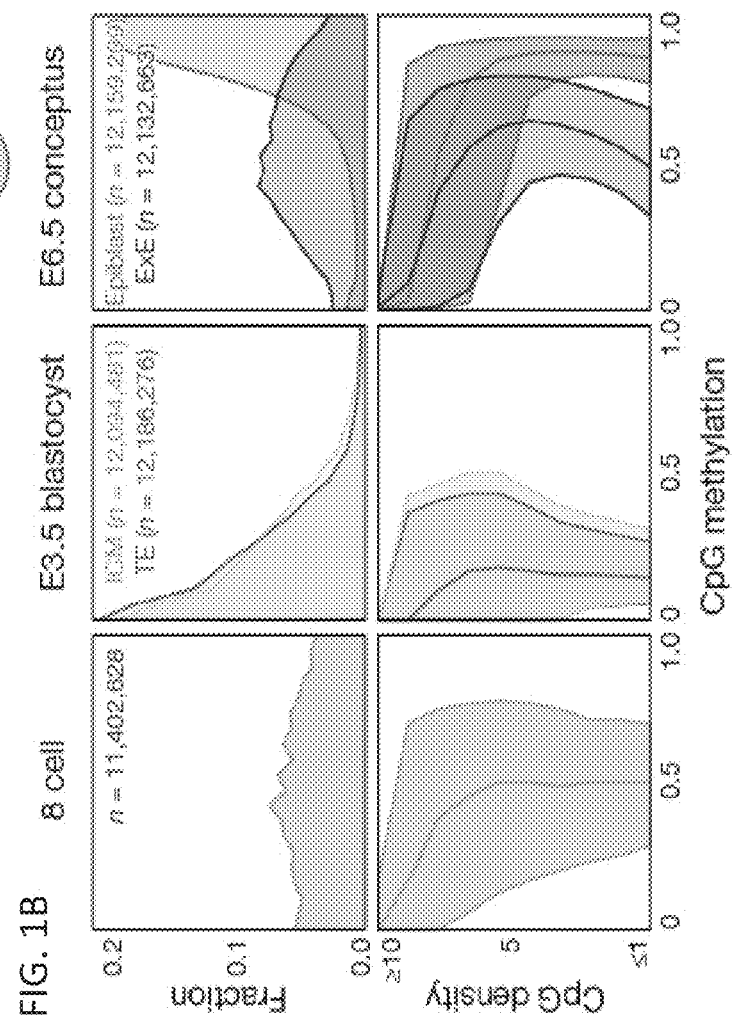
FIG. 1A  FIG. 1B  FIG. 1C  FIG. 1D

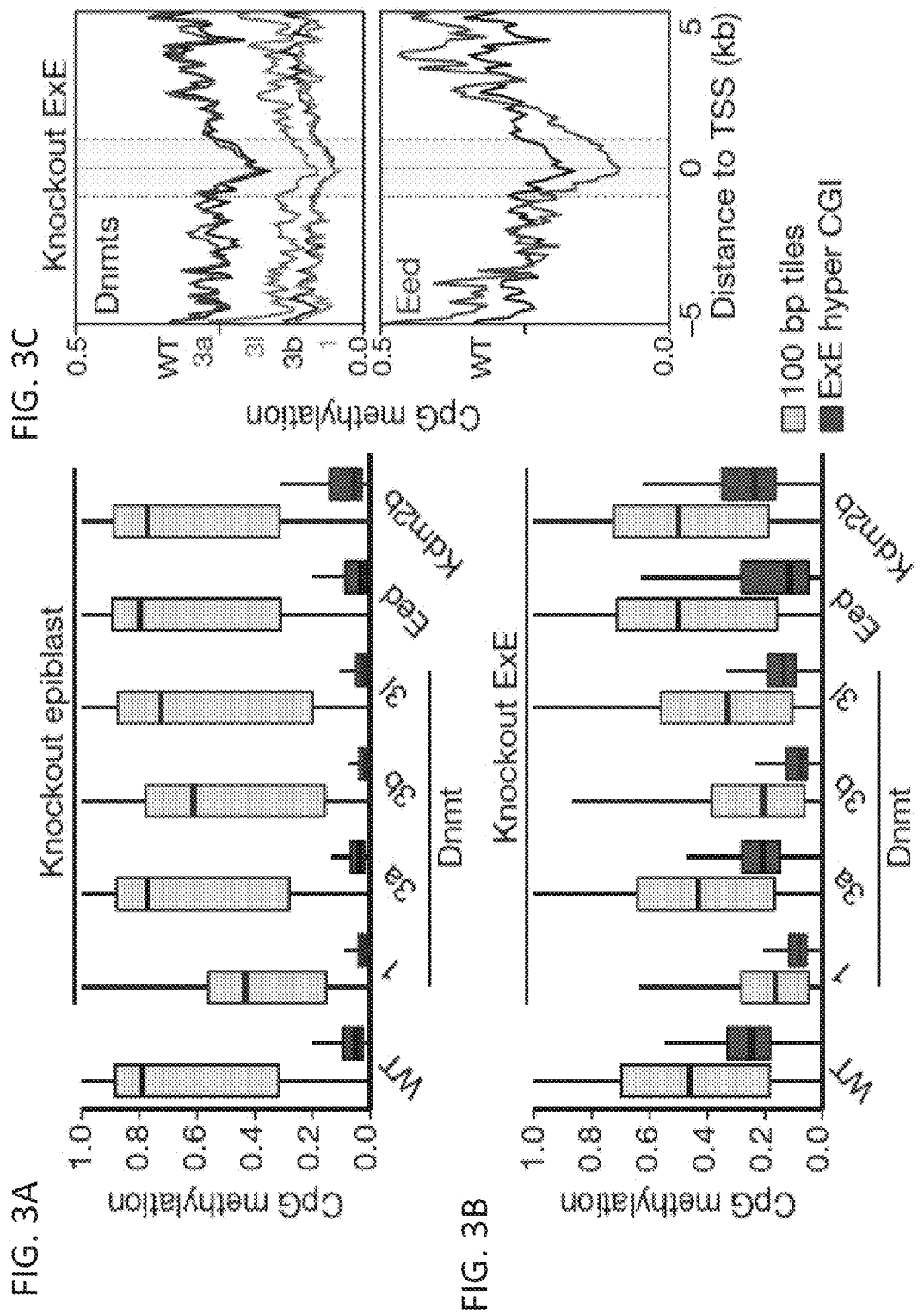

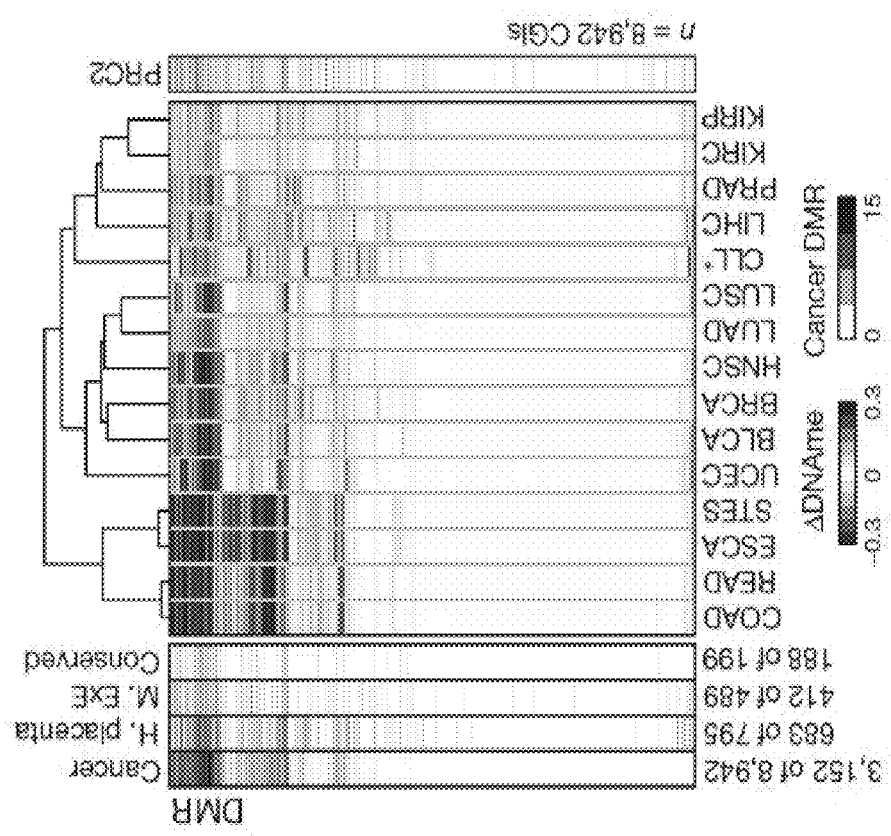
FIG. 4A
FIG. 4B
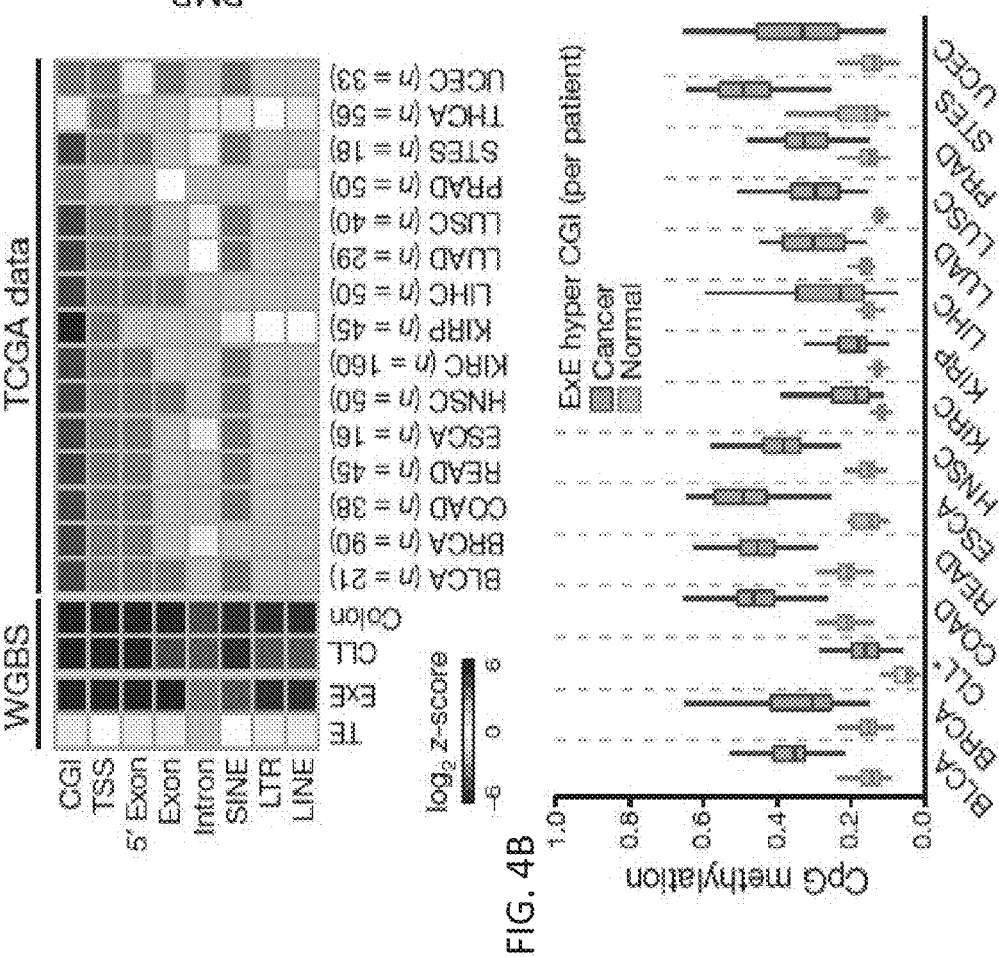
FIG. 4C

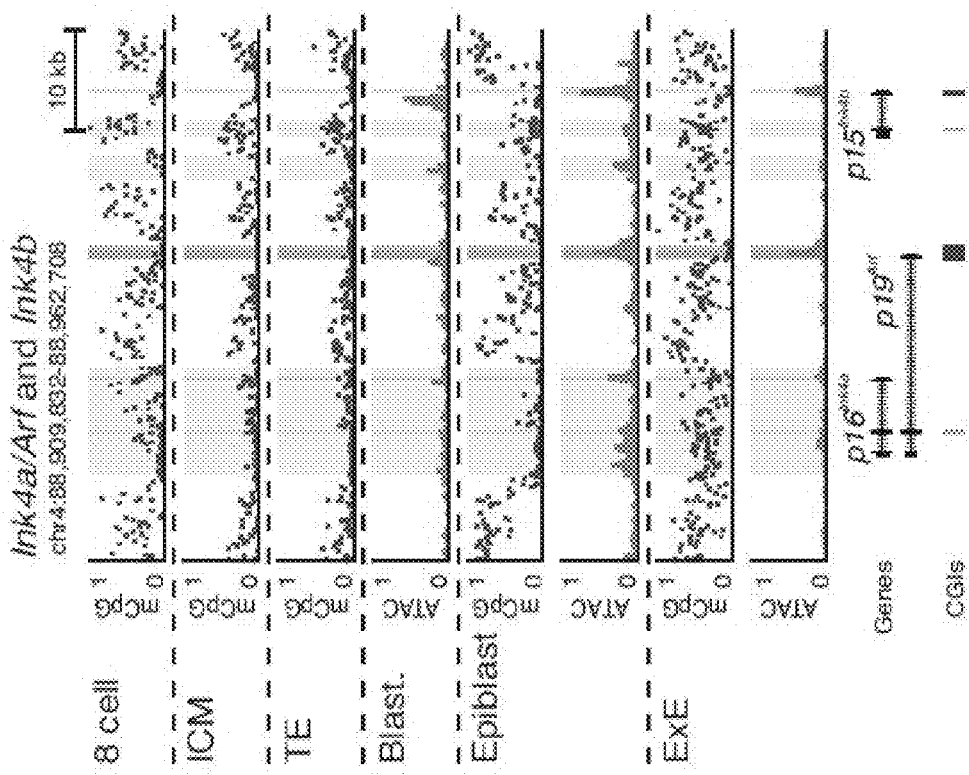
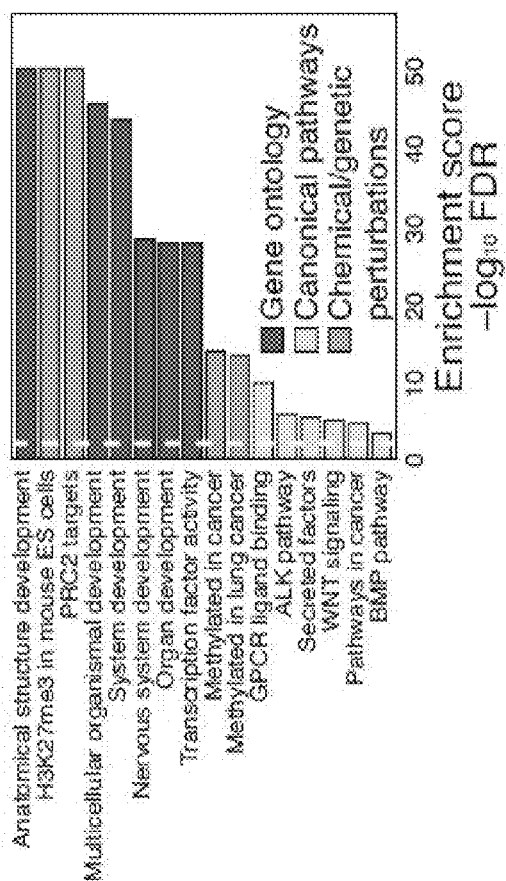
FIG. 7A
FIG. 7B

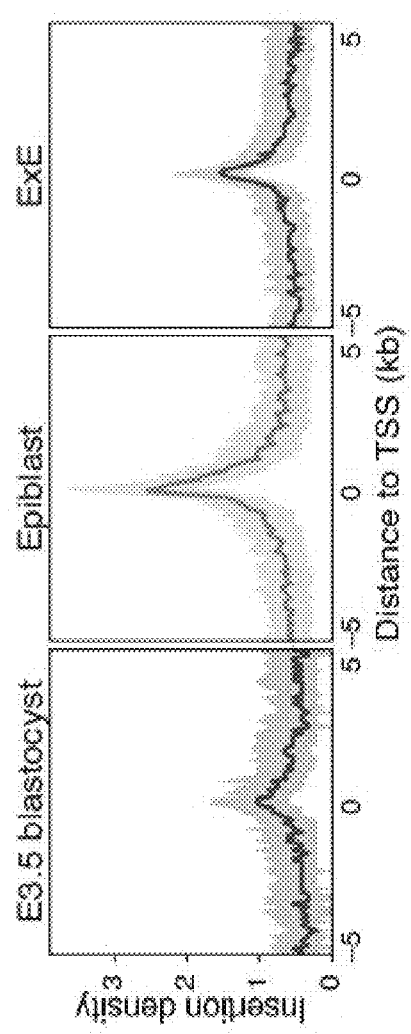
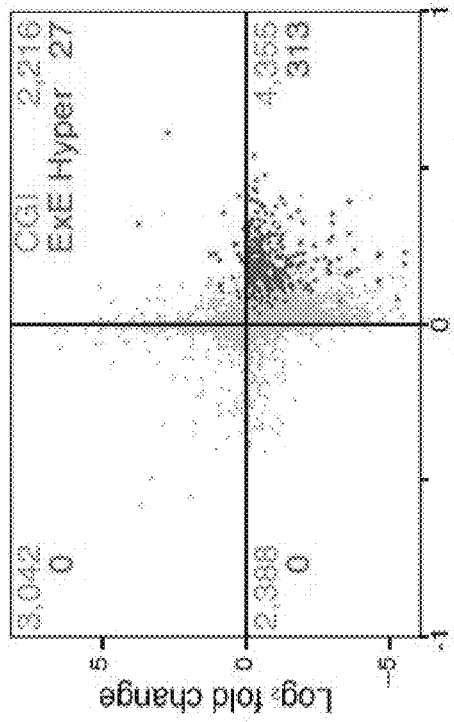
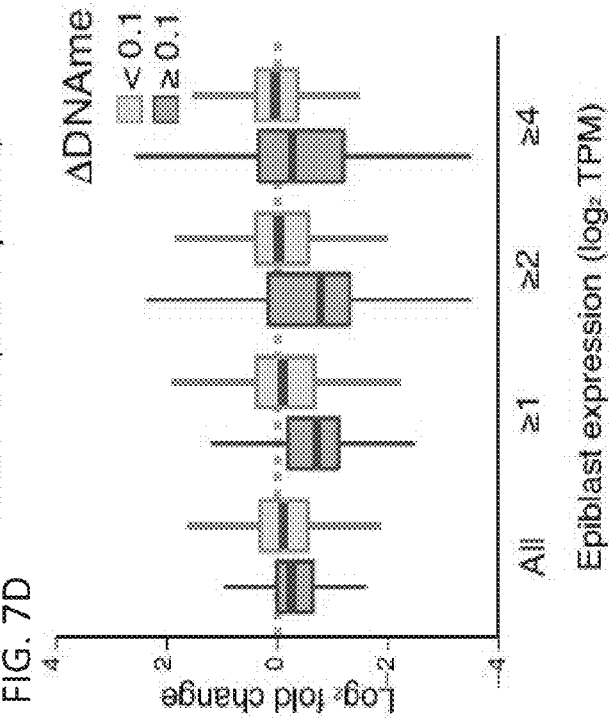
FIG. 7E
FIG. 7C
FIG. 7D

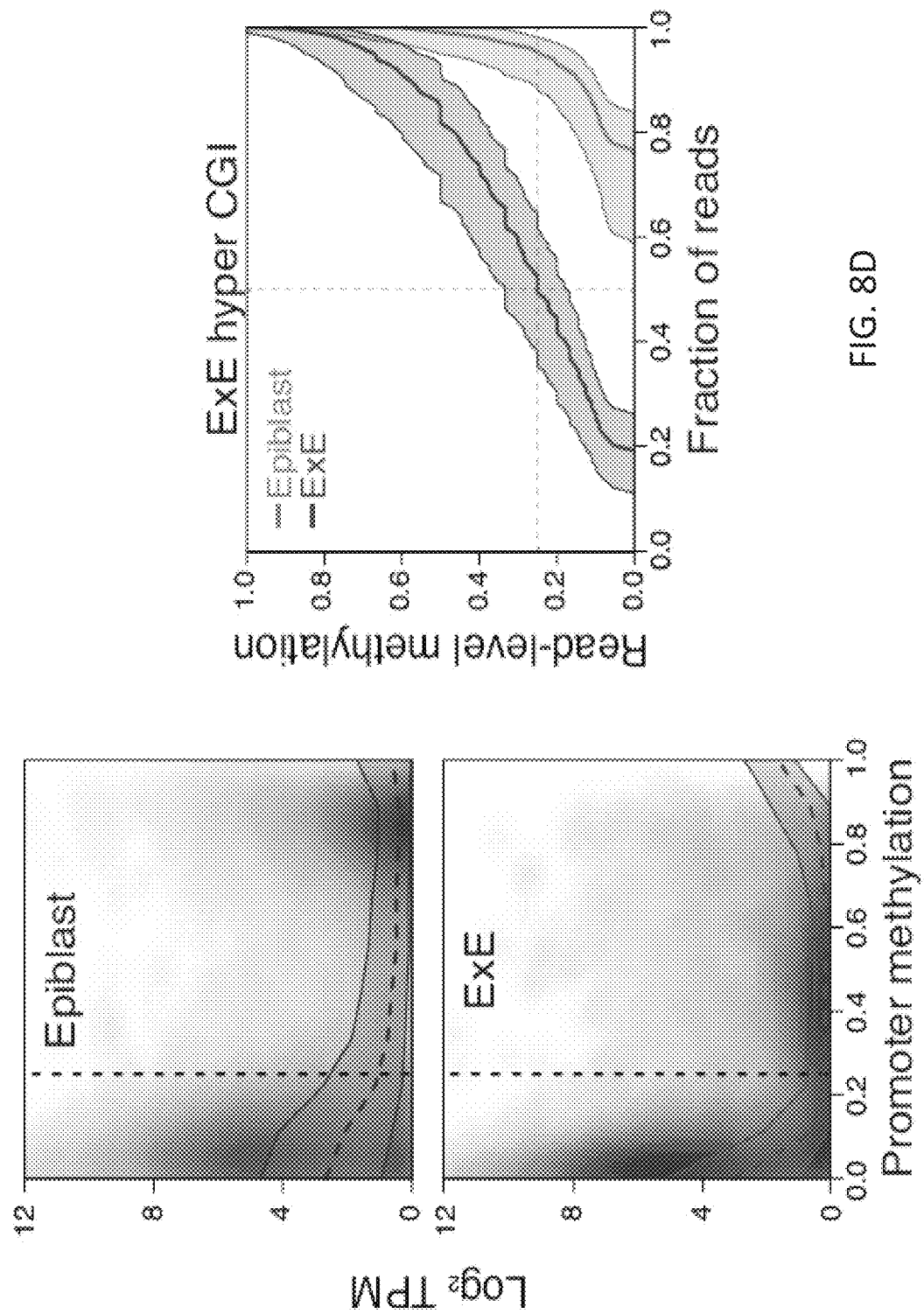

RRBS data

| | Sample | n | Total CpGs | | 100 bp tiles | | | |
|---|---|---|---|---|---|---|---|---|
| | | | 5x | 10x | Median | Mean | Pearson | Euclidean |
| Outgrowth | 2i | 4 | 2,543,848 | 2,277,000 | 0.11 | 0.14 | 0.74 | 0.12 |
| | PD | 6 | 2,708,588 | 2,448,519 | 0.50 | 0.43 | 0.88 | 0.18 |
| | FGF | 5 | 2,666,145 | 2,416,074 | 0.90 | 0.72 | 0.97 | 0.09 |
| | FGF/CHIR inside | 7 | 2,668,463 | 2,424,931 | 0.44 | 0.39 | 0.88 | 0.19 |
| | FGF/CHIR outside | 7 | 2,734,953 | 2,501,819 | 0.31 | 0.31 | 0.85 | 0.14 |
| Epiblast | Wild-type | 4 | 2,479,938 | 2,241,546 | 0.79 | 0.62 | 0.96 | 0.10 |
| | Dnmt1 | 5 | 2,585,520 | 2,341,277 | 0.43 | 0.38 | 0.81 | 0.17 |
| | Dnmt3a | 5 | 2,774,163 | 2,542,382 | 0.77 | 0.60 | 0.97 | 0.11 |
| | Dnmt3b | 6 | 2,765,347 | 2,539,808 | 0.61 | 0.51 | 0.94 | 0.15 |
| | Dnmt3l | 5 | 2,490,838 | 2,242,846 | 0.73 | 0.58 | 0.86 | 0.22 |
| | Eed | 4 | 2,506,687 | 2,246,193 | 0.80 | 0.62 | 0.92 | 0.16 |
| | Kdm2b | 3 | 2,641,642 | 2,365,433 | 0.77 | 0.61 | 0.90 | 0.17 |
| ExE | Wild-type | 4 | 2,520,722 | 2,279,820 | 0.46 | 0.45 | 0.91 | 0.13 |
| | Dnmt1 | 5 | 2,520,255 | 2,274,229 | 0.16 | 0.19 | 0.62 | 0.16 |
| | Dnmt3a | 4 | 2,602,481 | 2,356,566 | 0.43 | 0.42 | 0.85 | 0.17 |
| | Dnmt3b | 6 | 2,543,780 | 2,302,780 | 0.20 | 0.25 | 0.82 | 0.14 |
| | Dnmt3l | 4 | 2,745,180 | 2,479,070 | 0.39 | 0.36 | 0.84 | 0.17 |
| | Eed | 4 | 2,460,919 | 2,178,707 | 0.50 | 0.45 | 0.88 | 0.16 |
| | Kdm2b | 3 | 2,685,969 | 2,435,038 | 0.50 | 0.46 | 0.86 | 0.18 |

FIG. 10A

RNA-seq data

| Sample | | n | Mapped | Median of biological replicates | | |
|---|---|---|---|---|---|---|
| | | | | Exonic rate | Mean per base cov. | Pearson |
| Outgrowth | 2i | 4 | 16,173,599 | 0.93 | 11.29 | 0.98 |
| | PD | 6 | 17,195,224 | 0.91 | 11.38 | 0.96 |
| | FGF | 5 | 19,735,502 | 0.92 | 13.40 | 0.98 |
| | FGF/CHIR inside | 3 | 25,130,944 | 0.91 | 17.51 | 0.99 |
| | FGF/CHIR outside | 3 | 45,754,712 | 0.92 | 33.50 | 0.99 |
| Epiblast | Wild-type | 4 | 13,611,109 | 0.92 | 9.25 | 0.95 |
| | Dnmt1 | 5 | 16,323,776 | 0.90 | 10.93 | 0.94 |
| | Dnmt3a | 5 | 16,092,316 | 0.91 | 10.64 | 0.97 |
| | Dnmt3b | 6 | 17,284,693 | 0.91 | 11.62 | 0.96 |
| | Dnmt3i | 5 | 19,409,738 | 0.91 | 13.25 | 0.97 |
| | Eed | 4 | 28,232,447 | 0.90 | 18.23 | 0.96 |
| | Kdm2b | 3 | 26,003,962 | 0.93 | 18.14 | 0.98 |
| ExE | Wild-type | 4 | 11,537,966 | 0.93 | 8.25 | 0.98 |
| | Dnmt1 | 5 | 16,171,034 | 0.93 | 11.42 | 0.95 |
| | Dnmt3a | 4 | 18,319,262 | 0.93 | 13.10 | 0.96 |
| | Dnmt3b | 6 | 20,682,531 | 0.92 | 15.17 | 0.96 |
| | Dnmt3i | 4 | 20,708,730 | 0.92 | 14.81 | 0.95 |
| | Eed | 4 | 25,794,839 | 0.92 | 17.24 | 0.97 |
| | Kdm2b | 3 | 26,295,000 | 0.93 | 18.60 | 0.91 |

FIG. 10B sgRNA sequences

SEQ ID NOS: 3-20

| Target | sgRNA | Coordinates (mm10) | Sequence |
|---|---|---|---|
| Dnmt1 | 1 | chr9:20936581-20936600;- | GAAACTGGAAGAGGTAACAG |
| Dnmt1 | 2 | chr9:20929059-20929078;- | GACTCCGAGGACAGAGACG |
| Dnmt1 | 3 | chr9:20926483-20926502;+ | AGTATCAAACCAGGTCGAGG |
| Dnmt3a | 1 | chr12:3895692-3895711;+ | GCCAGTAGGAGGGGATGCTG |
| Dnmt3a | 2 | chr12:3896005-3896024;+ | GGCATTGGAGAGCTGGTGTG |
| Dnmt3a | 3 | chr12:3896628-3896647;- | GCTTGTTGTAGGTGGCTGG |
| Dnmt3b | 1 | chr2:153661463-153661482;+ | AGAGGGTGCCAGCGGGTATG |
| Dnmt3b | 2 | chr2:153665300-153665319;+ | GCCTCCCCAGAATCACCCG |
| Dnmt3b | 3 | chr2:153667519-153667538;+ | GGAATAGGTGACCTCGTGTG |
| Dnmt3l | 1 | chr10:78050661-78050680;- | GCCTGTCGGAGGCGAGGAGG |
| Dnmt3l | 2 | chr10:78052046-78052065;+ | TGCACCATCTCGTGTTCCGG |
| Dnmt3l | 3 | chr10:78051869-78051888;+ | CGGCACCCTTGTTTGAGGG |
| Eed | 1 | chr7:89,977,027-89,977,046;- | GATGTGTCAGTATTGAGAG |
| Eed | 2 | chr7:89,970,355-89,970,374;+ | GATCCAGCAACTGCTAATAG |
| Eed | 3 | chr7:89,969,589-89,969,608;+ | GAAGGTTTGGGTCTCGTGGG |
| Kdm2b | 1 | chr5:122888545-122888564;- | TGAAGCAGAGCTGCATCATG |
| Kdm2b | 2 | chr5:122888618-122888637;- | GCCTGCCTGGGACGGAGTG |
| Kdm2b | 3 | chr5:122888692-122888711;+ | GGCAGCCAACTTCACGCTG |

FIG. 10C

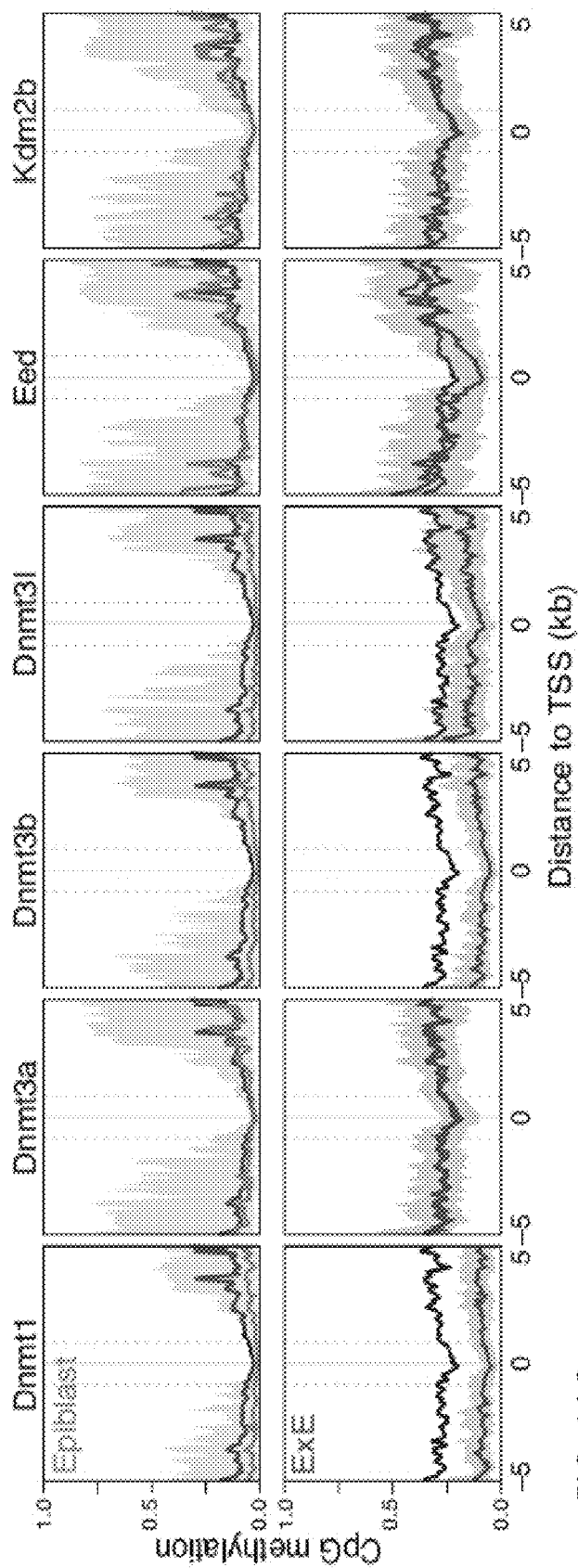
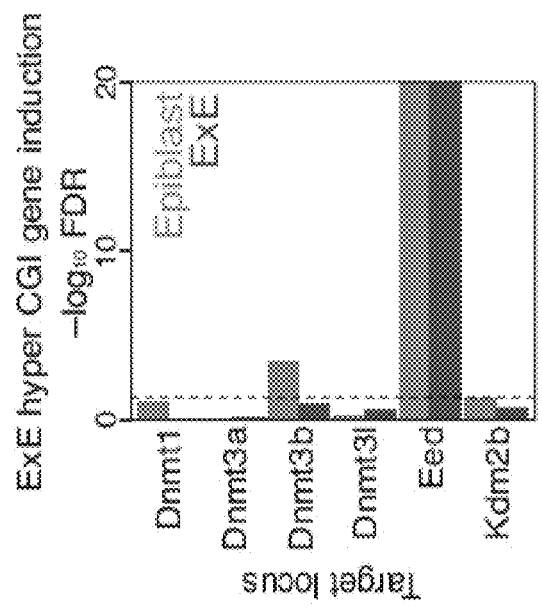
FIG. 11G
FIG. 11H

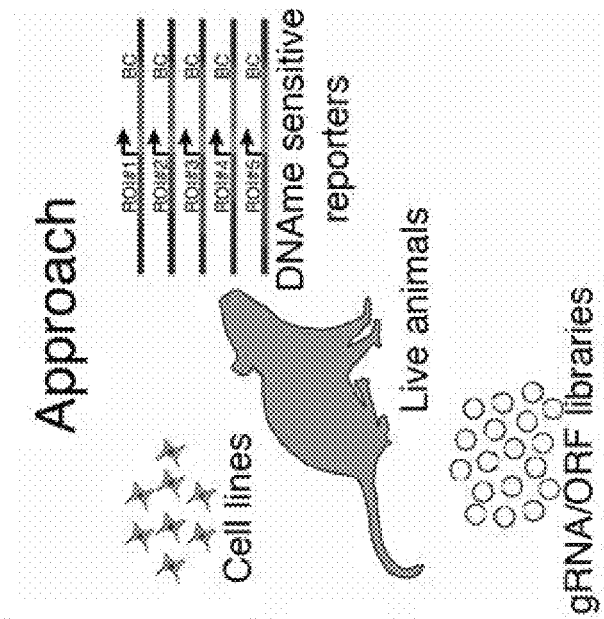
FIG. 20A
FIG. 20B
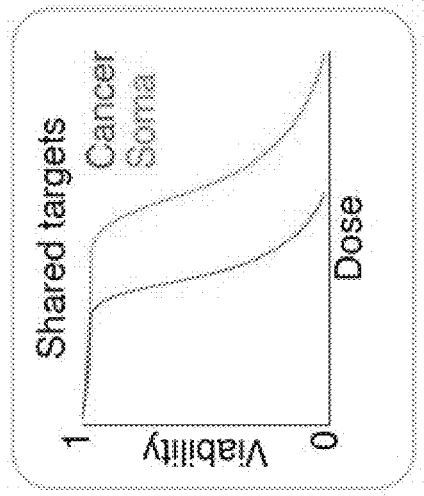
FIG. 20C
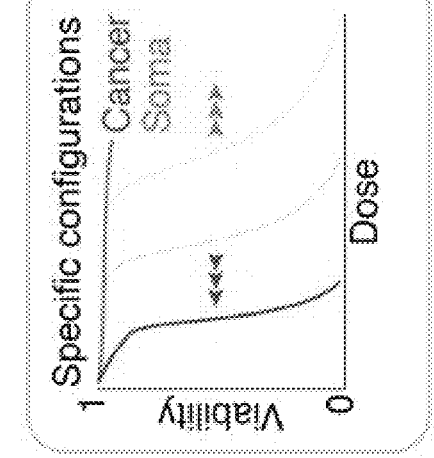
FIG. 20D
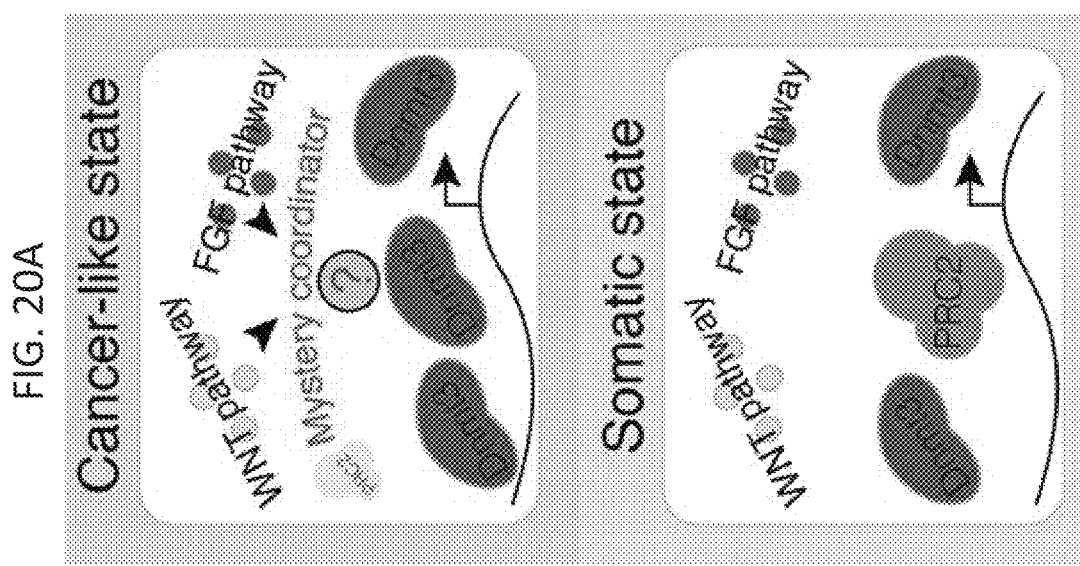
FIG. 20E

UNIVERSAL EARLY CANCER DIAGNOSTICS

RELATED APPLICATIONS

This application is a national stage filing under 35 U.S.C. 371 of International Application No. PCT/US2018/032612, filed May 14, 2018, which claims the benefit of U.S. Provisional Application No. 62/560,660, filed on Sep. 19, 2017, U.S. Provisional Application No. 62/511,648, filed on May 26, 2017, and U.S. Provisional Application No. 62/505,647, filed on May 12, 2017. The entire teachings of the above applications are incorporated herein by reference.

GOVERNMENT SUPPORT

This invention was made with government support under Grant Nos. CA193461, HG006193, GM099117, and DA036898 awarded by the National Institutes of Health. The government has certain rights in the invention.

BACKGROUND OF THE INVENTION

DNA methylation has been used for cancer detection for the past two decades, but current methods rely on mean methylation of a specific gene or gene panels, which lack both sensitivity and specificity for noninvasive cancer diagnosis. In mammals, the canonical somatic DNA methylation landscape is established upon specification of the embryo proper and subsequently disrupted within many cancer types. However, the underlying mechanisms that direct this genome-scale transformation remain elusive, with no clear model for its systematic acquisition or potential developmental utility.

SUMMARY OF THE INVENTION

Disclosed herein are methods for quantifying DNA methylation that may be utilized for screening for diseases (e.g., cancer), diagnosing diseases (e.g., cancer type), monitoring progression of a disease, and monitoring response to a therapeutic treatment.

Disclosed herein are methods of detecting circulating tumor DNA (ctDNA) in a sample comprising using proportion of concordantly methylated reads (PMR) of a sample to detect ctDNA in the sample. In one aspect, a methylation sequence for a sample is obtained, and at least one CpG Island (CGI) is identified on the methylation sequence. PMR for the identified CpG Island is calculated and compared to a control background of a normal tissue or epiblast. The presence of ctDNA is detected in the sample when the PMR of the sample is larger than the control background (e.g., signal is higher by bank sum test).

In certain aspects, the sample is selected from the group comprising plasma, urine, stool, menstrual fluid, or lymph fluid. The sample may comprises cell free DNA. In some aspects, 0.01% to 1% ctDNA, and more specifically 0.01% ctDNA is detected in the sample. In certain aspects, the presence of ctDNA is detected in the sample with a sensitivity of greater than 80%. In some aspects, the presence of ctDNA is detected in the sample with a specificity of greater than 75%. The presence of ctDNA may be detected in the sample with 100% sensitivity and 95% specificity.

In some aspects, the presence of ctDNA is indicative of the presence of a cancer. The sample may be obtained from an individual diagnosed with, suffering from, at risk of developing, or suspected of having cancer. The cancer may be selected from the group comprising bladder urothelial carcinoma, breast invasive carcinoma, colon adenocardinoma, colorectal adenocarcinoma, oseophageal carcinoma, head and neck squamous cell carcinoma, kidney rental clear cell carcinoma, kidney renal papillar cell carcinoma, liver hepatocellular carcinoma, lung adenocarcinoma, lung squamous cell carcinoma, prostate adenocarcinoma, stomach and oesophageal carcinoma, thyroid carcinoma, uterine corpus endometrial carcinoma, and chronic lymphocytic leukaemia. In some aspects, the presence of ctDNA indicates the presence of a tumor.

Also disclosed herein are methods of screening for cancer, comprising using proportion of concordantly methylated reads (PMR) of a sample to detect ctDNA in the sample, wherein the presence of ctDNA is indicative of the subject having cancer.

Also disclosed herein are methods of treating a subject in need of treatment for cancer comprising using proportion of concordantly methylated reads (PMR) of a sample to detect ctDNA in the sample, wherein the presence of ctDNA is indicative of the subject having cancer; and treating the subject for cancer.

Further disclosed herein are methods of monitoring a subject's response to a cancer treatment comprising using proportion of concordantly methylated reads (PMR) of a first sample obtained prior to a subject receiving a cancer treatment to detect an amount of ctDNA in the first sample; using proportion of concordantly methylated reads (PMR) of a second sample obtained after a subject received a cancer treatment to detect an amount of ctDNA in the second sample; and comparing the amount of ctDNA obtained from the first sample and the amount of ctDNA obtained from the second sample, wherein an increase in ctDNA is indicative of a subject's negative response to cancer treatment and a decrease in ctDNA is indicative of a subject's positive response to a cancer treatment.

Also disclosed herein are methods of monitoring progression or amelioration of cancer in a subject, the method comprising using proportion of concordantly methylated reads to identify ctDNA from cfDNA of the subject, wherein if ctDNA is present the subject is at risk of developing cancer, and monitoring the amount of ctDNA in the cfDNA over time, wherein alteration of the amount of ctDNA in the cfDNA is indicative of progression or amelioration of the condition.

Further disclosed herein are methods of assessing cancer in a subject, the method comprising using proportion of concordantly methylated reads to identify the presence of ctDNA from cfDNA of the subject, wherein if ctDNA is present, the subject has or is at risk of developing cancer.

Also disclosed herein, are methods of disrupting methylation of CpG islands comprising reducing expression of PRC2. Also disclosed are methods of disrupting methylation of CpG islands comprising reducing expression of Eed. The expression of Eed may be reduced by a genomic modification (e.g., CRISPR). Further disclosed herein are methods of disrupting methylation of CpG islands comprising reducing expression of Dnmtl, Dnmt3l, or Dnmt3b. Expression of Dnmtl, Dnmt3l, or Dnmt3b may be reduced by a genomic modification (e.g., CRISPR).

Also disclosed herein, are methods of disrupting methylation of CpG islands comprising mutating an FGF pathway member. Further disclosed herein are methods of disrupting methylation of CpG islands comprising mutating an FGFR pathway member.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1E demonstrate divergent post implantation DNA methylation landscapes. FIG. 1A shows early developmental time series collected for this study, including precompacted 8-cell stage embryos (2.25 days post fertilization; E2.25), trophectoderm (TE) and inner cell mass (ICM) of the E3.5 blastocyst, and extraembryonic ectoderm (ExE) and epiblast of the E6.5 conceptus (n=2 WGBS libraries per sample, see Methods). FIG. 1B shows CpG methylation distribution for 100-bp tiles (top); median 100 bp tile methylation as a function of local CpG density (bottom), where the shaded area represents the 25th and 75th percentiles. FIG. 1C shows feature-level enrichment for differentially methylated CpGs compared to genomic background. ExE-hypomethylated CpGs are predominantly found in non-genic sequences, whereas ExE-hypermethylated CpGs localize to CpG islands (CGIs), transcription start sites (TSSs) and 5' exons. Here, TSS refers to the 1 kb upstream of an annotated TSS only, whereas 5' exon and exons represent non-overlapping sets. FIG. 1D shows median methylation architecture flanking ExE-hypermethylated TSSs within embryonic and extraembryonic tissues, as well as the relative methylation difference (A), which diverges considerably upon implantation. The shaded area represents the 25th and 75th percentiles per 100-bp bin. FIG. 1E provides genome browser tracks for WGBS, assay for transposase accessible chromatin with high throughput sequencing (ATAC-seq) and RNA-seq data capturing three emblematic loci. Density refers to the projected number of methylated CpGs per 100 bp of primary sequence and highlights the extensive epigenetic signal present over these regions within ExE (A density refers to the difference compared to the epiblast). For Otx2 and Gata4, ExE-specific methylation and repression are concurrent, whereas the HoxC cluster is expressed later in embryonic development. CGIs are highlighted in green. TPM, transcripts per million.

FIG. 2A provides schematic of signaling pathway interactions between the epiblast (blue) and the ExE (red). Epiblast-produced fibroblast growth factors (FGFs) promote ExE development, which expresses bone morphogenic protein 4 (BMP4) to induce WNT proteins in the epiblast. Epiblast secreted pro-Nodal is processed by the ExE to establish a proximal-distal gradient and the primitive streak[10]. FIG. 2B shows differential expression and promoter methylation of key signaling components between the ExE and epiblast. Many Fgfs and associated receptors exhibit reciprocal expression and promoter methylation. Wnt3 induction is apparent in the epiblast, whereas Wnt6 and 7b are highly expressed in both the trophectoderm and the ExE. Differential promoter methylation refers to the annotated TSS (±1 kb) with the greatest absolute difference. FIG. 2C shows ICM outgrowths are cultured for four days under disparate growth factor or small molecule conditions intended to either stimulate or repress FGF and WNT activity. The outline highlights the purified component (Methods). FIG. 2D shows methylation boxplots for the conditions described in FIG. 2C, including all RRBS-captured 100 bp tiles and ExE-targeted CGIs (ExE hyper CGIs). Edges refer to the 25th and 75th percentiles, whiskers the 2.5th and 97.5th percentiles, respectively. FIG. 2E shows the ExE, FGF/CHIR exterior, and FGF outgrowth all display substantial CGI methylation. Shown is the intersection of methylated CGIs with ≥0.1 increase in comparison to the epiblast (n=3,420). The FGF4 condition has the highest number of methylated CGIs, but fewer intersect with ExE than when CHIR is also present: 25% of ExE hyper CGIs overlap with both conditions, whereas 51% overlap with the FGF/CHIR exterior outgrowth (outside). FIG. 2F shows clustering of differentially methylated CGIs from FIG. 2E, with methylation status in the ExE, embryonic regulation by PRC2, and TSS proximity (±2 kb) included. F/C in and out refer to the interior and exterior FGF/CHIR outgrowth conditions, respectively.

FIGS. 3A-3D demonstrate a novel configuration of epigenetic regulators contributes to the extraembryonic methylation landscape. FIG. 3A provides boxplots for E6.5 epiblast tissue for wild-type (WT) and CRISPR-Cas9 disrupted samples, including for 100 bp tiles and ExE hyper CGIs, as measured by RRBS. Edges refer to the 25th and 75th percentiles, whiskers the 2.5th and 97.5th percentiles, respectively. FIG. 3B provides boxplots as in FIG. 3A for sample-matched ExE. In comparison to the Dnmt3a- and Dnmt3b-positive epiblast, Dnmt1 or Dnmt3b disruption have a far greater effect on global methylation levels and result in a highly depleted genome. FIG. 3C provides composite plots of ExE hyper CGIs by knockout status. CGI methylation is disrupted in Eed-null ExE, particularly within +1 kb of the TSS, without affecting global levels. The black line represents the wild-type median. Composite plots map the median of 200-bp windows over 50-bp intervals from RRBS data. Grey box indicates ±1 kb of the TSS. FIG. 3D provides heat map of the differential CGI methylation (≥0.1) between the CRISPR-Cas9-targeted epiblast or ExE compared to their wild-type counterparts (n=2,461). Differential ExE methylation status in comparison to epiblast and TSS proximity (±2 kb) are included for reference.

FIGS. 4A-4E demonstrate extra embryonically-targeted CpG islands are pervasively methylated across human cancer types. FIG. 4A shows disruption of global methylation creates similar biases for CGIs and promoters between ExE/epiblast or patient- or age-matched normal/cancer tissue comparisons. Heat map shows the log z-score enrichment for features by the binomial test for the above comparisons, as well as for trophectoderm/ICM (TE). Of these 16 cancer types, only THCA does not display a notably dysregulated methylome. n values refer to the number of matched cancer/normal tissue isolates for each type. The Cancer Genome Atlas (TCGA) samples include bladder urothelial carcinoma (BLCA), breast invasive carcinoma (BRCA), colon adenocarcinoma (COAD), colorectal adenocarcinoma (READ), oesophageal carcinoma (ESCA), head and neck squamous cell carcinoma (HNSC), kidney renal clear cell carcinoma (KIRC), kidney renal papillar cell carcinoma (KIRP), liver hepatocellular carcinoma (LIHC), lung adenocarcinoma (LUAD), lung squamous cell carcinoma (LUSC), prostate adenocarcinoma (PRAD), stomach and oesophageal carcinoma (STES), thyroid carcinoma (THCA), and uterine corpus endometrial carcinoma (UCEC). Here, chronic lymphocytic leukaemia (CLL) to B lymphocyte comparison is between age-matched samples measured by WGBS. FIG. 4B provides feature level boxplots of 489 ExE hyper CGIs that preserve their status in humans, calculated as a feature per cancer or normal tissue for the 15 cancer types in which CGI methylation is generally apparent. Asterisk: CLL samples were measured by RRBS (n=119) and represent a comparison between age-matched healthy B lymphocytes (n=24). Edges refer to the 25th and 75th percentiles, whiskers the 2.5th and 97.5th percentiles, respectively. FIG. 4C shows differential methylation heat map for 8,942 orthologous CGIs measured in TCGA or by RRBS and clustered by Euclidean distance. The DMR bar includes the cumulative number of cancer types where a given CGI is called as hypermethylated, as well as the DMR status in either human placenta compared to human embryonic stem (ES) cells (H. placenta), mouse ExE compared to epiblast (M. ExE), or shared between both comparisons (Conserved). PRC2 denotes regulation by Polycomb in human ES cells. The numbers reflect the proportion of each set that is differentially methylated in at least one cancer type. FIG. 4D shows intersection analysis for DMR status across TCGA and CLL samples. Both placenta and ExE DMRs are similarly enriched for methylation in at least one human cancer type (86% and 84%, respectively, compared to 35% for all CGIs) and are more frequently methylated across them. Enrichment for conserved DMRs is greater than for extraembryonic DMRs from each individual species, and 94% are methylated in at least one cancer type. FIG. 4E provides boxplots of orthologous ExE hyper CGIs across 107 ENCODE/Roadmap Epigenomics Project samples, ranked by mean methylation and with cancer or cancer cell line assignment highlighted (red). 'Normal' assigned samples that sort with cancer include the trophoblast cell line HTR8svn, primary colon and colonic mucosa, placenta, and CD8+ T lymphocytes, in descending order.

FIGS. 5A-5F provide sequencing metrics and coverage information for WGBS, RNA-seq, and ATAC-seq data including hierarchical clustering and Pearson correlation for CpGs, genes, and gene promoters, respectively. WGBS data also includes Euclidean distance, which can be beneficial for examining sample similarity in globally hypomethylated samples, as well as similarity scores for 100 bp tiles, which locally merge the intrinsically higher variance of intermediately methylated CpGs to reduce noise. For RNA-seq and ATAC-seq data, biological replicates cluster together, as do 8-cell and post implantation WGBS data, whereas tissues of the E3.5 blastocyst cluster together but not as discrete inner cell mass (ICM) and trophectoderm (TE) compartments. In general, there is minimal variation between the methylation status of the ICM and trophectoderm, with only slight deviations around the minimal global value that is reached during this developmental period. FIG. 5G shows isolation of the epiblast and ExE from the E6.5 post-implantation embryo. The conceptus is first removed from maternal decidual tissue and portioned into epiblast and ExE fractions, taking care to remove the apical ectoplacental cone (EPC). Then, outer visceral endoderm (VE) and trophoblast cells are enzymatically digested and mechanically removed using a thin glass capillary.

FIG. 6A provides CpG methylation boxplots for all covered CpGs as well as those that are significantly hyper- or hypomethylated within the ExE compared to epiblast (ExE hyper or ExE hypo, respectively). ExE hypo CpGs largely reflect differential remethylation compared to the epiblast across the genome. Alternatively, ExE hyper CpGs are mostly unmethylated in the ICM and trophectoderm and remain so in the epiblast, indicating an ExE-specific mechanism. Edges refer to the 25th and 75th percentiles, and whiskers the 2.5th and 97.5th percentiles, respectively. FIG. 6B shows differential methylation distribution for ExE hyper or hypo CpGs compared to epiblast. Hypomethylation appears to be a global feature of the ExE and deviates from a default hypermethylated state in the epiblast. Alternatively, increased DNA methylation appears to be directed focally and de novo at regions that are unmethylated within the epiblast and subsequent embryonic and adult somatic tissues. FIG. 6C shows alternate CpG density distributions for ExE hypo and hyper CpGs indicate differential enrichment within distinct genomic features. Whereas ExE hypo CpGs resemble the global average, ExE hyper CpGs occur within regions of higher CpG densities. FIG. 6D shows the fraction of dynamically methylated CpGs that fall within annotated exons as a function of distance to their assigned TSS. 44% of exonal ExE hyper CpGs fall within 2 kb of their associated TSS. FIG. 6E shows the fraction of dynamically methylated CpGs that fall within annotated CpG islands (CGIs) based upon their proximity to the nearest TSS. ExE hyper CpGs are generally TSS proximal and skew downstream of the TSS, with 43% falling within ±2 kb. FIG. 6F shows DNA methylation distribution for different genomic features including those associated with genic (TSS, exon, intron and CGI) and repetitive (LINE, SINE and LTR) sequences. For reference, black bar and arrows highlight the global median and the 25th and 75th percentiles, respectively. Globally, all features exhibit the expected passage through minimal DNA methylation values within the ICM and trophectoderm of the E3.5 blastocyst before remethylation at implantation. Compared to its global distribution, the ExE exhibits higher levels of de novo methylation within exons and introns, and lower than global levels within regions of LINE and LTR retrotransposon origin. The epiblast exhibits nearly complete hyper or hypomethylation depending on the genomic feature, and is bimodal at TSSs, which frequently contain CGIs. n values refer to the number of annotated features of a given type. FIG. 6G provides violin plots of 100 bp methylation data for early embryonic, placental, and fetal tissues demonstrate general epigenetic retention of either the somatic epiblast or extraembryonic architecture throughout subsequent development. The white dot highlights the global median, and blue and red reflect the median of ExE hypomethylated 100-bp tiles and ExE hyper CGIs, respectively. Notably, the placenta largely preserves the hypomethylated global landscape and targeted CGI methylation as they are established by E6.5 within the ExE. We show 100-bp tiles and CGIs for ExE-specific hypomethylation and hypermethylation, respectively, to restrict CpGs to a notable feature where they change as a group. WGBS data of somatic tissues and midgestation placenta taken from ref 11.

FIGS. 7A-7H demonstrate transcriptional differences between epiblast and ExE are directed in part through DNA methylation. FIG. 7A shows select gene set enrichment analysis of ExE hypermethylated TSSs, including Gene Ontology, canonical pathways, and genetic and chemical perturbations, shows high enrichment for transcription factors and signalling pathways involved in patterning the early embryo. Moreover, these promoter CGI-containing genes are canonical targets of PRC2, which coordinates selective expression of key developmental regulators during gastrulation. FIG. 7B shows DNA methylation and open chromatin dynamics for the tumour suppressors $p16^{Ink4a}$, (both encoded by Cdkn2a) and $p15^{Ink4b}$ (encoded by Cdkn2b). Although these loci are either basally or non-transcribed during early development, three regions are dynamically methylated in the ExE (highlighted in grey), including a >10-kb region that encompasses the entirety of the $p16^{Ink4a}$ locus and is either wholly unmethylated in the epiblast or extensively methylated in the ExE. CGIs are highlighted in green, and the positions of included TSSs are highlighted in red. FIG. 7C provides a scatterplot of log 2 expression dynamics versus differential CGI methylation between the epiblast and the ExE. Although most dynamically methylated CGI promoter-containing genes have functions in later embryonic development and are not yet highly expressed, de novo methylation in the ExE is generally associated with transcriptional repression. ExE hyper CGIs are highlighted in pink. Promoter CGIs are assigned to the most proximal gene within a boundary of ±2 kb. FIG. 7D provides boxplots relating promoter methylation and expression in the restriction of extraembryonic and embryonic compartments. Promoters are defined as ±1 kb of an annotated TSS and scored as dynamically methylated in the ExE if the difference with the epiblast is ≥0.1. Expression changes between dynamically methylated and background promoter sets are provided over increasing thresholds according to their expression in the epiblast. Although many CGI promoter-containing genes are not dynamically expressed in either the epiblast or the ExE and are associated with downstream developmental functions, transcriptional repression is a consistent feature of promoter methylation, even at this low threshold.

FIG. 7E shows median open chromatin signal as measured by ATAC-seq for ExE hyper CGI-associated TSSs in the transition from pre to post implantation. ExE hyper CGI-associated genes are heavily enriched for roles in patterning the embryo proper and are primarily not expressed until the onset of gastrulation. In the transition from blastocyst to epiblast, these promoters gain open chromatin signal, suggesting transcriptional priming or activation, which is not observed within the ExE, where they are de novo methylated. Shaded area reflects the 25th and 75th percentile per fixed 100-bp bin. FIG. 7F shows expression and differential promoter methylation of key epigenetic and master transcriptional regulators over early embryonic and extraembryonic development. Most epigenetic regulators exhibit minimal expression differences between the epiblast and the ExE, with the Dnmts being notable exceptions. Key isoforms of Dnmt3a and Dnmt3b are upregulated in the epiblast in conjunction with global remethylation, whereas the suppression of Dnmt3a in the ExE corresponds with de novo promoter methylation. Alternatively, the maintenance methyltransferase Dnmt1 and the non-catalytic cofactor Dnmt3l are induced within the blastocyst and maintained at higher levels in the ExE, with reciprocal methylation of the Dnmt3l promoter in the epiblast. The H3K36 demethylase Kdm2b displays differential expression of catalytically active and inactive isoforms within the epiblast and the ExE, respectively, with isoform switching seemingly imposed by de novo methylation around the somatically used CGI promoter. The ExE is characterized by persistent expression of the master regulators Cdx2, Eomes, and Elf5 (refs 48-51), whereas the still pluripotent epiblast remains Pou5f1 (also known as Oct4) positive. Many additional regulators of subsequent developmental stages are basally expressed within the epiblast and their promoters de novo methylated in the ExE. The difference in promoter methylation refers to the annotated TSS that exhibits the greatest absolute difference between ExE and epiblast. TPM, transcripts per million. Additional high-resolution genome browser tracks are displayed for select transcriptional and epigenetic regulators in FIGS. 8 and 11, respectively. FIG. 7G shows unsupervised hierarchical clustering of 11,780 genes over late preimplantation and early post-implantation development, partitioned into 20 distinct dynamics ('clusters'). Cluster 10 includes genes that are specifically induced within the epiblast but not the ExE. Heat map intensity reflects the row-normalized z-score. FIG. 7H Significant Gene Ontology enrichment for the 20 gene expression dynamics characterized in FIG. 7F, including those regulated by ExE-methylated CGI promoters, as calculated using the binomial test. Cluster 10 is enriched for both developmental functions and ExE promoter methylation.

FIGS. 8A-8D demonstrate unique bifurcation and epigenetic reinforcement of transcriptional regulators during post implantation development. a, Genome browser tracks for WGBS, ATAC-seq and RNA-seq data for transcriptional regulators associated with embryonic or extraembryonic development. CGIs are highlighted in green, and the positions of included TSSs are highlighted in red. Embryonic regulators include Pou5f1, Nanog, and Pdrm14, which are progressively expressed over preimplantation and for which Pou5f1 and Nanog remain expressed in the epiblast. For these genes, repression in the ExE is accompanied by differential methylation of their TSSs, which is apparent as a local hypermethylation 'peak' at the Pou5f1 locus within an ~5 kb region that is otherwise hypomethylated in the epiblast. At the Nanog locus, an upstream region remains hypomethylated in both tissues. Finally, de novo methylation of the Prdm14 promoter is representative of ExE specific CGI promoter methylation that occurs at hundreds of genes with downstream developmental functions. Density refers to the projected number of methylated CpGs per 100 bp of primary sequence and highlights the extensive epigenetic signal present over these regions within the ExE specifically (Δ density refers to the difference compared to the epiblast). FIG. 8B shows extraembryonic development is in part directed by the master regulator Elf5, which is not induced until implantation and is reciprocally methylated at its TSS in the epiblast. Intriguingly, many transcriptional regulators associated with pluripotency and germline development persist within the ExE, including Zfp42 and the paralogues Dppa2 and Dppa4. As with Elf5, the promoters for these genes are differentially methylated in the epiblast and frequently characterized by broad kilobase-scale hypomethylation surrounding their TSSs in the ExE. FIG. 8C provides scatterplots for log 2 TPM as a function of promoter methylation reveal a higher sensitivity to low methylation levels in the ExE in comparison to the epiblast. Median, 25th, and 75th percentiles for expression within 0.1 methylation bins are included for reference. The fraction of unmethylated promoters is very similar between each tissue and exhibit comparable expression values. Promoters are calculated as ±1 kb of an annotated TSS. Vertical dotted line indicates the median methylation value of ExE hyper CGIs. FIG. 8D shows read-level methylation of ExE hyper CGIs in the ExE and epiblast. The methylation status for every sequencing read within a given CGI was ranked and binned into percentiles. Plotted are the median and the $25^{th}$ and 75th percentiles for these ranks across ExE hyper CGIs for both the ExE and the epiblast. In general, about 80% of reads falling within these regions are methylated in the ExE, with a median methylation value of 0.25. This value is very close to the average, unphased measurement for the CGI entirely, indicating that de novo methylation occurs in a high fraction of cells within the ExE and to a similar extent.

FIG. 9A shows genome browser tracks for WGBS, ATAC-seq and RNA-seq data for select growth factors, receptors, and potentiators that are dynamically regulated during early post-implantation development. Fgf loci such as the ICM-expressed Fgf4 and epiblast-expressed Fgf5 and Fgf8 are all regulated by CGI-containing promoters that are de novo methylated in the ExE. Alternatively, expression of FGF-sensing genes such as Fgfr2 and the potentiating protein Fgfbp1 becomes specific to the ExE and is characterized by broad kilobase-scale hypomethylated domains surrounding their respective TSSs in this tissue. Moreover, the asymmetric allocation of Fgfr2-expressing cells during the specification of the ICM indicates that this tissue is still sensitive to these growth factors before the epigenetic restriction that is imposed by DNA methylation during implantation[52,53]. CGIs are highlighted in green, and the positions of included TSSs are highlighted in red. Density refers to the projected number of methylated CpGs per 100 bp of primary sequence and highlights the extensive epigenetic signal present over these regions within ExE specifically (Δdensity refers to the difference compared to epiblast). FIG. 9B provides bright-field images of ICM outgrowths after two or four days under disparate growth factor or small molecule conditions. All ICMs were cultured on irradiated feeders in a basal N2/B27 media supplemented with leukemia inhibitory factor (LIF). 2i refers to the canonical FGF inhibited, WNT-active condition comprised of the MEK inhibitor PD0325901 and the GSK3β inhibitor CHIR99021, which functions as a WNT agonist[37]. PD refers to culture with PD0325901 alone and represents repressed FGF signaling in the absence of an additional WNT input[54]. FGF4/CHIR represents dual FGF and WNT activity by culture in recombinant FGF4 and CHIR99021 and includes notable interior and exterior tissue structures that emerged during culture and were independently isolated and profiled. Finally, ICMs were cultured in FGF4 alone. Outlines highlight the specific components of each outgrowth that were subsequently purified for analysis by dual RNA-seq and RRBS profiling (see Methods). Scale bar shown on the bottom right. FIG. 9C shows differential methylation of CGIs during in vitro culture differs from the ExE according to developmental trajectory. Shown are specific TSS-associated CGIs that are either methylated in the ExE and both conditions, ExE and FGF/CHIR, or ExE-only and the corresponding mean adjusted log 2 fold change in gene expression. Shared targets include early developmental genes, such as Prdm14, that are repressed in each case, though often highly expressed in the FGF/CHIR interior. Notably, some of these genes, particularly those associated with the germline, can be de novo methylated later in embryonic development[55]. FGF differs from the ExE and FGF/CHIR conditions in the methylation of CGIs associated with either the epiblast or the neuroectoderm, including genes that are expressed in the FGF condition, such as Otx2, Igfbp2, and Sfrp2, though this set encompasses other neuroectodermal master regulators such as Pax6 that are not yet expressed. Finally, ExE and FGF/CHIR diverge in the promoter methylation of endodermal master regulators, such as Foxa2, Hnf1b, Gata4, and Sox/7, which are highly expressed in the transition from FGF/CHIR inside to outside. Notably, the bifurcation in CGI methylation corresponds to the expression of Fgfr2 and repression of Fgf4, as is observed in vivo: Fgf4 is highly expressed within the interior and repressed in the exterior (32.0 to 3.5 TPM) while Fgfr2 is induced (2.3 to 13.5 TPM). PD and FGF/CHIR conditions are also uniquely positive for Dnmt3b and 3l expression, but ExE hyper CGI methylation is not observed with PD0325901 present (TPM=30.2 and 60.9 for Dnmt3b and Dnmt3l in FGF/CHIR outside, and 61.0 and 41.3 for PD), indicating either the requirement for an additional cofactor or post-translational modification to redirect these enzymes to this feature set.

FIGS. 10A-10C demonstrate generation of dual expression and methylation libraries from outgrowth and embryonic knockout data. FIGS. 10A-10B provide sequencing metrics and coverage information for dual RNA-seq and RRBS libraries generated for the evaluation of ICM outgrowths and CRISPR-Cas9 disrupted E6.5 embryos, including similarity metrics between replicates (Euclidean distance and Pearson correlation for RRBS and Pearson correlation for RNA-seq). Mean and median methylation of 100 bp tiles is also included for the RRBS samples. FIG. 10C shows CRISPR-Cas9 disrupted embryos were generated by zygotic injection of three single guide RNA (sgRNA) sequences specific to early exons that are shared across different isoforms. The genomic coordinates and protospacer sequences are provided (see Methods).

FIGS. 11A-11H demonstrate dynamic behavior of key epigenetic regulators during early implantation. Genome browser tracks for WGBS, ATAC-seq and RNA-seq data (log 2 TPM shown for selected isoforms). CGIs are highlighted in green, and the positions of included TSSs are highlighted in red. FIG. 11A shows Dnmt1 is not appreciably expressed in early cleavage, in part owing to a transient maternal imprint over the somatically used TSS (Dnmt1s)[33,56], but shows moderate induction within the ICM. Then, at implantation, it is induced within both the epiblast and the ExE. Dnmt1 is expressed at higher levels within the ExE and displays persistent focal hypomethylation around the maternal-specific TSS (Dnmt1o) that is not observed in the epiblast, which resolves an area of preimplantation specific hypomethylation to the hypermethylated genomic average. FIG. 11B shows the short Dnmt3a2 isoform is induced to high levels in epiblast and is also expressed within embryonic stem (ES) cells. Alternatively, the CGI-containing promoter of Dnmt3a2 is methylated in the ExE and its transcription is suppressed. FIG. 11C shows that like Dnmt1, the Dnmt3b promoter contains a CGI that is maternally imprinted during preimplantation[33,56]. Induction is apparent within the blastocyst, but becomes asymmetrically abundant within the epiblast following implantation. FIG. 11D shows DNMT3L is a non-catalytic cofactor that enhances the de novo activity of DNMT3A and B, with specific functions in the early embryo and germline[57]. During implantation, Dnmt3l is initially expressed in both the ICM and the trophectoderm, but it remains expressed in the ExE and is silenced by de novo promoter methylation in the epiblast. FIG. 11E shows the H3K36 demethylase KDM2B has specific roles in establishing the boundary between promoters and actively transcribed gene bodies, as well as in PRC2 recruitment and the establishment of facultative heterochromatin[58-61]. A catalytically inactive isoform, Kdm2b2, initiates from an alternate TSS downstream of exons encoding the demethylating Jumonji domain of the catalytically active Kdm2b1 (ref. 17). Kdm2b2 is the most prevalent isoform during preimplantation development and remains expressed in the ExE. Alternatively, Kdm2b1 is only induced during implantation within the Epiblast, whereas its CGI-containing promoter gains methylation in the ExE. Like Dnmt1s and Dnmt3b, the CGI promoter of Kdm2b1 is a maternally methylated imprint that resolves to hypomethylation during implantation[33,56]. FIG. 11F shows extraembryonic genome remethylation is highly dependent on DNMT3B and DNMT1. Pairwise comparisons of 100-bp tiles as measured by RRBS for wild-type epiblast and ExE (y axis) versus matched CRISPR-Cas9-disrupted tissues (x axis). Extraembryonic methylation levels diminish genome-wide when Dnmt1, Dnmt3b and Dnmt3l are disrupted. The epiblast is only sensitive to Dnmt1 and Dnmt3b disruption, both to a lesser extent than the ExE, presumably because of compensation from DNMT3A. Notably, the decrease in global methylation levels when Dnmt1 is deleted is greater for ExE than epiblast, indicating a higher dependence on maintenance and less efficient de novo methyltransferase activity in this tissue. The identity line is included in grey and the best fit by LOESS regression in red. The number of 100 bp tiles used in each comparison and the r2 values are included in the upper left of each plot. FIG. 11G provides composite plots of ExE hyper CGI-containing promoters in CRISPR-Cas9 targeted epiblast and ExE, respectively. In general, only limited effects are observed in the epiblast other than a slight increase in the peripheral methylation within the Eed-null sample. Alternatively, both TSS proximal and peripheral methylation is decreased in Dnmt1-, Dnmt3b-, and Dnmt3l-null ExE. The Eed-null ExE is unique in its specificity for diminished methylation at the TSS, particularly downstream within the first kilobase. In both the epiblast and the ExE, the wild-type median is included in black for comparison. Line represents the median and the shaded area the 25th and 75th percentiles, respectively. For RRBS data, composite plots are of the median for 200-bp windows, taken at intervals of 50 bp. FIG. 11H provides statistical test for the derepression of ExE hyper CGI associated genes demonstrates a comparable requirement for Eed in both the epiblast and the ExE. Gene expression of knockout samples were compared to matched wild-type samples using DESeq2 with raw counts as input. Enrichment for ExE hyper CGI associated genes were evaluated by Wilcoxon rank-sum test and represented as z-scores, which were converted to P values assuming a normal distribution. Bonferroni correction for multiple testing was applied to derive the FDR.

FIG. 12A show median methylation of differentially regulated CGI-containing promoters in a primary colon tumor isolate and CLL compared to colon and B lymphocytes, respectively, as measured by WGBS. ExE hyper CGIs as identified in this study and shown in FIG. 1 are included for reference. The median methylation difference between extraembryonic or cancerous tissue compared to the epiblast or normal tissue is also included. The general features of both cancer methylomes are similar to those of the ExE, with a maximal increase in DNA methylation centered at the TSS that steadily diminishes within the periphery. Alternatively, hypomethylated CGIs in extraembryonic or tumorigenic contexts are maximally different a distance away from the TSS, within the boundary or 'CpG island shore', as previously reported for cancer[62]. Shaded area represents the 25th and 75th percentiles per 100-bp bin. FIG. 12B shows read-level methylation of hypermethylated CGIs in the ExE versus the epiblast, colon tumor versus colon, and CLL versus B lymphocyte, with those that share differential methylation status between the cancer and extraembryonic development included as a subset. The methylation status for every sequencing read within a given hypermethylated CGI was ranked and binned into percentiles. Plotted are the median and 25th and 75th percentiles for these ranks across CGIs called as hypermethylated in each pairwise comparison. The ExE/epiblast and CLUB lymphocyte comparisons exhibit very similar distributions that indicate general discordance, meaning similar aggregate methylation across the feature as is observed in phase, which is most likely to be obtained by dispersive de novo methylation across the majority of alleles within the population. Colon tumor exhibits substantially higher read-level methylation, with a median of ~0.7. However, the per-read methylation level of the non-tumorous, matched colon tissue is also quite high, with >50% of reads exhibiting some methylation. This could indicate a transition in the epigenetic status of these loci within colon tissue that precedes tumorigenesis, as has been noted for several other tissues in FIG. 13. The read-level methylation distribution is the same for cancer type-specific CGIs regardless of whether or not they are also ExE hyper CGIs. As such, the targeting to ExE hyper CGIs is a conserved feature of human cancer types, but the extent to which they are methylated can be specific to the system. FIG. 13C provides data taken from ENCODE samples that reflect embryonic and extraembryonic identities in human in comparison to the well-characterized human cancer cell line HCT116. The human ES cell line HUES64, a proxy for the pluripotent epiblast, displays notable enrichment for both repressive, PRC2-deposited H3K27me3 and activating H3K4me3 modifications at orthologous ExE hyper CGIs. Alternatively, human placenta exhibits diminished enrichment for both modifications at these regions, as does HCT116. Both systems display substantial methylation over ExE hyper CGIs as presented in FIG. 4 and FIG. 13. As a control, 'ExE hypo' CGIs demonstrate uniformly high H3K4me3 levels. Enrichment density heat maps are provided for the full ExE hyper CGI set and are ranked across plots according to their enrichment for H3K27me3 in HUES64. Normalized enrichment represents the fold chromatin immunoprecipitation-enrichment against sample matched whole cell extract (WCE). FIG. 12D provides boxplots of mean methylation for 489 ExE-methylated, orthologous CGIs (ExE hyper CGIs) across the 14 tissue-matched TCGA cancer types that display disregulated DNA methylation landscapes and for CLL. Asterisk: CLL samples were measured by RRBS (n=119) and represent a comparison between age-matched healthy B lymphocytes (n=24). Edges refer to the 25th and 75th percentiles, whiskers the 2.5th and 97.5th percentiles, respectively. FIG. 12E provides boxplots for TCGA datasets and CLL for the absolute methylation values of all orthologously mapped CGIs, those methylated across cancer types, and those that are specifically methylated in mouse ExE. In all 15 cancer types that exhibit general global hypomethylation and CGI methylation as part of their departure from somatic cells, ExE hyper CGIs are specifically enriched, more so than for CGIs that are observed as hypermethylated in any given cancer type. FIG. 12F provides boxplots for the same data for cancer type-specific CGI DMRs and those that are also methylated in mouse ExE. Notably, the extent to which mouse ExE hyper CGIs are methylated reflects the cancer type, with some exhibiting higher absolute methylation values than others. However, in 14 out of 15 cases, the absolute methylation status of cancer type-specific CGI DMRs and those that are also methylated in the ExE are nearly identical, and often slightly greater. Absolute methylation values therefore appear to be determined by the specific cancer or cancer type, whereas targeting of extra embryonically methylated CGIs is a general feature.

FIGS. 13A-13B demonstrate broad conservation of extraembryonic methylation patterns across cancer types and cell lines. FIG. 13A provides boxplots of orthologous ExE hyper CGIs across 107 ENCODE/Roadmap Epigenomics Project samples as presented in FIG. 4, with notable additional features of each sample highlighted below. Human extraembryonic tissues, including a trophoblastic cell line and primary placenta, also share conserved CGI methylation with mouse. Normal tissues that appear to exhibit higher mean methylation of ExE hyper CGIs include numerous endodermal lineages, such as colonic mucosa, stomach and liver (mean methylation values of 0.225, 0.185 and 0.179, respectively) as well as mature cell types of the adaptive immune system, such as CD8+ and CD4+T lymphocytes and B lymphocytes (mean methylation values of 0.199, 0.173 and 0.173, respectively). By contrast, ectodermal and epithelial cells are comparatively less methylated than other somatic tissues, although cancer cell lines and primary tumors derived from these tissues remain sensitive to hypermethylation. FIG. 13B shows genome browser tracks for orthologous loci as originally presented for mouse development in FIG. 1 for three human fetal tissues that represent each germ-layer (brain, ectoderm; heart, mesoderm; stomach, endoderm), primary human B lymphocytes, and a CLL sample. CGIs around these loci are preserved in a hypomethylated state during embryonic development, where the bimodal architecture of the DNA methylation landscape is clearly maintained. In B lymphocytes, some low level, encroaching methylation is already apparent over developmentally hypomethylated regions, as is also observed in the Roadmap sample in FIG. 13A. However, in the transition to CLL, extensive methylation is observed across these CGIs although methylation values drop in the surrounding areas. Red line and shaded area reflect the local mean and standard deviation as calculated by local regression (LOESS) to compensate for the greater number of CpGs within the human orthologues versus mouse, which can complicate visual estimates of local methylation at these scales. CGIs are highlighted in green.

FIG. 14A shows intersection analysis as presented in FIG. 4D for cancer hypomethylated CGIs across the 14 TCGA cancer types and CLL that exhibit global loss of methylation in tandem with CGI hypermethylation. Generally, CGI hypomethylation is more specific, such that the intersection across cancers decays exponentially. Notably, even for hypomethylated CGIs, the intersection across cancer types remains higher for those that are also hypomethylated in mouse ExE, human placenta, or both (Conserved). FIG. 14B shows intersection analysis for cancer-dysregulated genes across TCGA cancer types. Of genes significantly dysregulated in at least n (0-14) TCGA cancer types, the fraction of genes that are functionally related to ExE hyper CGI-associated genes were predicted by GRAIL, using a global gene network built by text-mining (see Methods). An FDR of 5% was used as a cut-off. As the number of TCGA cancer types increases, the fraction of ExE hyper CGI-associated genes within the downregulated set generally increases, whereas those that are upregulated decrease substantially. FIG. 14C provides boxplots of the average methylation for the 489 orthologous ExE hyper CGIs across the 10,629 cancers available in TCGA with matched mutational and methylation data, segregated by mutational status of genes that function as part of the FGF signaling pathway. In aggregate, cancers with FGF pathway mutations have a median average ExE hyper CGI methylation level of 0.328 compared to 0.275 for those that do not (P<10-16, rank-sum test). Edges refer to the 25th and 75th percentiles, whiskers the 2.5th and 97.5th percentiles, respectively. FIG. 14D shows that among 539 genes that are present in the top 10 recurrently mutated pathways in cancer, 68 are functionally related to ExE hyper CGI-associated genes (FDR <5%), as predicted by GRAIL. Genes in the FGF signaling pathway are highlighted in red. In general, FGF signaling pathway genes have high connectivity scores to ExE hyper CGI-associated genes (enrichment z-score=3.88 for FGF pathway members within the P value distribution for all 539 genes). FIG. 14E provides statistical enrichment for FGF pathway genes for either amplification or deletion within the TCGA database is notably skewed towards amplification, indicating a generally oncogenic nature for this pathway in tumorigenesis. FIG. 14F shows methylation status of ExE hyper CGIs across colonic and hematopoietic mouse cancer models in which de novo methyltransferase activity has been perturbed. All samples are measured by RRBS. Datasets include: primary colon tissue in which Dnmt3b has been overexpressed (promoter methylation status reported, ref. 63); genetic models of acute myeloid leukemia (AML) including those transformed by the MLL-AF9 fusion (ref. 64), cMyc and BCL2 overexpression (ref. 64), and FLT3 internal tandem duplication (FLT3-IDT, ref. 65); and acute and chronic lymphoblastic leukemia models driven by Dnmt3a knockout alone (refs 66 and 67). Methylation of ExE hyper CGIs is observed in both colonic Dnmt3b overexpression and hematopoietic Dnmt3a knockout. Additional oncogenic drivers appear to induce de novo methylation of these regions in the presence or absence of DNMT3 expression, indicating numerous potentials routes to accomplishing the same molecular phenotype. Wild-type hematopoietic tissues are included for reference and taken from refs 66 and 67. Edges refer to the 25th and 75th percentiles, whiskers the 2.5th and 97.5th percentiles, respectively.

FIG. 15A shows methylation reads can be classified into concordantly unmethylated reads, discordant reads, and concordantly methylated reads. FIG. 15B shows for extraembryonic ectoderm (ExE) hyper-methylated CpG Islands, notable methylation (5%) is still observed in Epilblasts (Epi) when mean methylation is used. In contrast, background noise is significantly reduced when proportion of fully methylated reads (PMR) is applied (FIG. 15C).

FIG. 17A shows the evolution of cancer from normal tissue to metastasis. FIG. 17B identifies a number of genes that may be mutated in lung adenocarcinoma.

FIGS. 20A-20E demonstrate methods for targeting a common molecular pathway. FIG. 20A and FIG. 20B illustrate pathways and factors involved in a cancer-like state (FIG. 20A) and a somatic state (FIG. 20B). Prevailing issues for targeting a common molecular pathway include most molecular targets are shared between the cancer state and the somatic state and there is a reliance on differential sensitivity (FIG. 20C). Solutions for targeting a molecular pathway include identifying target-specific coordinators, inducers or propagators, and cancer-specific interactions (FIG. 20D). FIG. 20E provides an approach for identifying a target of molecular pathways involved in a cancer-like state including single animal screening, using perturb-seq, identifying candidates, and inhibiting/targeting docking sites that misdirect common regulators.

DETAILED DESCRIPTION OF THE INVENTION

Figure 1E:
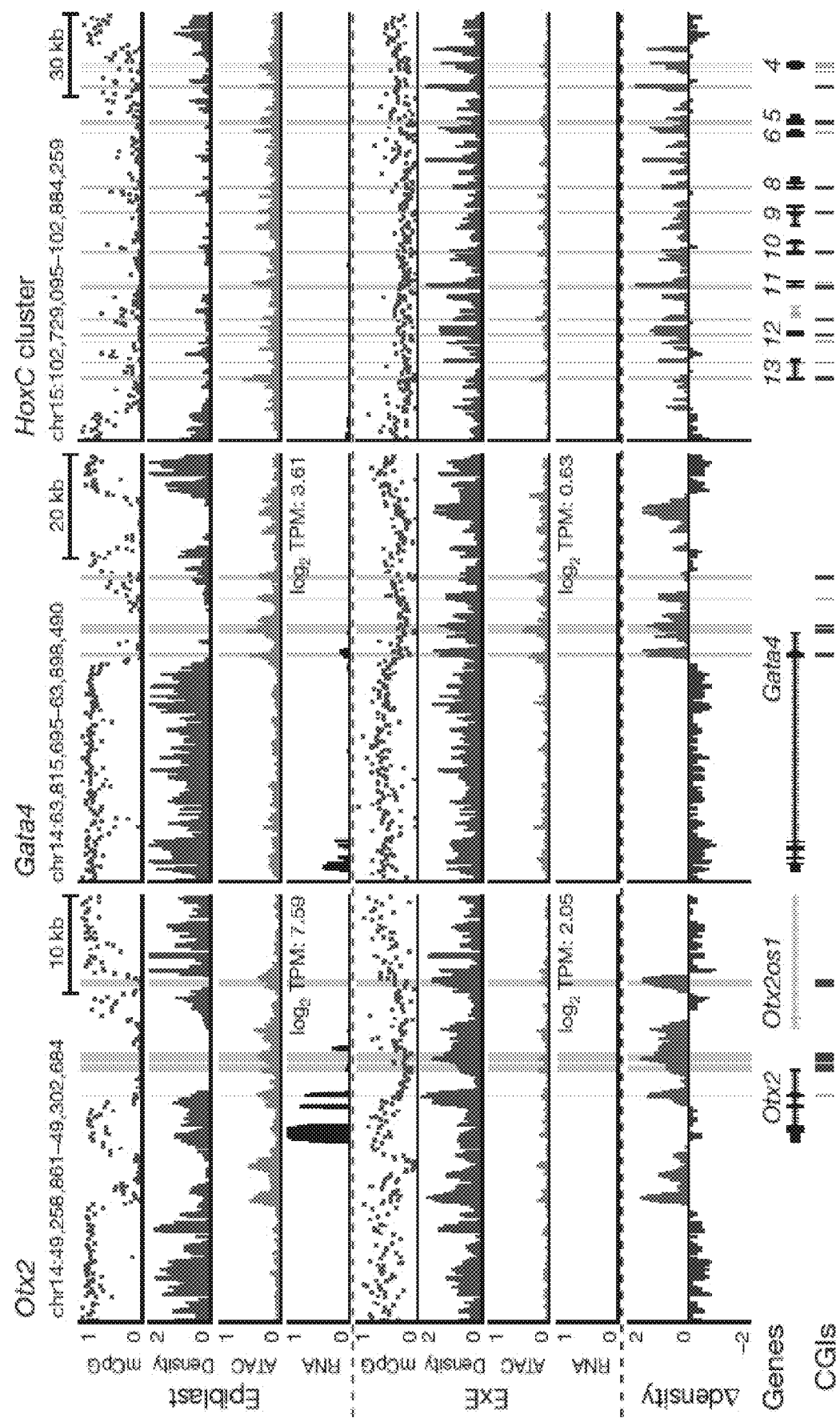

Disclosed herein are methods for quantifying DNA methylation that may be utilized for screening for diseases (e.g., cancer), diagnosing diseases (e.g., cancer type), monitoring progression of a disease, and monitoring response to a treatment regimen. Also disclosed herein is a platform for developing early noninvasive diagnostics that inform novel therapeutic approaches. Also disclosed herein are methods for early detection of highly predictive epigenomic alterations, which include genome-wide misregulation of developmental gene promoters and optimized diagnostics for precise detection at ppm resolution. Also disclosed herein is developmental logic for new molecular therapies, which includes expanding the therapeutic window by targeting unique features of a pan-cancer "cell state."

As used herein, "CpG" and "CpG dinucleotide" are used interchangeably and refer to a dinucleotide sequence containing an adjacent guanine and cytosine where the cytosine is located 5' of guanine.

As used herein, "CpG island" or "CGI" refers to a region with a high frequency of CpG sites. The region is at least 200 bp, with a GC percentage greater than 50%, and an observed-to-expected CpG ratio greater than 60%.

As used herein, a "haplotype" refers to a combination of CpG sites found on the same chromosome. Similarly, a "DNA methylation haplotype" represents the DNA methylation status of CpG sites on the same chromosome.

In certain embodiments, a sample (e.g., a fluid sample) is screened. The sample may be screened using whole-genome bisulfite sequencing (WGBS), TCGA Illumina Infinium HumanMethylation450K BeadChip sequencing (TCGA), and/or reduced representation bisulfite sequencing (RRBS), or by other suitable methylation detection assays known in the art. The identified methylated sequences can be analyzed to identify differentially methylated loci and/or regions (e.g., CpG Islands). In some aspects described herein, for WGBS data, a CGI was considered differentially methylated if it was covered by at least 5 CpGs and 80% of them were significantly hyper/hypo-methylated. In some aspects described herein, for TCGA data, a CGI may be considered differentially methylated if 80% of covered CpGs were significantly hyper- or hypo-methylated. In some aspects described herein, for RRBS data, a cut-off of 10% difference in CGI-level methylation was used to identify differential methylation. In some aspects, the sample is also screened using RNA sequencing (RNA-seq) and/or Assay for Transposase-Accessible Chromatin using sequencing (ATAC-seq).

In some embodiments, DNA methylation haplotypes corresponding to methylation patterns of CpGs are identified from the screening. The DNA methylation haplotypes may be classified into three groups, concordantly unmethylated haplotypes, disordered haplotypes, and concordantly methylated haplotypes. Haplotypes are also referenced to herein as sequencing reads. In some aspects, the proportion of concordantly unmethylated reads (PUR), proportion of disordered reads (PDR), and proportion of concordantly methylated reads (PMR) are calculated. PMR can be used to quantify DNA methylation (e.g., for diagnosis purposes) as described herein.

In certain embodiments, the inventions disclosed herein relate to methods of using proportion of concordantly methylated reads (PMR) (i.e., fully methylated haplotypes) to detect circulating tumor DNA (ctDNA) in a sample. In certain aspects, a methylation sequence for a sample is obtained and at least one CpG Island (CGI) is identified on the methylation sequence. PMR for the identified CpG Island is calculated and then compared to a control background of a normal tissue or epiblast. The presence of ctDNA is detected in the sample when the PMR of the sample is larger than the control background (e.g., signal is higher by bank sum test).

In some aspects, the sample is selected from the group comprising plasma, urine, stool, menstrual fluid, lymph fluid, or any other body fluid in which ctDNA may be located. The sample may comprise DNA (e.g., cell free DNA (cfDNA)). In some aspects, the sample is obtained from a tumor. It is generally understood that the fraction of ctDNA in the sample (e.g., cfDNA) is usually low. In some aspects, the background noise for detecting ctDNA in the sample may be reduced by using a fully methylated haplotype.

The presence of ctDNA may be detected in the cfDNA with a greater sensitivity and specificity than methods previously known by those of skill in the art. For example, ctDNA may be detected in the sample using PMR with a sensitivity of greater than 75%, 80%, 85%, 90%, 95%, or 99%. In certain aspects, ctDNA is detected in the sample using PMR with 100% sensitivity. ctDNA may be detected in the sample using PMR with a specificity of greater than 50%, 55%, 60%, 65%, 70%, 75%, 80%, 85%, 90%, or 95%. In certain aspects, ctDNA is detected in the sample using PMR with 95% specificity. In some aspects, ctDNA is detected in the sample using PMR with at least 90% sensitivity and at least 90% specificity. In some aspects, ctDNA is detected in the sample using PMR with at least 100% sensitivity and at least 95% specificity.

The amount of ctDNA detected in the sample may be measured and quantified. In some aspects, the sample comprises 0.005% to 1.5% ctDNA, 0.01% to 1% ctDNA, 0.05% to 0.5% ctDNA, 0.1% to 0.3% ctDNA. In some embodiments, the sample comprises 0.01% ctDNA. In certain aspects, the presence of 0.01% ctDNA is detected in cfDNA using PMR with about 100% sensitivity and about 95% specificity, with a p-value cutoff of $10^{-4}$.

In certain embodiments, the presence of ctDNA in a sample indicates the presence of cancer. In some aspects, the presence of ctDNA indicates the presence of a tumor. In alternative aspects, the sample is obtained from an individual without a tumor. For example, the sample may be obtained from an individual who is in the early stage of cancer and has not developed a tumor or the individual has a blood cancer (e.g., leukemia). In some aspects, the sample is obtained from an individual diagnosed with, suffering from, at risk of developing, or suspected of having cancer.

As used herein the phrase "cancer" is intended to broadly apply to any cancerous condition. In some aspects, the cancer is selected from the group comprising glioblastoma, colon, lung, breast, and prostate. In certain aspects, the cancer is selected from the group comprising bladder urothelial carcinoma, breast invasive carcinoma, colon adenocarcinoma, colorectal adenocarcinoma, oseophageal carcinoma, head and neck squamous cell carcinoma, kidney rental clear cell carcinoma, kidney renal papillar cell carcinoma, liver hepatocellular carcinoma, lung adenocarcinoma, lung squamous cell carcinoma, prostate adenocarcinoma, stomach and oesophageal carcinoma, thyroid carcinoma, uterine corpus endometrial carcinoma, and chronic lymphocytic leukaemia.

In some embodiments, the inventions disclosed herein relate to methods of screening for cancer by using PMR to detect ctDNA in a sample as described herein, wherein the presence of ctDNA in the sample is indicative of the subject having cancer.

The methods described herein may be applied to a subject who is at risk of cancer or at risk of cancer recurrence. A subject at risk of cancer may be, e.g., a subject who has not been diagnosed with cancer but has an increased risk of developing cancer. Determining whether a subject is considered "at increased risk" of cancer is within the skill of the ordinarily skilled medical practitioner. Any suitable test(s) and/or criteria can be used. For example, a subject may be considered "at increased risk" of developing cancer if any one or more of the following apply: (i) the subject has an inherited mutation or genetic polymorphism that is associated with increased risk of developing or having cancer relative to other members of the general population not having such mutation or genetic polymorphism (e.g., inherited mutations in certain TSGs are known to be associated with increased risk of cancer); (ii) the subject has a gene or protein expression profile, and/or presence of particular substance(s) in a sample obtained from the subject (e.g., blood), that is/are associated with increased risk of developing or having cancer relative to the general population; (iii) the subject has one or more risk factors such as a family history of cancer, exposure to a tumor-promoting agent or carcinogen (e.g., a physical carcinogen, such as ultraviolet or ionizing radiation; a chemical carcinogen such as asbestos, tobacco or smoke components, aflatoxin, arsenic; a biological carcinogen such as certain viruses or parasites); (iv) the subject is over a specified age, e.g., over 60 years of age. A subject suspected of having cancer may be a subject who has one or more symptoms of cancer or who has had a diagnostic procedure performed that suggested or was consistent with the possible existence of cancer. A subject at risk of cancer recurrence may be a subject who has been treated for cancer and appears to be free of cancer, e.g., as assessed by an appropriate method.

In other embodiments, the invention provides methods of treating a subject in need of treatment for cancer. PMR is used to detect ctDNA in a sample as described herein, where the presence of the ctDNA is indicative of the subject having cancer. The individual is then treated for cancer using any methods of treatment generally known to those of skill in the art (e.g., therapeutics or procedures).

For example, therapies or anticancer agents that may be used for treating the subject include anti-cancer agents, chemotherapeutic drugs, surgery, radiotherapy (e.g., γ-radiation, neutron beam radiotherapy, electron beam radiotherapy, proton therapy, brachytherapy, and systemic radioactive isotopes), endocrine therapy, biologic response modifiers (e.g., interferons, interleukins), hyperthermia, cryotherapy, agents to attenuate any adverse effects, or combinations thereof, useful for treating a subject in need of treatment for a cancer. Non-limiting examples of cancer chemotherapeutic agents that may be used include, e.g., alkylating and alkylating-like agents such as nitrogen mustards (e.g., chlorambucil, chlormethine, cyclophosphamide, ifosfamide, and melphalan), nitrosoureas (e.g., carmustine, fotemustine, lomustine, streptozocin); platinum agents (e.g., alkylating-like agents such as carboplatin, cisplatin, oxaliplatin, BBR3464, satraplatin), busulfan, dacarbazine, procarbazine, temozolomide, thioTEPA, treosulfan, and uramustine; antimetabolites such as folic acids (e.g., aminopterin, methotrexate, pemetrexed, raltitrexed); purines such as cladribine, clofarabine, fludarabine, mercaptopurine, pentostatin, thioguanine; pyrimidines such as capecitabine, cytarabine, fluorouracil, floxuridine, gemcitabine; spindle poisons/mitotic inhibitors such as taxanes (e.g., docetaxel, paclitaxel), vincas (e.g., vinblastine, vincristine, vindesine, and vinorelbine), epothilones; cytotoxic/anti-tumor antibiotics such anthracyclines (e.g., daunorubicin, doxorubicin, epirubicin, idarubicin, mitoxantrone, pixantrone, and valrubicin), compounds naturally produced by various species of *Streptomyces* (e.g., actinomycin, bleomycin, mitomycin, plicamycin) and hydroxyurea; topoisomerase inhibitors such as camptotheca (e.g., camptothecin, topotecan, irinotecan) and podophyllums (e.g., etoposide, teniposide); monoclonal antibodies for cancer therapy such as anti-receptor tyrosine kinases (e.g., cetuximab, panitumumab, trastuzumab), anti-CD20 (e.g., rituximab and tositumomab), and others for example alemtuzumab, aevacizumab, gemtuzumab; photosensitizers such as aminolevulinic acid, methyl aminolevulinate, porfimer sodium, and verteporfin; tyrosine and/or serine/threonine kinase inhibitors, e.g., inhibitors of Abl, Kit, insulin receptor family member(s), VEGF receptor family member(s), EGF receptor family member(s), PDGF receptor family member(s), FGF receptor family member(s), mTOR, Raf kinase family, phosphatidyl inositol (PI) kinases such as PI3 kinase, PI kinase-like kinase family members, cyclin dependent kinase (CDK) family members, Aurora kinase family members (e.g., kinase inhibitors that are on the market or have shown efficacy in at least one phase III trial in tumors, such as cediranib, crizotinib, dasatinib, erlotinib, gefitinib, imatinib, lapatinib, nilotinib, sorafenib, sunitinib, vandetanib), growth factor receptor antagonists, and others such as retinoids (e.g., alitretinoin and tretinoin), altretamine, amsacrine, anagrelide, arsenic trioxide, asparaginase (e.g., pegasparagase), bexarotene, bortezomib, denileukin diftitox, estramustine, ixabepilone, masoprocol, mitotane, and testolactone, Hsp90 inhibitors, proteasome inhibitors (e.g., bortezomib), angiogenesis inhibitors, e.g., anti-vascular endothelial growth factor agents such as bevacizumab (Avastin) or VEGF receptor antagonists, matrix metalloproteinase inhibitors, various pro-apoptotic agents (e.g., apoptosis inducers), Ras inhibitors, anti-inflammatory agents, cancer vaccines, or other immunomodulating therapies, etc. It will be understood that the preceding classification is non-limiting.

The present invention also provides a method of monitoring a subject's response to a cancer treatment comprising using PMR of a first sample obtained prior to a subject receiving a cancer treatment to detect an amount of ctDNA in the first sample, using PMR of a second sample obtained after a subject received the cancer treatment to detect an amount of ctDNA in the second sample, and comparing the amount of ctDNA detected in the first sample and the amount of ctDNA detected in the second sample. In some aspects, the amount of ctDNA detected in the second sample will be less than the amount of ctDNA detected in the first sample indicating the subject's positive response to the cancer treatment (e.g., the treatment is effective). In alternative aspects, the amount of ctDNA detected in the second sample will be greater than or the same as the amount of ctDNA detected in the first sample indicating the subject's negative or neutral response to the cancer treatment (e.g, the treatment is not effective).

In other embodiments, the invention provides a method of monitoring progression or amelioration of cancer in a subject. The method comprises using PMR to identify ctDNA from cfDNA of the subject as described herein, wherein if ctDNA is present the subject is at risk of developing cancer, and monitoring the amount of ctDNA in the cfDNA over time, wherein alternation of the amount of ctDNA in the cfDNA is indicative of progression or amelioration of the cancer.

In still other embodiments, the invent provides a method of assessing cancer in a subject, the method comprising using PMR to identify the presence of ctDNA from cfDNA of the subject as described herein, wherein if ctDNA is present, the subject has or is at risk of developing cancer.

In further embodiments, the invention provides methods of identifying DNA methylation signatures for individual cancer types. For example, methylation patterns of CpGs representing single DNA methylation haplotypes may be quantified for specific cancer types. Examples of cancer types include, but are not limited to, colon, lung, lung (squamous), breast, prostate, glioblastoma, bladder, esophagus, head and neck, kidney (clear), kidney (papillary), liver, and uterine (corpus).

In some aspects, the invention provides predictions of cancer tissues of origin using a DNA methylation signature. For example, a methylation signature may be detected with sensitivity and specificity across a variety of tissue systems. Examples of such tissues include, but are not limited to, adrenal, B cell, bladder, bone/soft tissue, brain, breast, cervix, colon, eye, germ cell, head and neck, kidney, liver, lung, myeloid, mesothelium, neuroendocrine, pancreas, prostate, skin, stomach, thymus, and uterine.

The present invention also provides methods for identifying therapeutic targets within one or more molecular pathways. In some aspects, the molecular pathway is common between a somatic state and a cancer-like state. In some aspects, identifying therapeutic targets includes single animal screening, perturb-seq, identifying candidates, and inhibiting and/or targeting docking sites that misdirect common regulators.

The present invention also provides a method of disrupting methylation of CpG islands comprising reducing expression of PRC2. The present invention also provides a method of disrupting methylation of CpG islands comprising reducing expression of Eed. The present invention further provides a method of disrupting methylation of CpG islands comprising reducing expression of Dnmtl, Dnmt3l, or Dnmt3b. In some aspects, expression is reduced by genomic modification (e.g., using CRISPR/Cas or TALEN systems).

CRISPR/Cas systems can employ a variety of Cas proteins (Haft et al. PLoS Comput Biol. 2005; 1(6)e60). In some embodiments, the CRISPR/Cas system is a CRISPR type I system. In some embodiments, the CRISPR/Cas system is a CRISPR type II system. In some embodiments, the CRISPR/Cas system is a CRISPR type V system. It should be understood that although examples of methods utilizing CRISPR/Cas (e.g., Cas9 and Cpf1) and TALEN are described in detail herein, the invention is not limited to the use of these methods/systems. Other methods of targeting polynucleotide sequences to reduce or ablate expression in target cells known to the skilled artisan can be utilized herein.

The present inventions contemplate altering, e.g., modifying or cleaving, target polynucleotide sequences in a cell for any purpose, but particularly such that the expression or activity of the encoded product is reduced or eliminated. In some embodiments, the alteration results in reduced expression of the target polynucleotide sequence. The terms "decrease," "reduced," "reduction," and "decrease" are all used herein generally to mean a decrease by a statistically significant amount. However, for avoidance of doubt, "decreased," "reduced," "reduction," "decrease" includes a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

It should be appreciated that CRISPR/Cas systems can cleave target polynucleotide sequences in a variety of ways. In some embodiments, the target polynucleotide sequence is cleaved such that a double-strand break results. In some embodiments, the target polynucleotide sequence is cleaved such that a single-strand break results.

In some embodiments, CRISPR/Cas systems include a Cas protein or a nucleic acid sequence encoding the Cas protein and at least one to two ribonucleic acids (e.g., gRNAs) that are capable of directing the Cas protein to and hybridizing to a target motif of a target polynucleotide sequence. In some embodiments, CRISPR/Cas systems include a Cas protein or a nucleic acid sequence encoding the Cas protein and a single ribonucleic acid or at least one pair of ribonucleic acids (e.g., gRNAs) that are capable of directing the Cas protein to and hybridizing to a target motif of a target polynucleotide sequence. As used herein, "protein" and "polypeptide" are used interchangeably to refer to a series of amino acid residues joined by peptide bonds (i.e., a polymer of amino acids) and include modified amino acids (e.g., phosphorylated, glycated, glycosolated, etc.) and amino acid analogs. Exemplary polypeptides or proteins include gene products, naturally occurring proteins, homologs, paralogs, fragments and other equivalents, variants, and analogs of the above.

In some embodiments, a Cas protein comprises one or more amino acid substitutions or modifications. In some embodiments, the one or more amino acid substitutions comprise a conservative amino acid substitution. In some instances, substitutions and/or modifications can prevent or reduce proteolytic degradation and/or extend the half-life of the polypeptide in a cell. In some embodiments, the Cas protein can comprise a peptide bond replacement (e.g., urea, thiourea, carbamate, sulfonyl urea, etc.). In some embodiments, the Cas protein can comprise a naturally occurring amino acid. In some embodiments, the Cas protein can comprise an alternative amino acid (e.g., D-amino acids, beta-amino acids, homocysteine, phosphoserine, etc.). In some embodiments, a Cas protein can comprise a modification to include a moiety (e.g., PEGylation, glycosylation, lipidation, acetylation, end-capping, etc.).

In some embodiments, a Cas protein comprises a core Cas protein. Exemplary Cas core proteins include, but are not limited to Cas1, Cast, Cas3, Cas4, Cas5, Cash, Cas7, Cas8 and Cas9. In some embodiments, a Cas protein comprises a Cas protein of an *E. coli* subtype (also known as CASS2). Exemplary Cas proteins of the *E. coli* subtype include, but are not limited to Cse1, Cse2, Cse3, Cse4, and Cas5e. In some embodiments, a Cas protein comprises a Cas protein of the Ypest subtype (also known as CASS3). Exemplary Cas proteins of the Ypest subtype include, but are not limited to Csy1, Csy2, Csy3, and Csy4. In some embodiments, a Cas protein comprises a Cas protein of the Nmeni subtype (also known as CASS4). Exemplary Cas proteins of the Nmeni subtype include, but are not limited to Csn1 and Csn2. In some embodiments, a Cas protein comprises a Cas protein of the Dvulg subtype (also known as CASS1). Exemplary Cas proteins of the Dvulg subtype include Csd1, Csd2, and Cas5d. In some embodiments, a Cas protein comprises a Cas protein of the Tneap subtype (also known as CASS7). Exemplary Cas proteins of the Tneap subtype include, but are not limited to, Cst1, Cst2, Cas5t. In some embodiments, a Cas protein comprises a Cas protein of the Hmari subtype. Exemplary Cas proteins of the Hmari subtype include, but are not limited to Csh1, Csh2, and Cas5h. In some embodiments, a Cas protein comprises a Cas protein of the Apern subtype (also known as CASS5). Exemplary Cas proteins of the Apern subtype include, but are not limited to Csa1, Csa2, Csa3, Csa4, Csa5, and Cas5a. In some embodiments, a Cas protein comprises a Cas protein of the Mtube subtype (also known as CASS6). Exemplary Cas proteins of the Mtube subtype include, but are not limited to Csm1, Csm2, Csm3, Csm4, and Csm5. In some embodiments, a Cas protein comprises a RAMP module Cas protein. Exemplary RAMP module Cas proteins include, but are not limited to, Cmr1, Cmr2, Cmr3, Cmr4, Cmr5, and Cmr6.

In some embodiments, the Cas protein is a *Streptococcus pyogenes* Cas9 protein or a functional portion thereof. In some embodiments, the Cas protein is a *Staphylococcus aureus* Cas9 protein or a functional portion thereof. In some embodiments, the Cas protein is a *Streptococcus thermophilus* Cas9 protein or a functional portion thereof. In some embodiments, the Cas protein is a *Neisseria meningitides* Cas9 protein or a functional portion thereof. In some embodiments, the Cas protein is a *Treponema denticola* Cas9 protein or a functional portion thereof. In some embodiments, the Cas protein is Cas9 protein from any bacterial species or functional portion thereof. Cas9 protein is a member of the type II CRISPR systems which typically include a trans-coded small RNA (tracrRNA), endogenous ribonuclease 3 (rnc) and a Cas protein. Cas 9 protein (also known as CRISPR-associated endonuclease Cas9/Csn1) is a polypeptide comprising 1368 amino acids. Cas 9 contains 2 endonuclease domains, including a RuvC-like domain (residues 7-22, 759-766 and 982-989) which cleaves target DNA that is noncomplementary to crRNA, and an HNH nuclease domain (residues 810-872) which cleave target DNA complementary to crRNA.

In some embodiments, the Cas protein is Cpf1 protein or a functional portion thereof. In some embodiments, the Cas protein is Cpf1 from any bacterial species or functional portion thereof. In some aspects, Cpf1 is a *Francisella novicida* U112 protein or a functional portion thereof. In some aspects, Cpf1 is an *Acidaminococcus* sp. BV3L6 protein or a functional portion thereof. In some aspects, Cpf1 is a *Lachnospiraceae bacterium* ND2006 protein or a function portion thereof. Cpf1 protein is a member of the type V CRISPR systems. Cpf1 protein is a polypeptide comprising about 1300 amino acids. Cpf1 contains a RuvC-like endonuclease domain. Cpf1 cleaves target DNA in a staggered pattern using a single ribonuclease domain. The staggered DNA double-stranded break results in a 4 or 5-nt 5' overhang.

As used herein, "functional portion" refers to a portion of a peptide which retains its ability to complex with at least one ribonucleic acid (e.g., guide RNA (gRNA)) and cleaves a target polynucleotide sequence. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional portion comprises a combination of operably linked Cpf1 protein functional domains selected from the group consisting of a DNA binding domain, at least one RNA binding domain, a helicase domain, and an endonuclease domain. In some embodiments, the functional domains form a complex. In some embodiments, a functional portion of the Cas9 protein comprises a functional portion of a RuvC-like domain. In some embodiments, a functional portion of the Cas9 protein comprises a functional portion of the HNH nuclease domain. In some embodiments, a functional portion of the Cpf1 protein comprises a functional portion of a RuvC-like domain.

It should be appreciated that the present invention contemplates various ways of contacting a target polynucleotide sequence with a Cas protein (e.g., Cas9). In some embodiments, exogenous Cas protein can be introduced into the cell in polypeptide form. In certain embodiments, Cas proteins can be conjugated to or fused to a cell-penetrating polypeptide or cell-penetrating peptide. As used herein, "cell-penetrating polypeptide" and "cell-penetrating peptide" refers to a polypeptide or peptide, respectively, which facilitates the uptake of a molecule into a cell. The cell-penetrating polypeptides can contain a detectable label.

In certain embodiments, Cas proteins can be conjugated to or fused to a charged protein (e.g., that carries a positive, negative or overall neutral electric charge). Such linkage may be covalent. In some embodiments, the Cas protein can be fused to a superpositively charged GFP to significantly increase the ability of the Cas protein to penetrate a cell (Cronican et al. ACS Chem Biol. 2010; 5(8):747-52). In certain embodiments, the Cas protein can be fused to a protein transduction domain (PTD) to facilitate its entry into a cell. Exemplary PTDs include Tat, oligoarginine, and penetratin. In some embodiments, the Cas9 protein comprises a Cas9 polypeptide fused to a cell-penetrating peptide. In some embodiments, the Cas9 protein comprises a Cas9 polypeptide fused to a PTD. In some embodiments, the Cas9 protein comprises a Cas9 polypeptide fused to a tat domain. In some embodiments, the Cas9 protein comprises a Cas9 polypeptide fused to an oligoarginine domain. In some embodiments, the Cas9 protein comprises a Cas9 polypeptide fused to a penetratin domain. In some embodiments, the Cas9 protein comprises a Cas9 polypeptide fused to a superpositively charged GFP. In some embodiments, the Cpf1 protein comprises a Cpf1 polypeptide fused to a cell-penetrating peptide. In some embodiments, the Cpf1 protein comprises a Cpf1 polypeptide fused to a PTD. In some embodiments, the Cpf1 protein comprises a Cpf1 polypeptide fused to a tat domain. In some embodiments, the Cpf1 protein comprises a Cpf1 polypeptide fused to an oligoarginine domain. In some embodiments, the Cpf1 protein comprises a Cpf1 polypeptide fused to a penetratin domain. In some embodiments, the Cpf1 protein comprises a Cpf1 polypeptide fused to a superpositively charged GFP.

In some embodiments, the Cas protein can be introduced into a cell containing the target polynucleotide sequence in the form of a nucleic acid encoding the Cas protein (e.g., Cas9 or Cpf1). The process of introducing the nucleic acids into cells can be achieved by any suitable technique. Suitable techniques include calcium phosphate or lipid-mediated transfection, electroporation, and transduction or infection using a viral vector. In some embodiments, the nucleic acid comprises DNA. In some embodiments, the nucleic acid comprises a modified DNA, as described herein. In some embodiments, the nucleic acid comprises mRNA. In some embodiments, the nucleic acid comprises a modified mRNA, as described herein (e.g., a synthetic, modified mRNA).

In some embodiments, nucleic acids encoding Cas protein and nucleic acids encoding the at least one to two ribonucleic acids are introduced into a cell via viral transduction (e.g., lentiviral transduction).

In some embodiments, the Cas protein is complexed with one to two ribonucleic acids. In some embodiments, the Cas protein is complexed with two ribonucleic acids. In some embodiments, the Cas protein is complexed with one ribonucleic acid. In some embodiments, the Cas protein is encoded by a modified nucleic acid, as described herein (e.g., a synthetic, modified mRNA).

The methods of the present invention contemplate the use of any ribonucleic acid that is capable of directing a Cas protein to and hybridizing to a target motif of a target polynucleotide sequence. In some embodiments, at least one of the ribonucleic acids comprises tracrRNA. In some embodiments, at least one of the ribonucleic acids comprises CRISPR RNA (crRNA). In some embodiments, a single ribonucleic acid comprises a guide RNA that directs the Cas protein to and hybridizes to a target motif of the target polynucleotide sequence in a cell. In some embodiments, at least one of the ribonucleic acids comprises a guide RNA that directs the Cas protein to and hybridizes to a target motif of the target polynucleotide sequence in a cell. In some embodiments, both of the one to two ribonucleic acids comprise a guide RNA that directs the Cas protein to and hybridizes to a target motif of the target polynucleotide sequence in a cell. The ribonucleic acids of the present invention can be selected to hybridize to a variety of different target motifs, depending on the particular CRISPR/Cas system employed, and the sequence of the target polynucleotide, as will be appreciated by those skilled in the art. The one to two ribonucleic acids can also be selected to minimize hybridization with nucleic acid sequences other than the target polynucleotide sequence. In some embodiments, the one to two ribonucleic acids hybridize to a target motif that contains at least two mismatches when compared with all other genomic nucleotide sequences in the cell. In some embodiments, the one to two ribonucleic acids hybridize to a target motif that contains at least one mismatch when compared with all other genomic nucleotide sequences in the cell. In some embodiments, the one to two ribonucleic acids are designed to hybridize to a target motif immediately adjacent to a deoxyribonucleic acid motif recognized by the Cas protein. In some embodiments, each of the one to two ribonucleic acids are designed to hybridize to target motifs immediately adjacent to deoxyribonucleic acid motifs recognized by the Cas protein which flank a mutant allele located between the target motifs.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

It is to be understood that the inventions disclosed herein are not limited in their application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

While certain compositions, methods and assays of the present invention have been described with specificity in accordance with certain embodiments, the following examples serve only to illustrate the methods and compositions of the invention and are not intended to limit the same.

EXAMPLES

Example 1: Epigenetic Restriction of Extraembryonic Lineages Mirrors the Somatic Transition to Cancer In mammals, the canonical somatic DNA methylation landscape is established upon specification of the embryo proper and subsequently disrupted within many cancer types[1-4]. However, the underlying mechanisms that direct this genome-scale transformation remain elusive, with no clear model for its systematic acquisition or potential developmental utility[5,6]. Here, global remethylation was analyzed from the mouse preimplantation embryo into the early epiblast and extraembryonic ectoderm. It was shown that these two states acquire highly divergent genomic distributions with substantial disruption of bimodal, CpG density-dependent methylation in the placental progenitor[7,8]. The extraembryonic epigenome includes specific de novo methylation at hundreds of embryonically protected CpG island promoters, particularly those that are associated with key developmental regulators and are orthologously methylated across most human cancer types[9]. The data suggest that the evolutionary innovation of extraembryonic tissues may have required co-option of DNA methylation-based suppression as an alternative to regulation by Polycomb-group proteins, which coordinate embryonic germ-layer formation in response to extraembryonic cues[10]. Moreover, it was established that this decision is made deterministically, downstream of promiscuously used—and frequently oncogenic—signaling pathways, via a novel combination of epigenetic cofactors. Methylation of developmental gene promoters during tumorigenesis may therefore reflect the misappropriation of an innate trajectory and the spontaneous reacquisition of a latent, developmentally encoded epigenetic landscape.

Figure 6A:
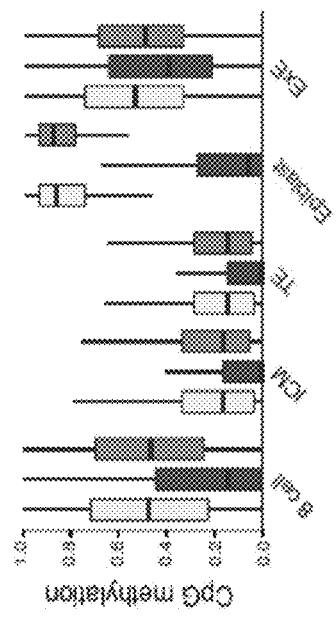
FIGS. 6A-6G demonstrate unique features of the extraembryonic methylation landscape.
Figure 6B:
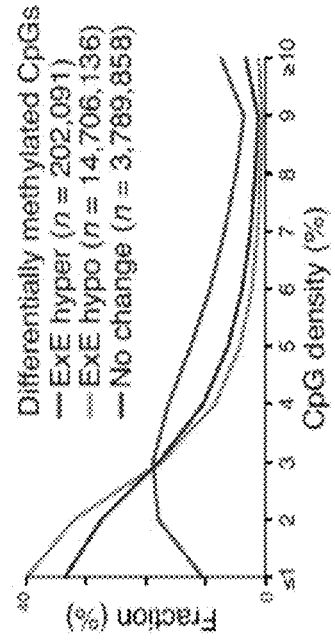
Figure 6D:
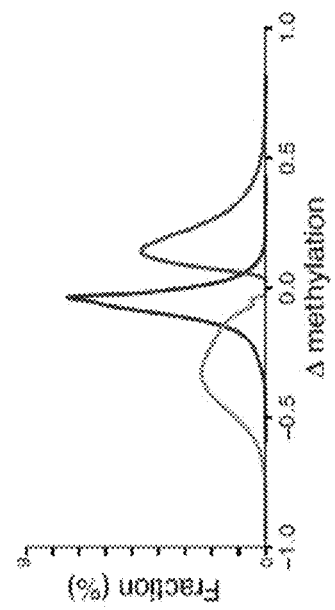
Figure 6C:
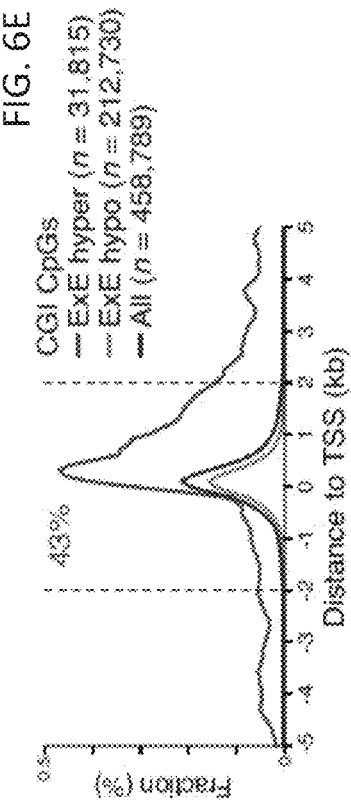
Figure 6E:
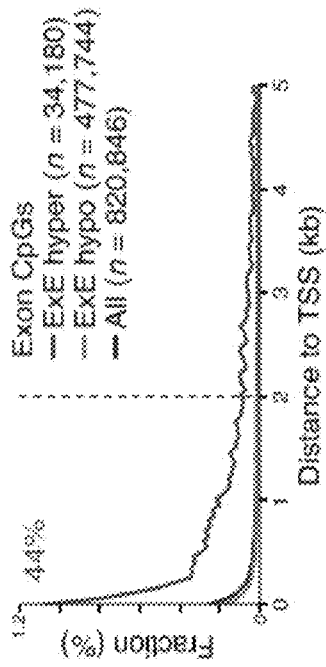
Figure 6F:
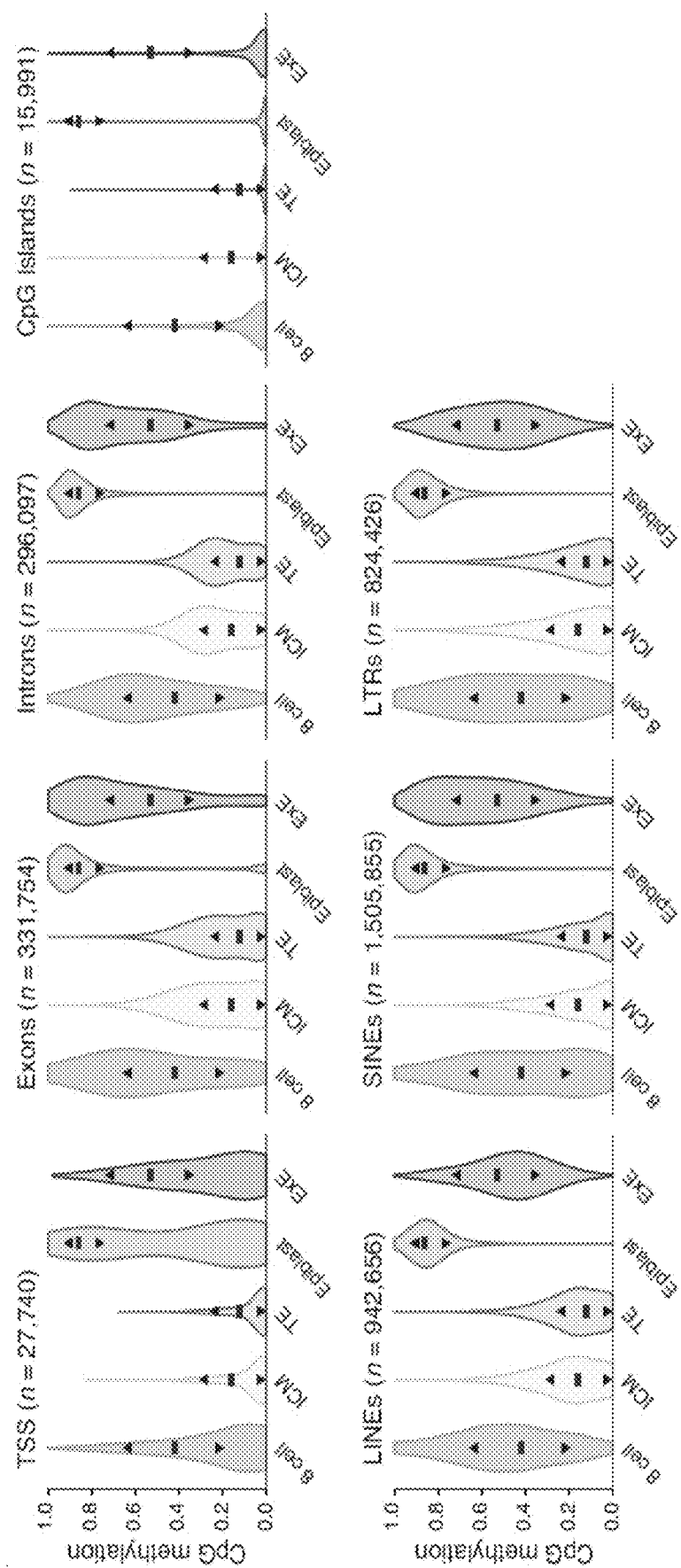
Figure 6G:
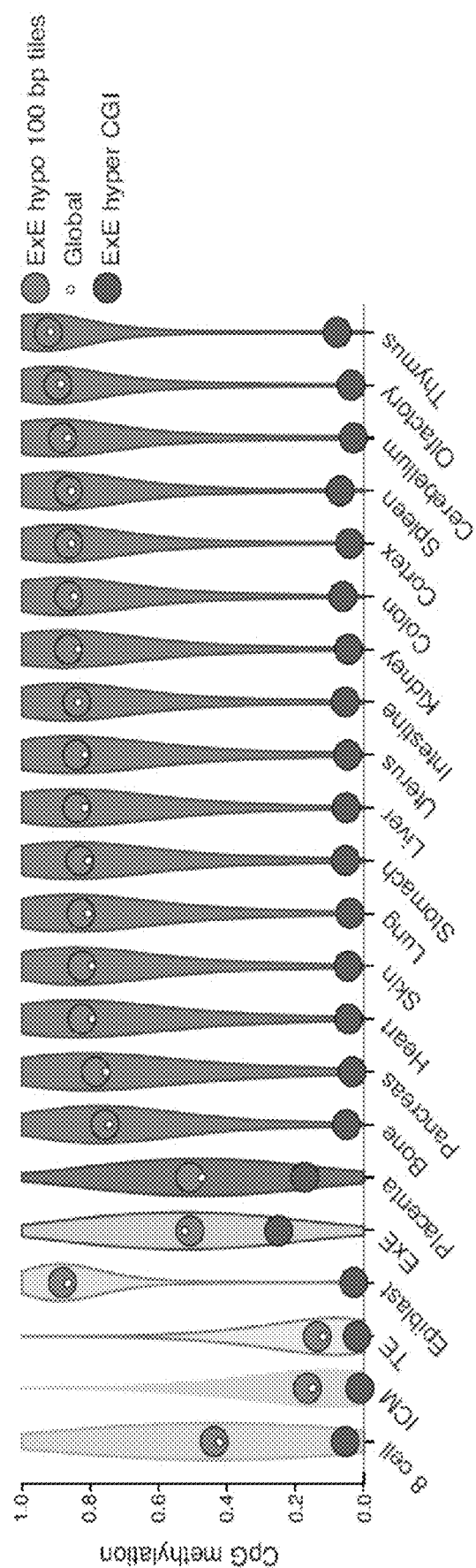

To compare how epigenetic landscapes evolve during early mammalian development, whole-genome bisulfite sequencing (WGBS) and RNA sequencing (RNA-seq) datasets were generated from mouse precompacted 8-cell stage embryos, inner cell mass (ICM) and trophectoderm from embryonic day (E)3.5 blastocysts, as well as epiblast and extraembryonic ectoderm (ExE) from E6.5 conceptuses, the latest stage at which these progenitors remain largely homogeneous and undifferentiated (FIG. 1A, FIG. 5). Holistically, the time series captures the expected transition through the indistinguishably hypomethylated—but transcriptionally distinct—blastocyst-stage tissues, followed by a considerable departure at implantation, at which approximately 80% of the genome becomes differentially methylated (FIG. 6A). Specifically, the extraembryonic lineage lacks canonical bimodality: most CpGs are incompletely methylated in comparison to the epiblast and 1.36% are methylated in the ExE (FIG. 1B, FIG. 6B). ExE-specific hypo- or hypermethylated CpGs segregate into distinct genomic compartments by CpG density and location, with de novo methylation preferentially enriched for CpG islands (CGIs) near transcription start sites (TSSs) and 5' exons (FIG. 1C, FIGS. 6C-6F). Once established, these two alternative landscapes are largely preserved across embryonic tissues or in the midgestation placenta, respectively[11,12] (FIG. 6G).

Figure 4D:
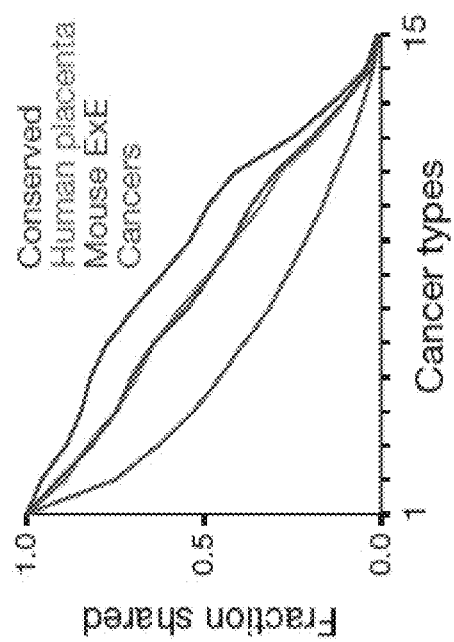
Figure 7F:
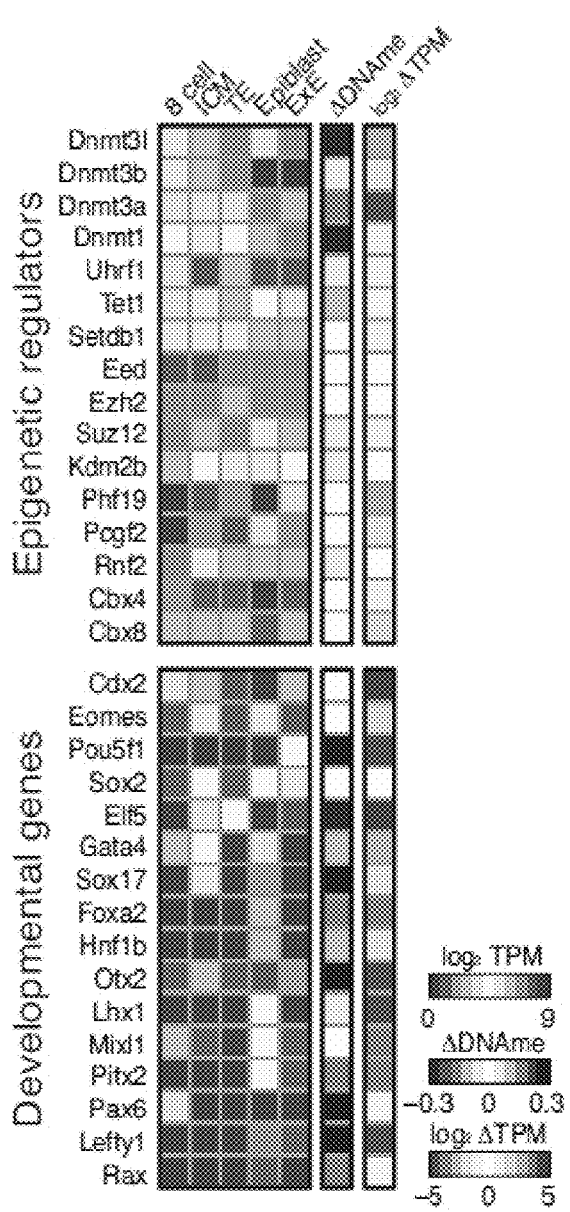
Figure 7G:
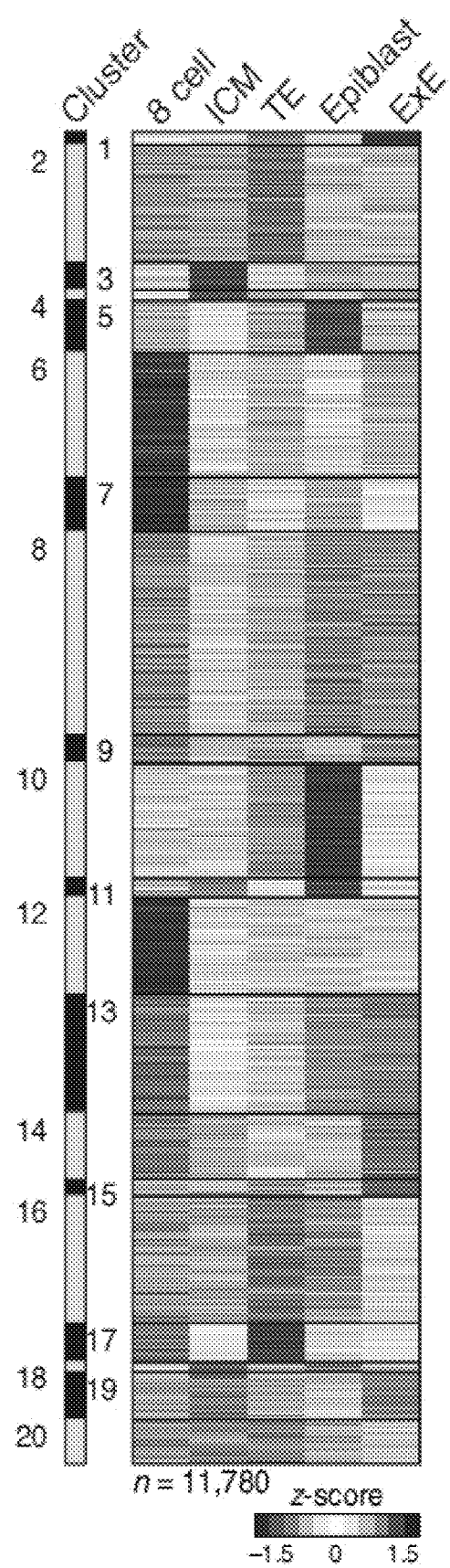
Figure 7H:
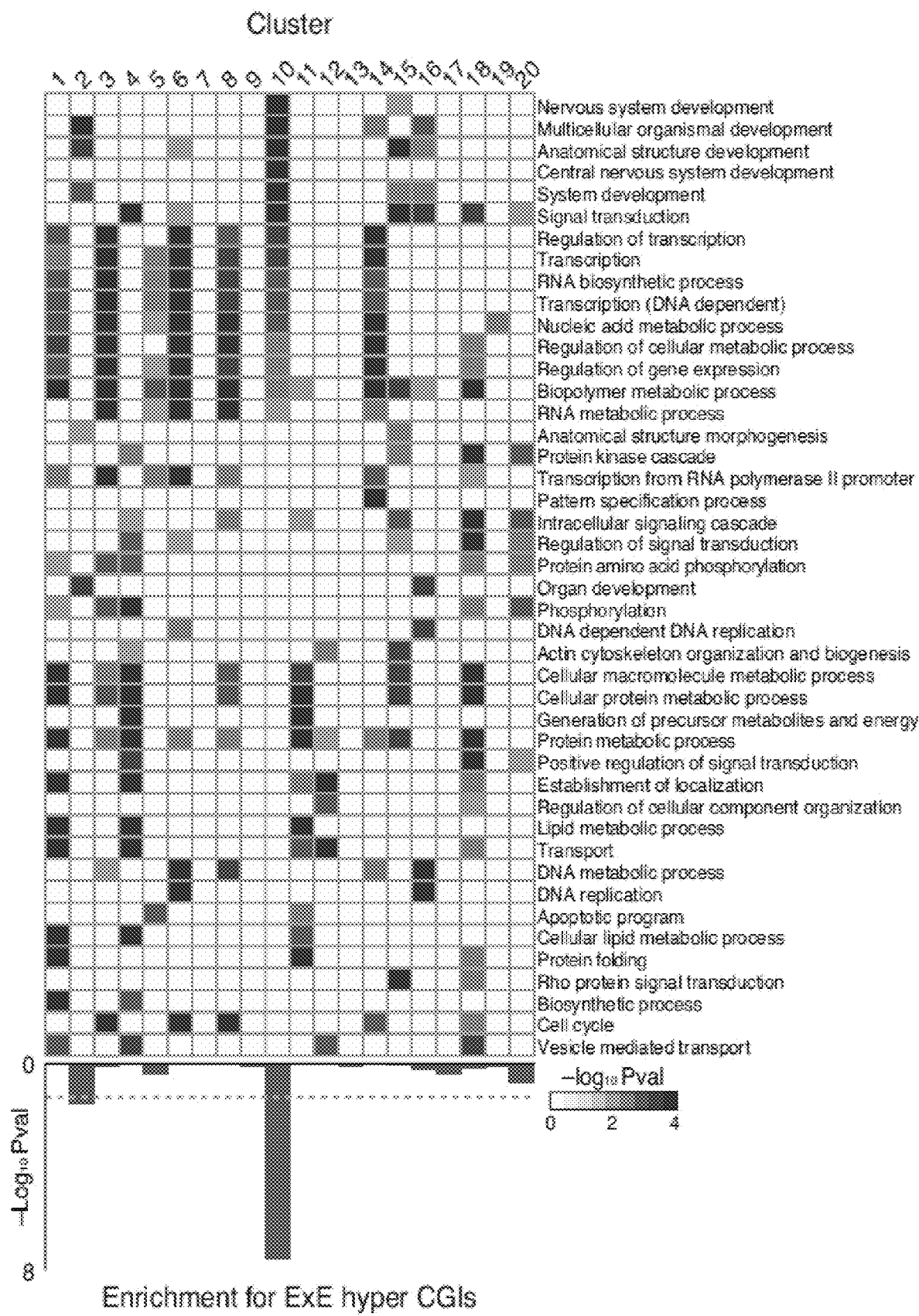
Figure 8A:
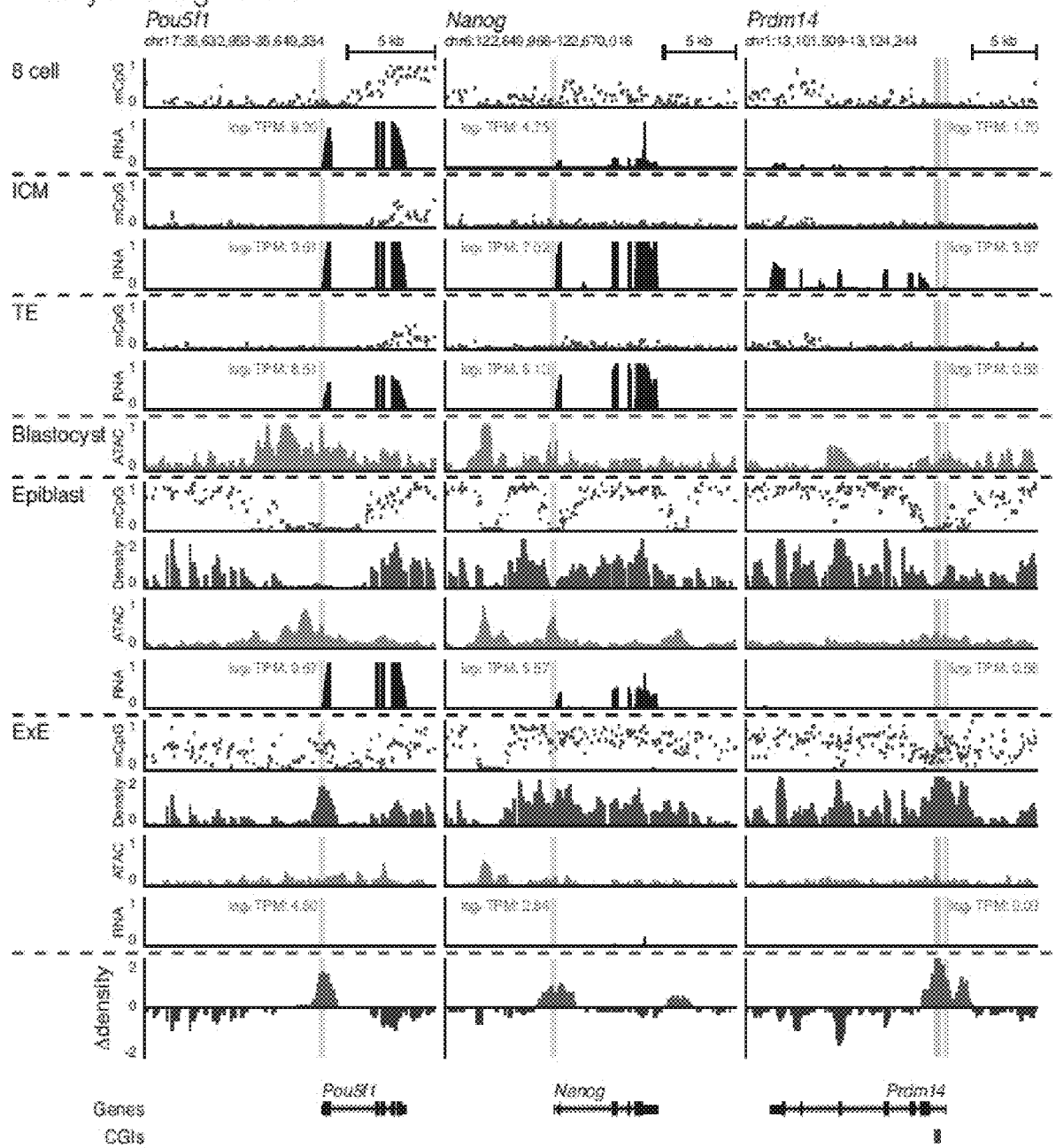
Figure 8B:
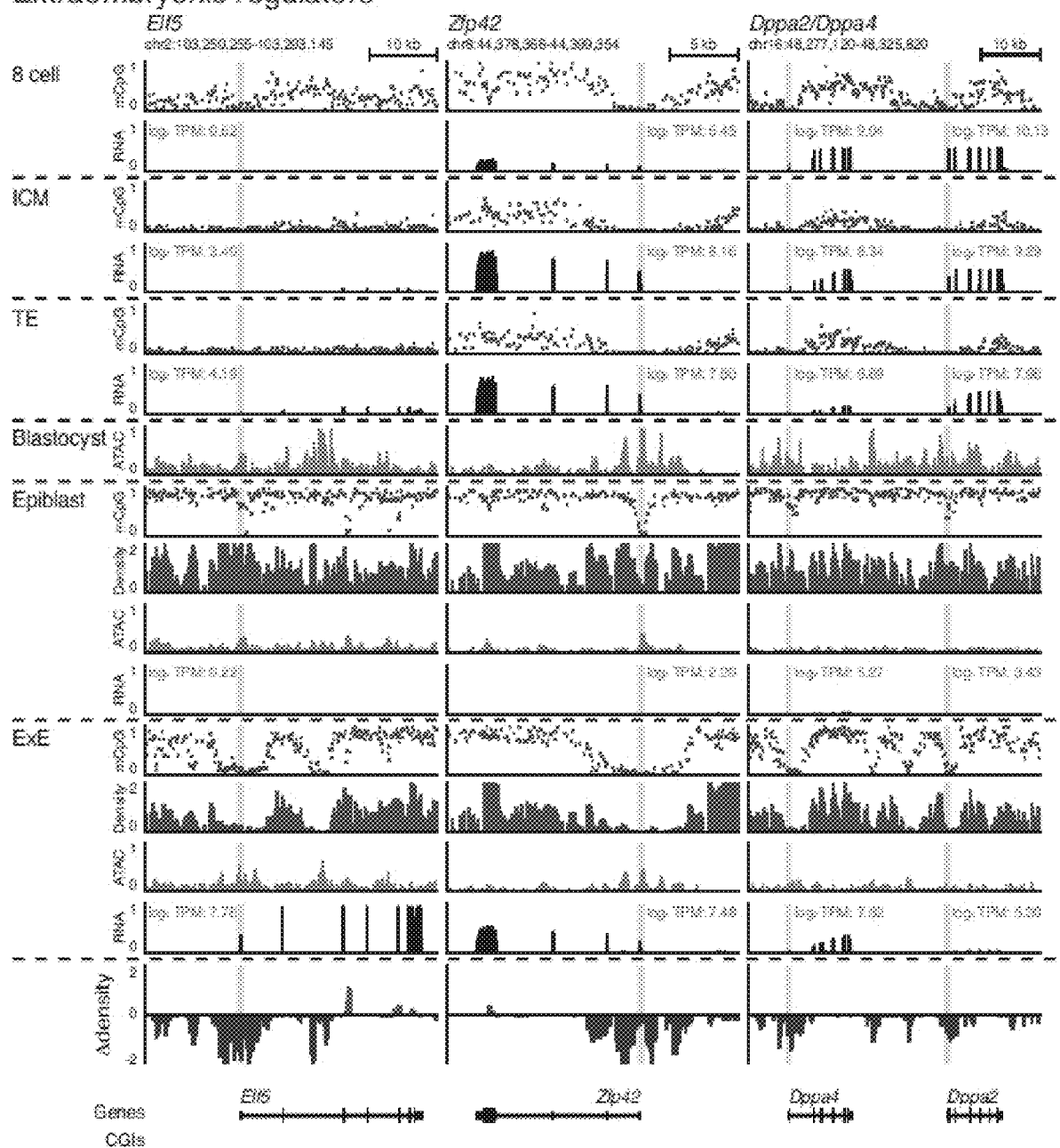

Notably, ExE-methylated CGIs (ExE hyper CGIs) frequently overlap with Polycomb repressive complex 2 (PRC2)-regulated genes, including master transcription factors that direct germ-layer and body-axis formation (FIGS. 7A-7B). Although the majority of targeted genes are not yet expressed in the epiblast, ExE-specific promoter methylation is generally associated with repression, including of many pluripotency-specific regulators, as well as concurrent loss of chromatin accessibility (FIGS. 7-8). Moreover, the global relationship between promoter methylation and gene repression is more pronounced in the ExE than in the epiblast (FIG. 8C). DNA methylation surrounding these promoters is largely dispersive, with flanking regions less methylated in the ExE than in the epiblast, but with a maximal increase specifically at the TSS (FIGS. 1D-1E). ExE hyper CGIs only reach methylation levels of ~0.25, but methylated CpGs are distributed across 80% of the sequencing reads that fall within them and have a median per-read methylation status that matches the unphased measurement (FIG. 4D). The consistency between per-molecule and aggregate methylation is most likely to be explained by population-wide recruitment of de novo methyltransferases, followed by stochastic gains at individual CpGs in phase, similar to a variety of cancer systems[13,14]. Importantly, the higher CpG density of ExE-targeted regions leads invariably to a higher local methylation density, even though the per-CpG methylation status is intermediate (FIG. 1E).

Figure 2B:
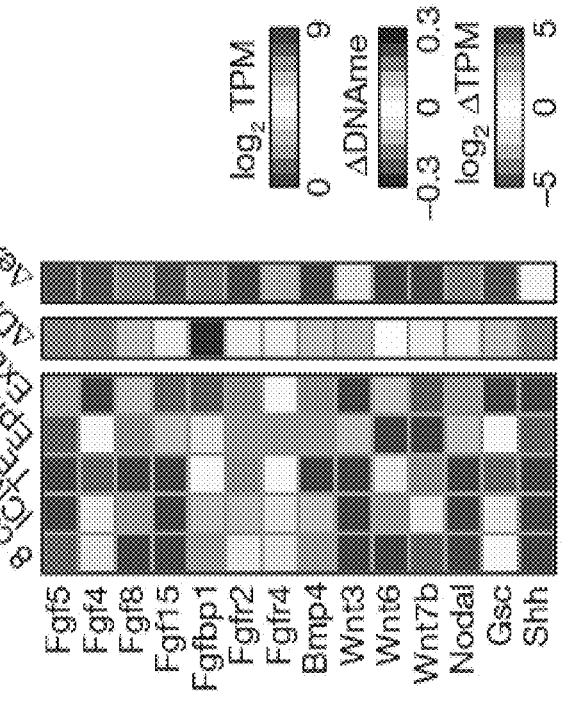
FIGS. 2A-2F demonstrate de novo methylation of early developmental gene promoters can be modulated by external conditions.
Figure 2A:
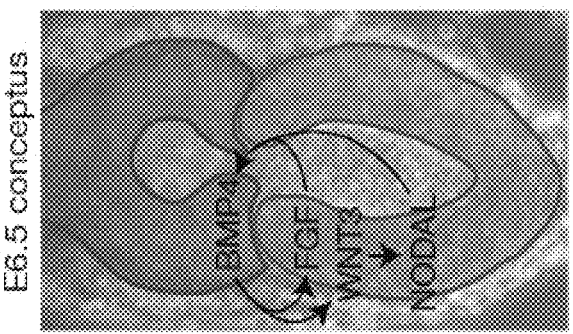
Figure 2D:
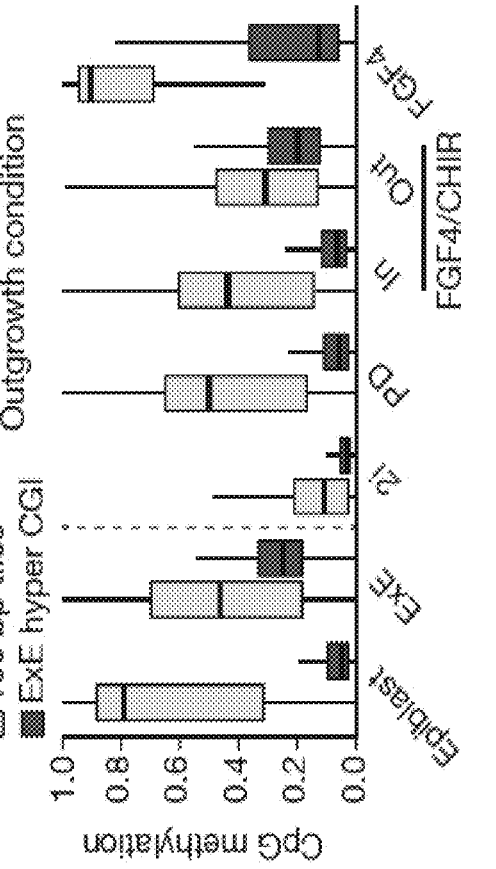
Figure 2C:
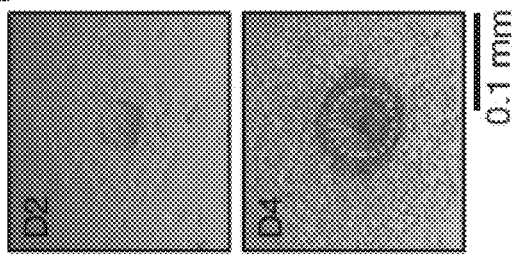
Figure 9A:
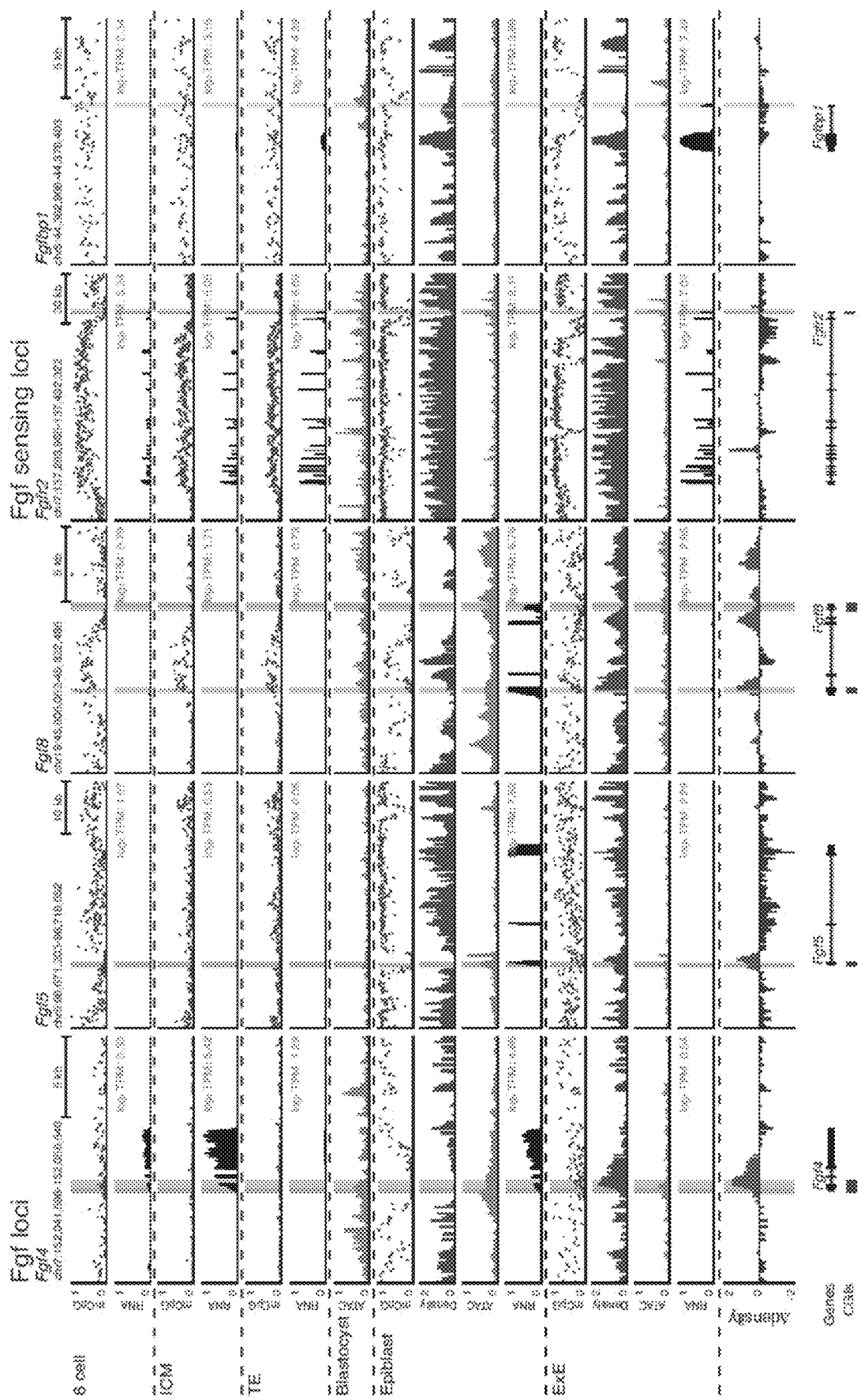
FIGS. 9A-9C demonstrate epigenetic restriction of FGF production and sensing to embryonic or extraembryonic compartments.
Figures 9B, 9C:
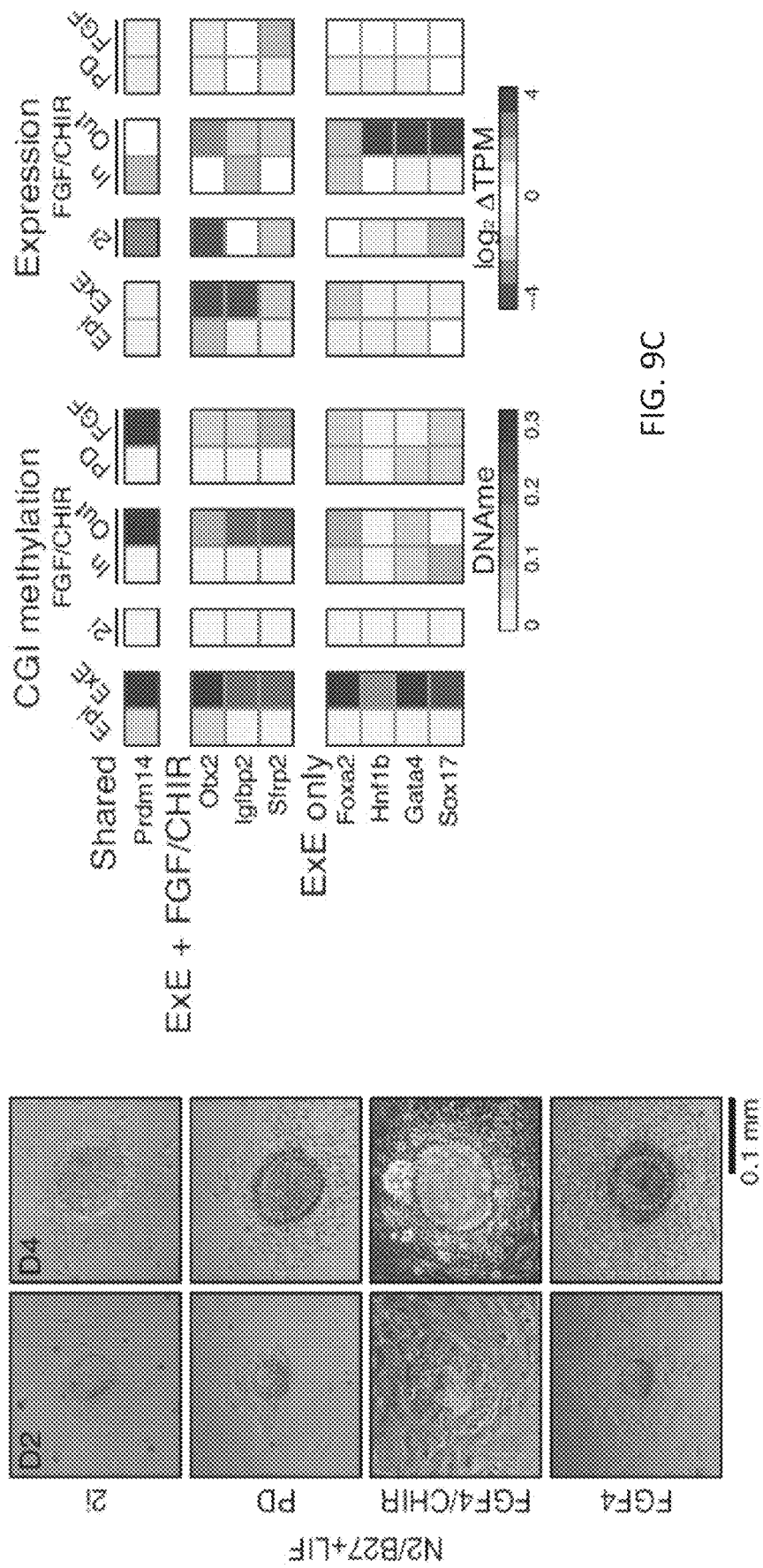

Suppression overlaps with WNT pathway effectors that are induced in the proximal epiblast to promote primitive streak formation (FIG. 2A). However, the ExE expresses alternative WNT proteins, suppresses fibroblast growth factor (Fe promoters by de novo methylation, and specifically expresses receptors for epiblast-secreted factors (FIG. 2B, FIG. 9A). The extraembryonic landscape may proceed deterministically from these two major signaling pathways, which are used promiscuously in many downstream developmental processes and frequently misregulated in cancers. To investigate this hypothesis, the ICM was selected as a model because it is indistinguishably hypomethylated from the trophectoderm and can be cultured independently of FGFs, whereas extraembryonic development rapidly attenuates[15]. ICMs were cultured in four conditions using combinations of FGF4, the mitogen-activated protein kinase kinase (MAPKK or MEK) inhibitor PD0325901, and the GSK3β inhibitor, WNT agonist CHIR99021 (CHIR) (FIG. 2C, FIG. 9B). Isolated outgrowths were dually assayed by a combined RNA-seq and reduced representation bisulfite sequencing (RRBS) approach (FIG. 10, Methods). Those cultured in FGF4 plus CHIR progressively diverged into two separate, morphologically distinguishable interior and exterior tissues that were independently isolated.

Figure 2F:
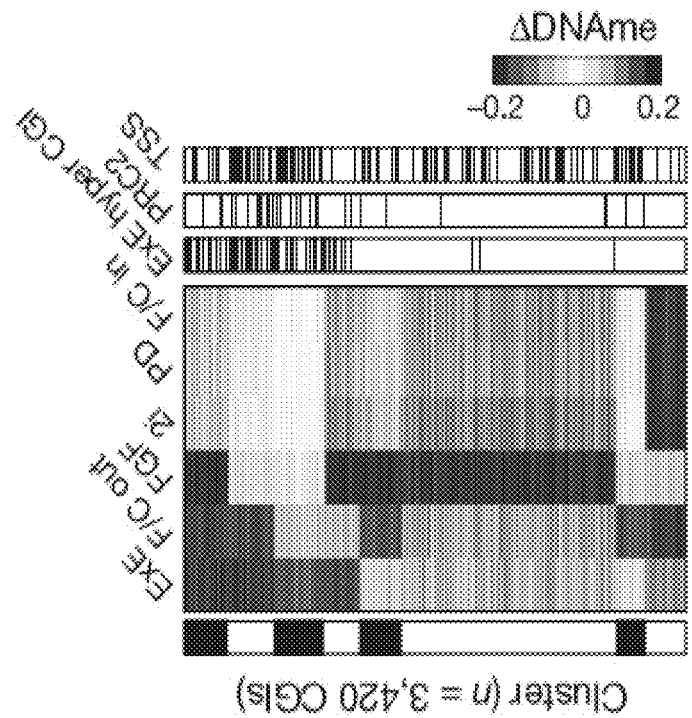
Figure 2E:
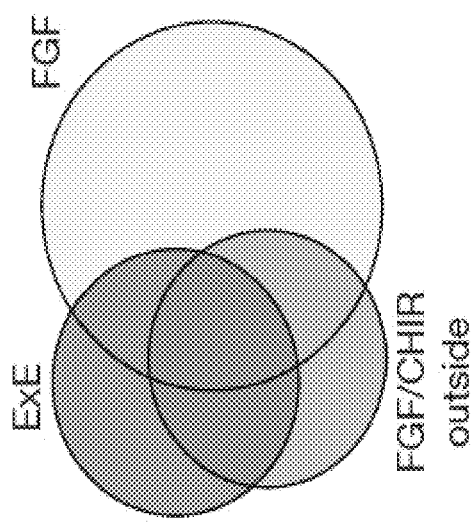

In combination, PD0325901 and CHIR comprise the '2i' condition, an FGF-impeded, WNT-activated state that maintains preimplantation like global hypomethylation[16]. Alternatively, exogenous FGF is sufficient to drive genome and CGI methylation to higher than physiological levels (FIG. 2D). Surprisingly, when coupled with FGF, WNT agonism effectively blocks genome remethylation but redirects CGI-level methylation to a greater subset of extraembryonic targets (FIGS. 2E-2F). CGI-targeting is specific to the FGF plus CHIR outgrowth exterior, which establishes an asymmetric Fgfr2 and Fgf4 expression pattern with the interior, similar to what occurs in vivo. The specific overlap between in vitro and ExE-methylated CGI promoters appears to reflect progressive restriction of potential targets over early development: those shared across conditions have early developmental functions and are often expressed in the ICM and the 2i condition such as Prdm14; those methylated in the ExE and in FGF plus CHIR, but not in FGF alone, generally encompass neuroectodermal regulators such as Otx2 and Pax6; and ExE-exclusive targets are often endodermal and induced by dual FGF and WNT activity such as FoxA2 and Sox17 (FIG. 9C). Seemingly, ExE-like global hypomethylation and CGI methylation can be recapitulated in vitro by WNT and FGF, but target specificity can be modulated to include multiple discrete developmental programmes.

Figure 3D:
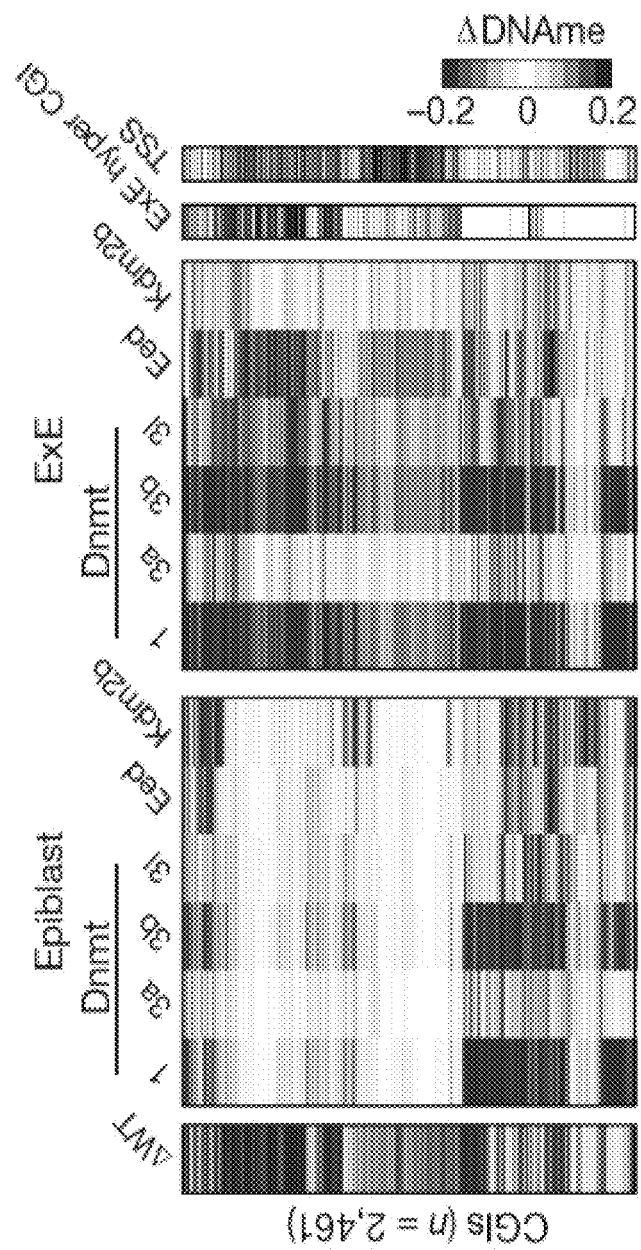
Figures 11A, 11B, 11C, 11D, 11E:
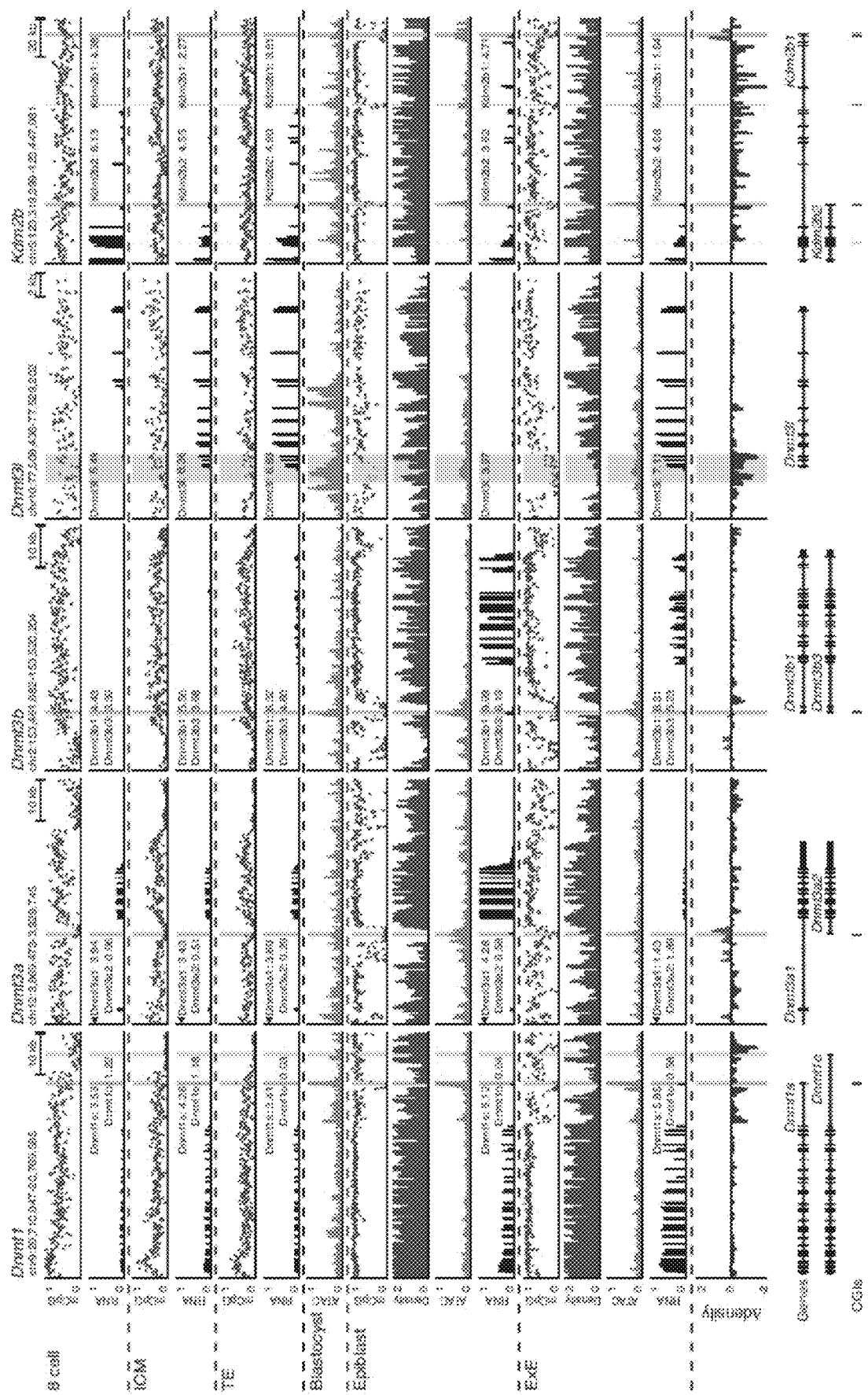
Figure 11F:
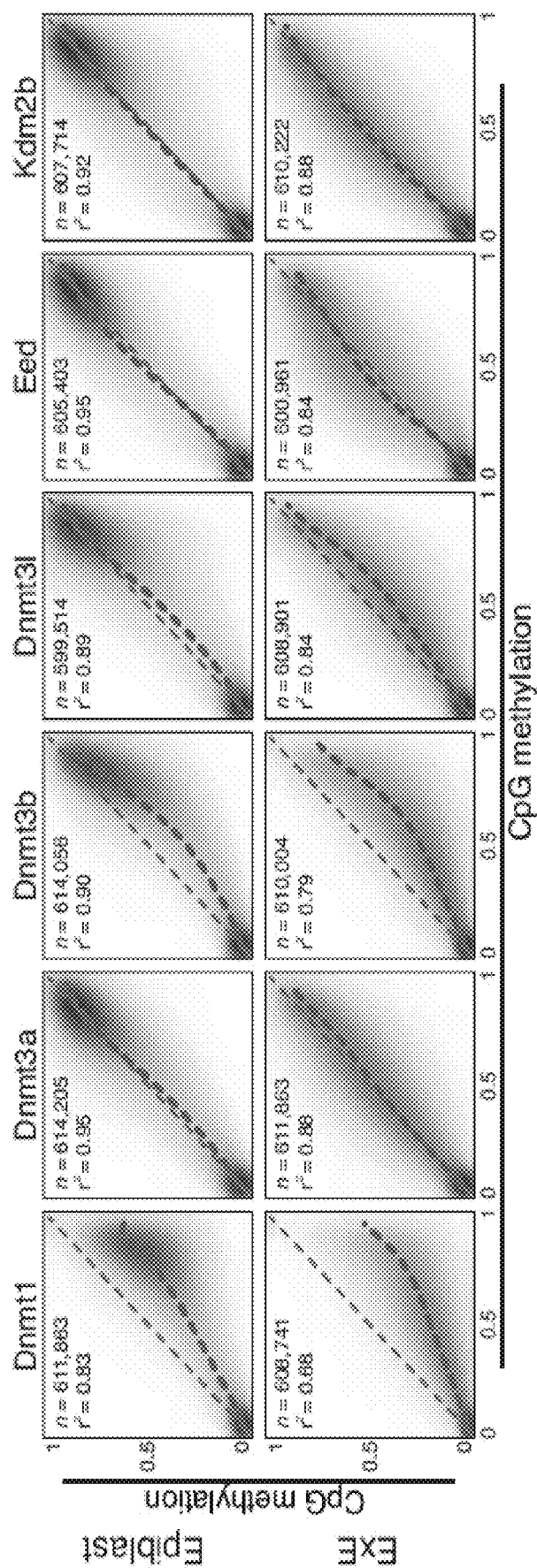
Figure 12A:
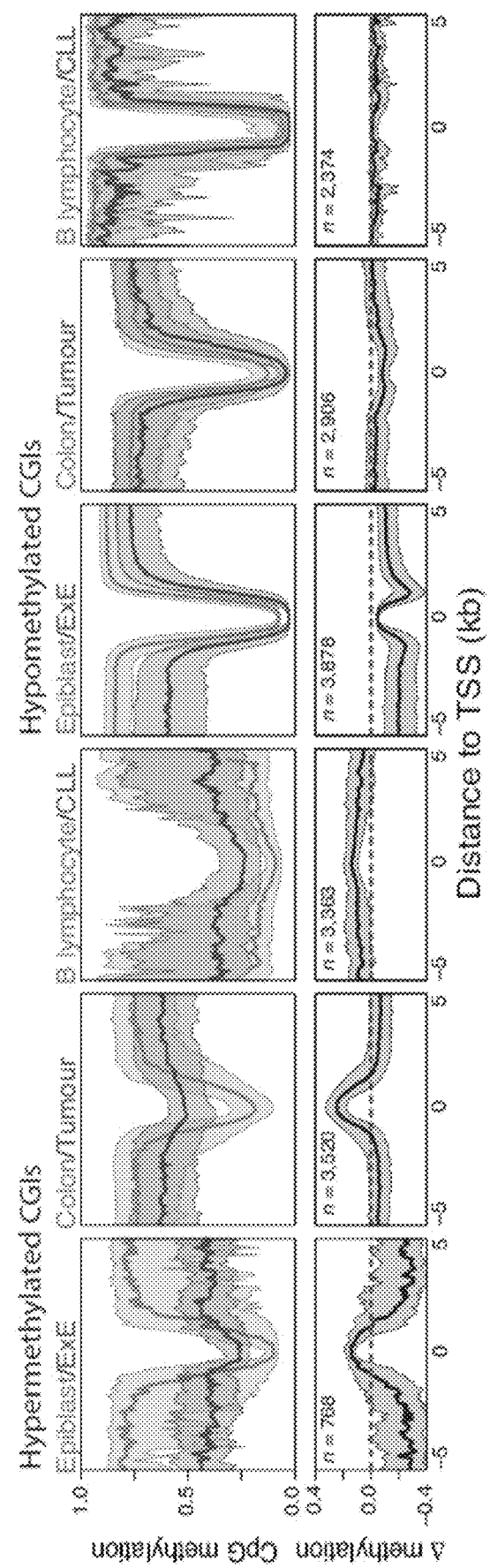
FIGS. 12A-12F demonstrate general features of the cancer methylome and of CGI DMRs.
Figure 12B:
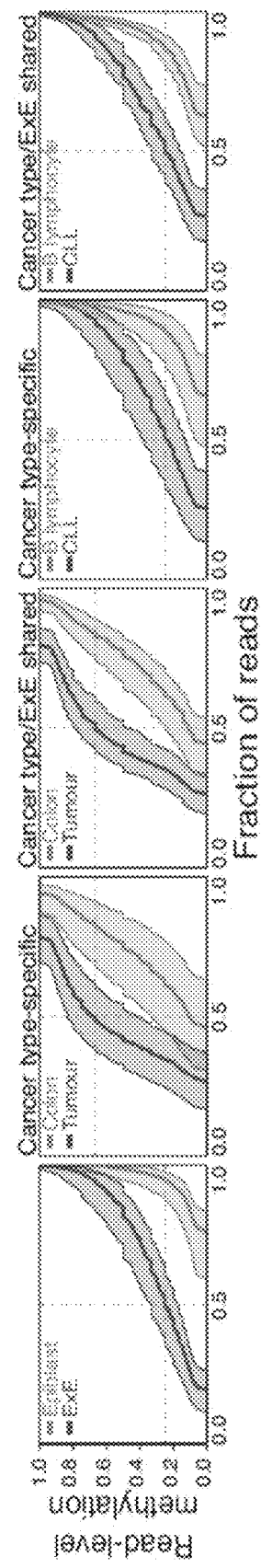
Figure 12C:
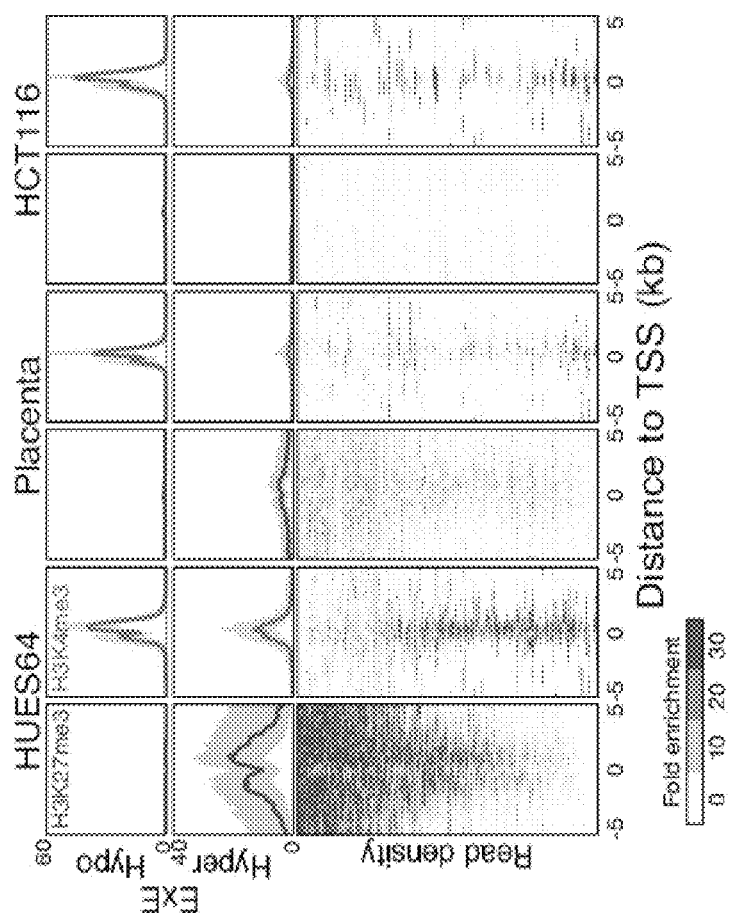
Figure 12D:
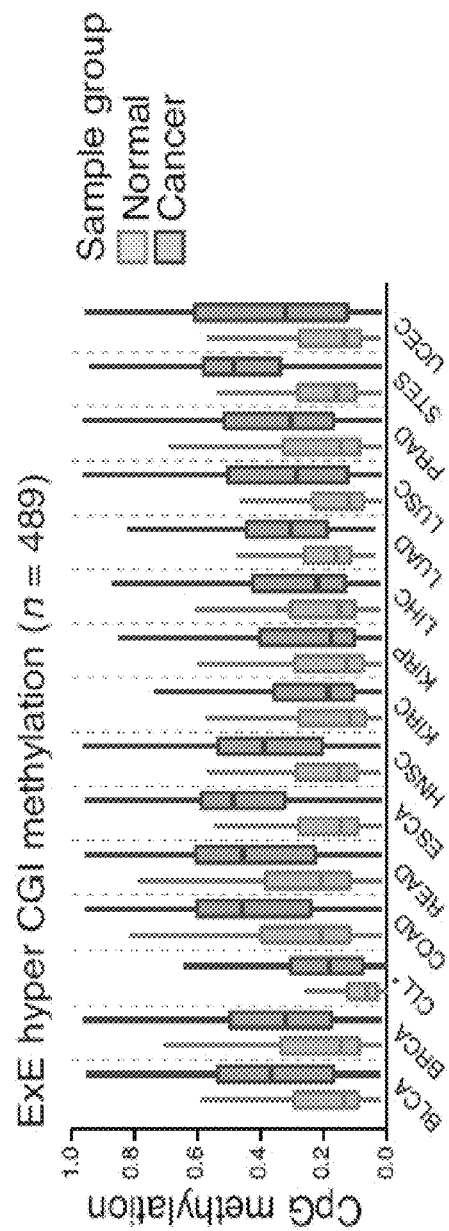
Figure 12E:
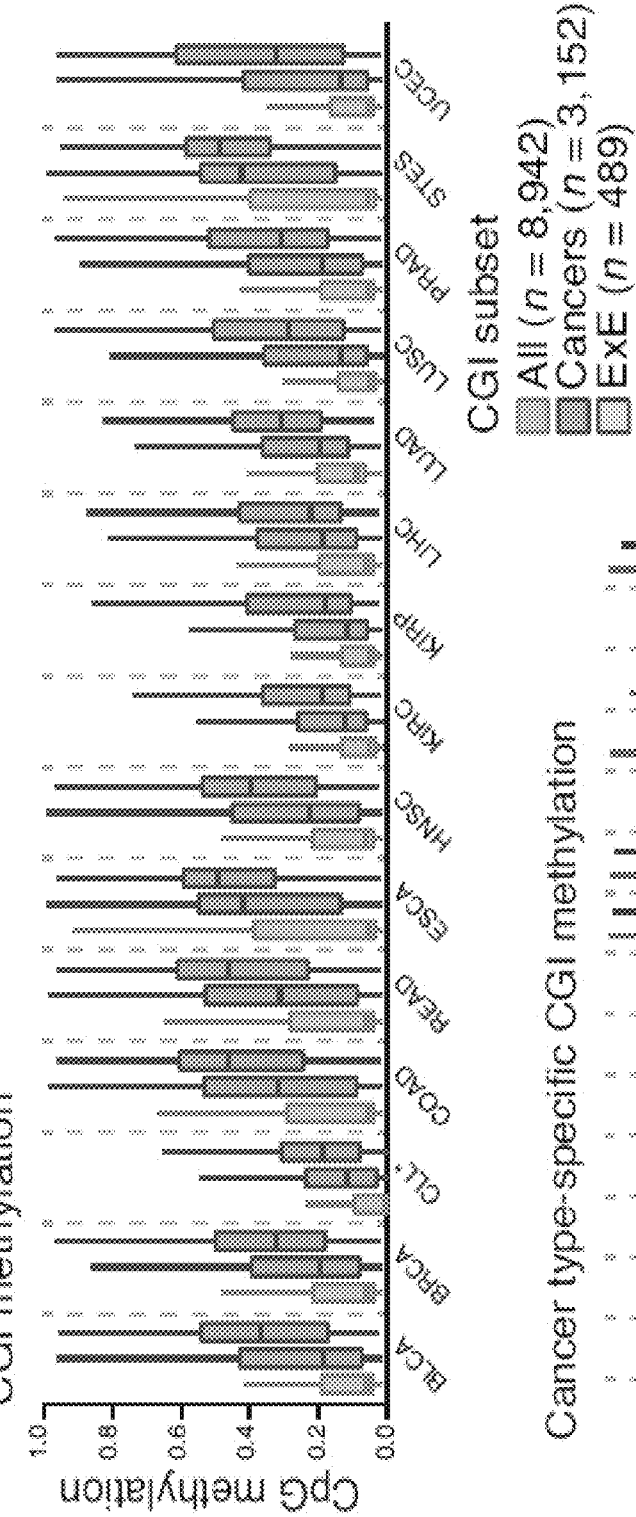
Figure 12F:
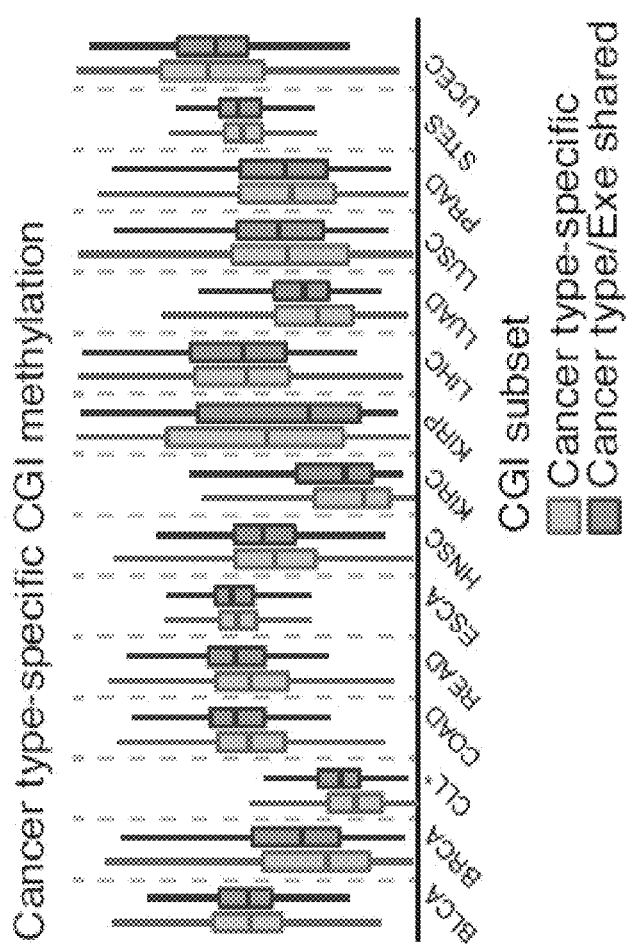

The configuration of epigenetic regulators that specifically execute this transition was next investigated. Whereas Dnmt1 and Dnmt3b are expressed in both tissues, Dnmt3l and Dnmt3a isoform 2 are reciprocally expressed in either the ExE or the epiblast and regulated by de novo promoter methylation in the other (FIGS. 11A-11D). A truncated, non-catalytic isoform of the histone 3 lysine 36 (H3K36) demethylase Kdm2b is expressed during preimplantation and within the ExE, whereas a longer Jumonji demethylase domain containing isoform is specifically induced in the epiblast" (FIG. 11E). Otherwise, epigenetic regulator expression appears relatively stable between the two tissues at this time, such that their specific integration could explain the assembly of such profoundly different landscapes. To compare their capacity to direct both global and CGI methylation, we acutely disrupted Dnmt1, Dnmt3a, Dnmt3b, and Dnmt3l, the essential PRC2 component Eed, and Kdm2b by zygotic CRISPR-Cas9 injection (Methods). We found that Dnmt1, Dnmt3b, and Dnmt3l ablation substantially disrupt the ExE methylome, including at CGI targets, but show no obvious specificity for these regions or corresponding changes in expression (FIGS. 3A-3B, FIGS. 11F-11H). The near complete loss of methylation in Dnmt1-null ExE compared to sample-matched epiblast indicates diminished de novo activity, and greater reliance on epigenetic maintenance, despite prolonged Dnmt3l expression (FIGS. 3A-3B). Alternatively, Eed-null ExE disrupts CGI methylation without affecting global levels, suggesting that PRC2 may specifically coordinate repression upstream of DNMT3B as part of a novel developmental pathway (FIGS. 3B-3D, FIGS. 11F-11G). Consistently, Eed-null ExE fails to suppress associated genes, which are induced to similar levels to those of the sample-matched epiblast (FIG. 11H).

Figure 4E:
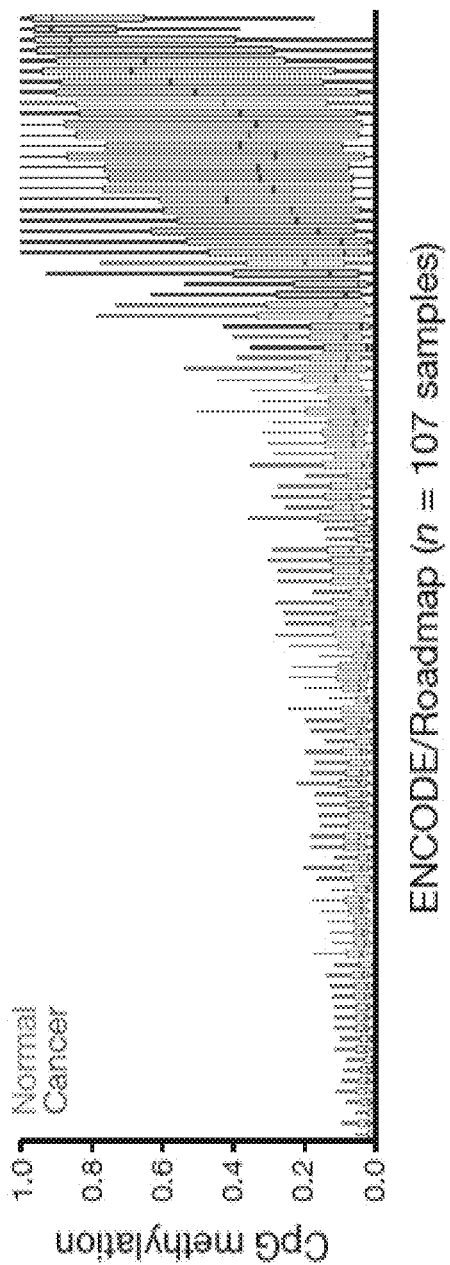
Figures 5A, 5B:
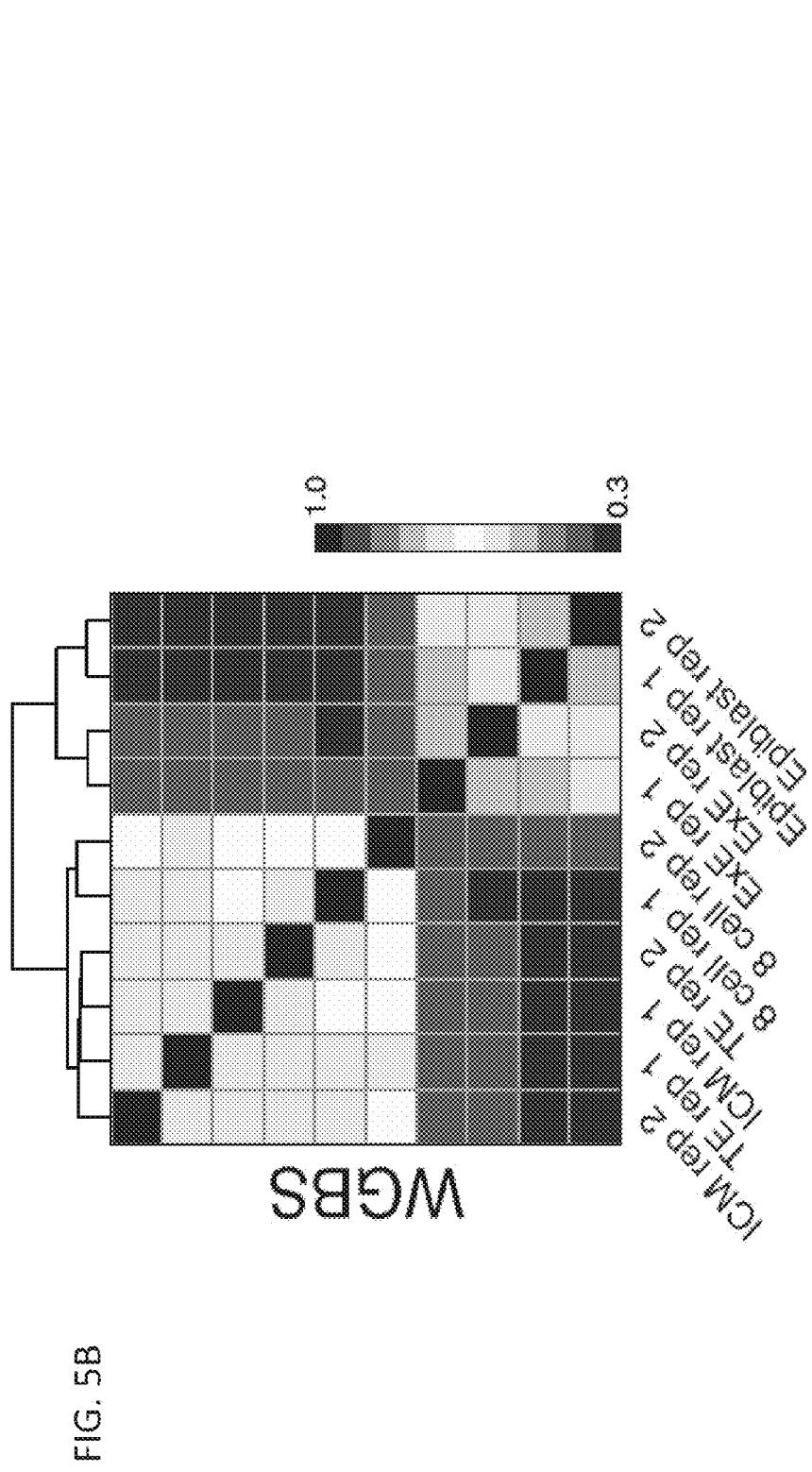
FIGS. 5A-5G demonstrate tracking divergence in DNA methylation landscapes during mouse implantation.
Figures 5C, 5D:
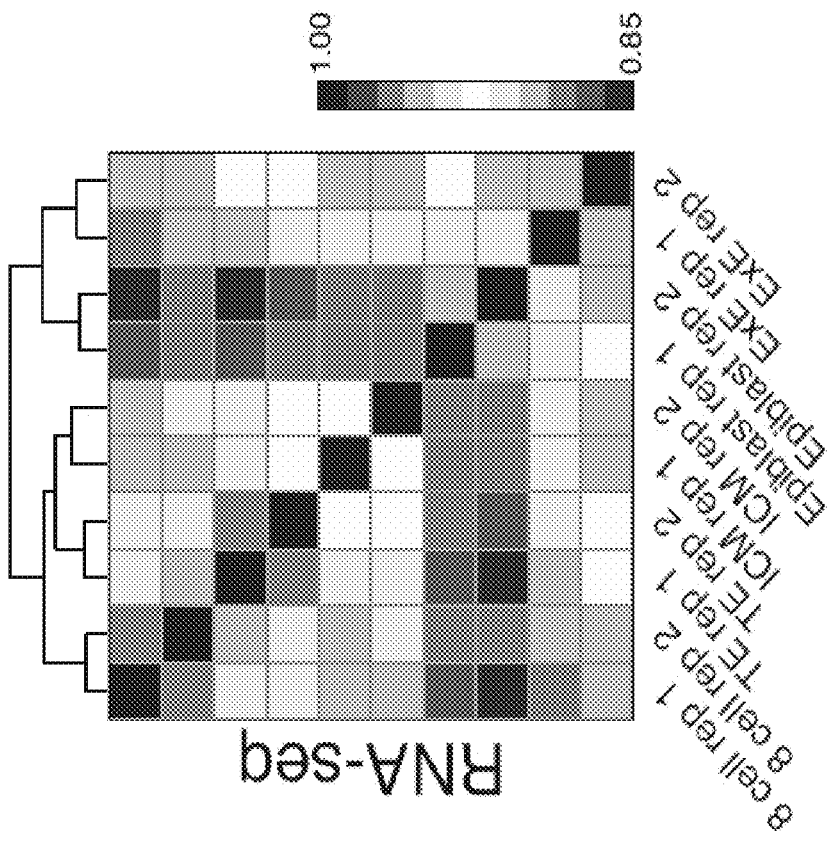
Figures 5E, 5F:
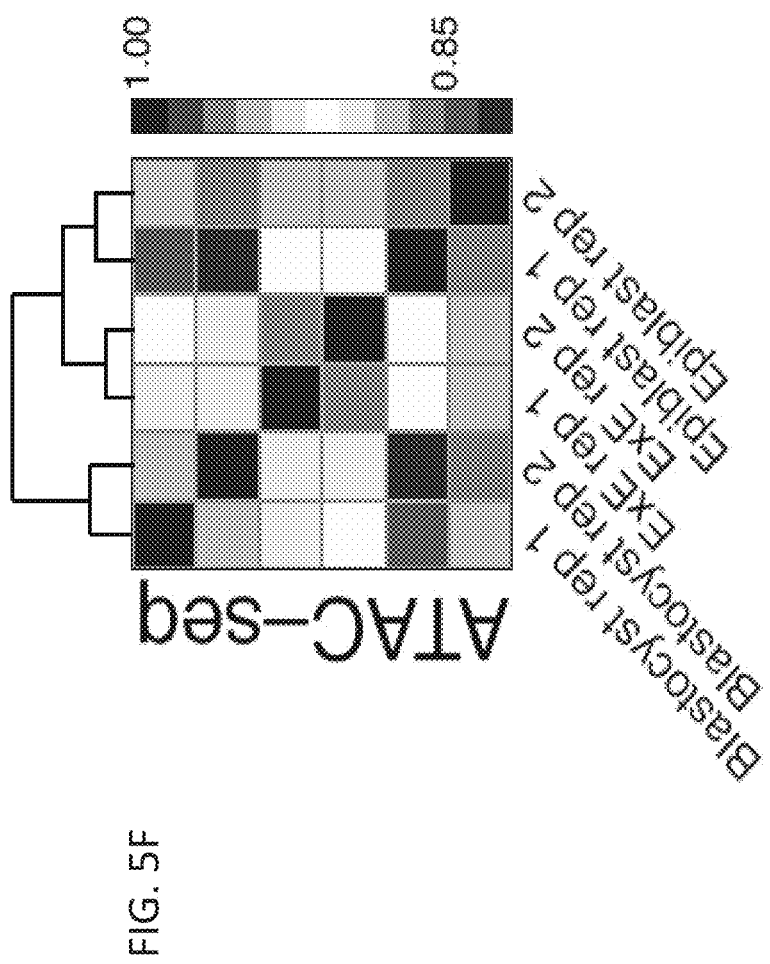
Figure 5G:
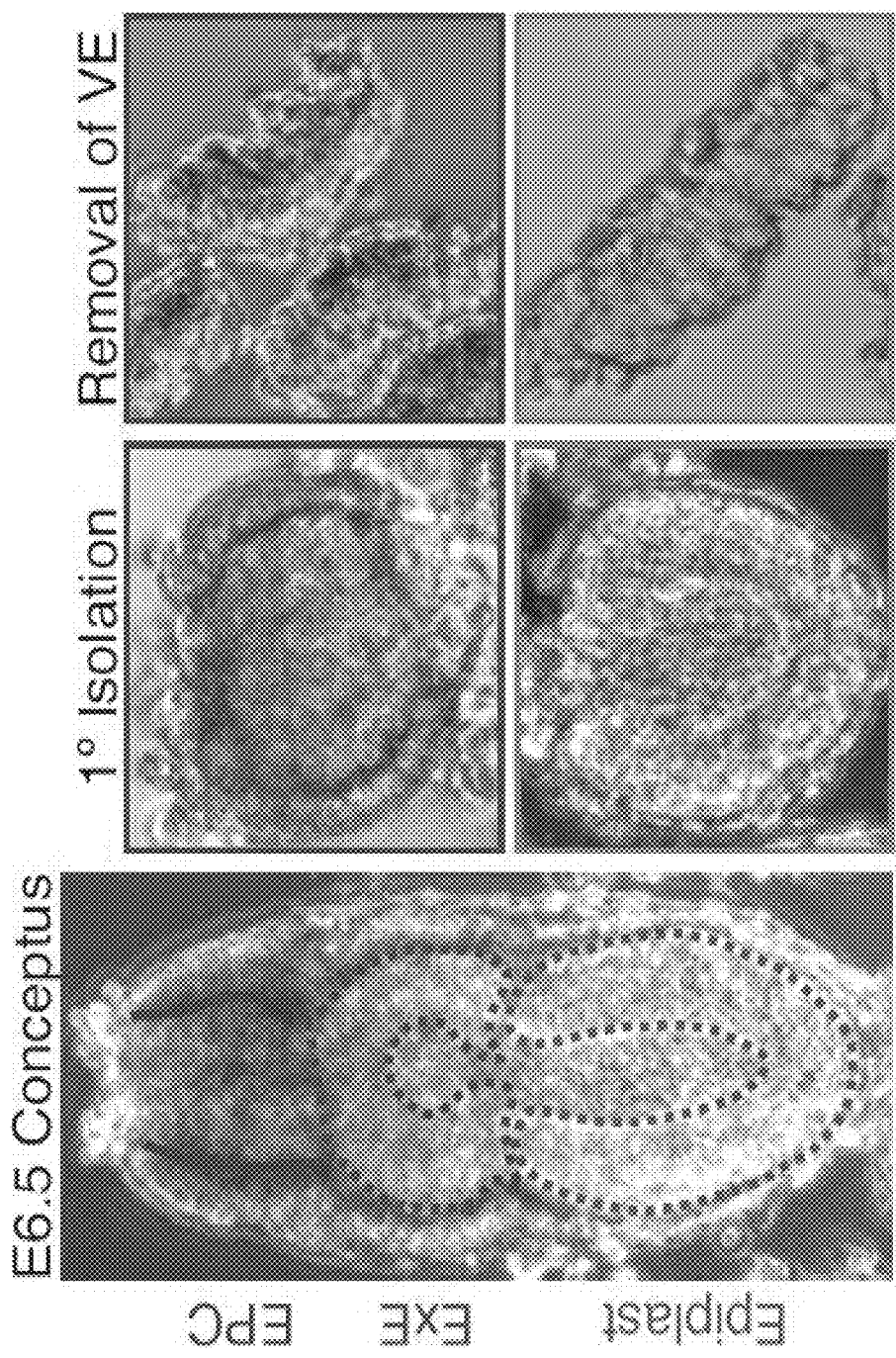
Figure 13A:
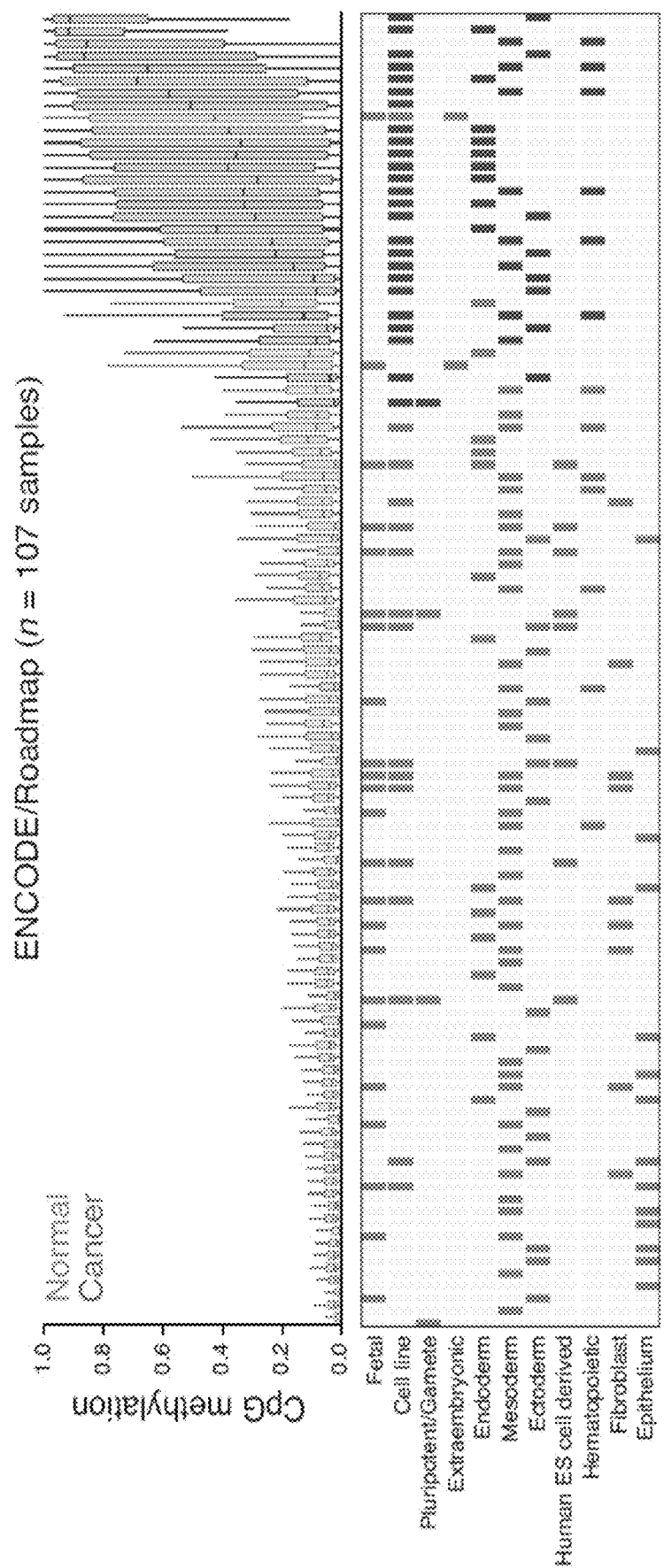
FIG. 13A includes additional sample characteristics.
Figure 13B:
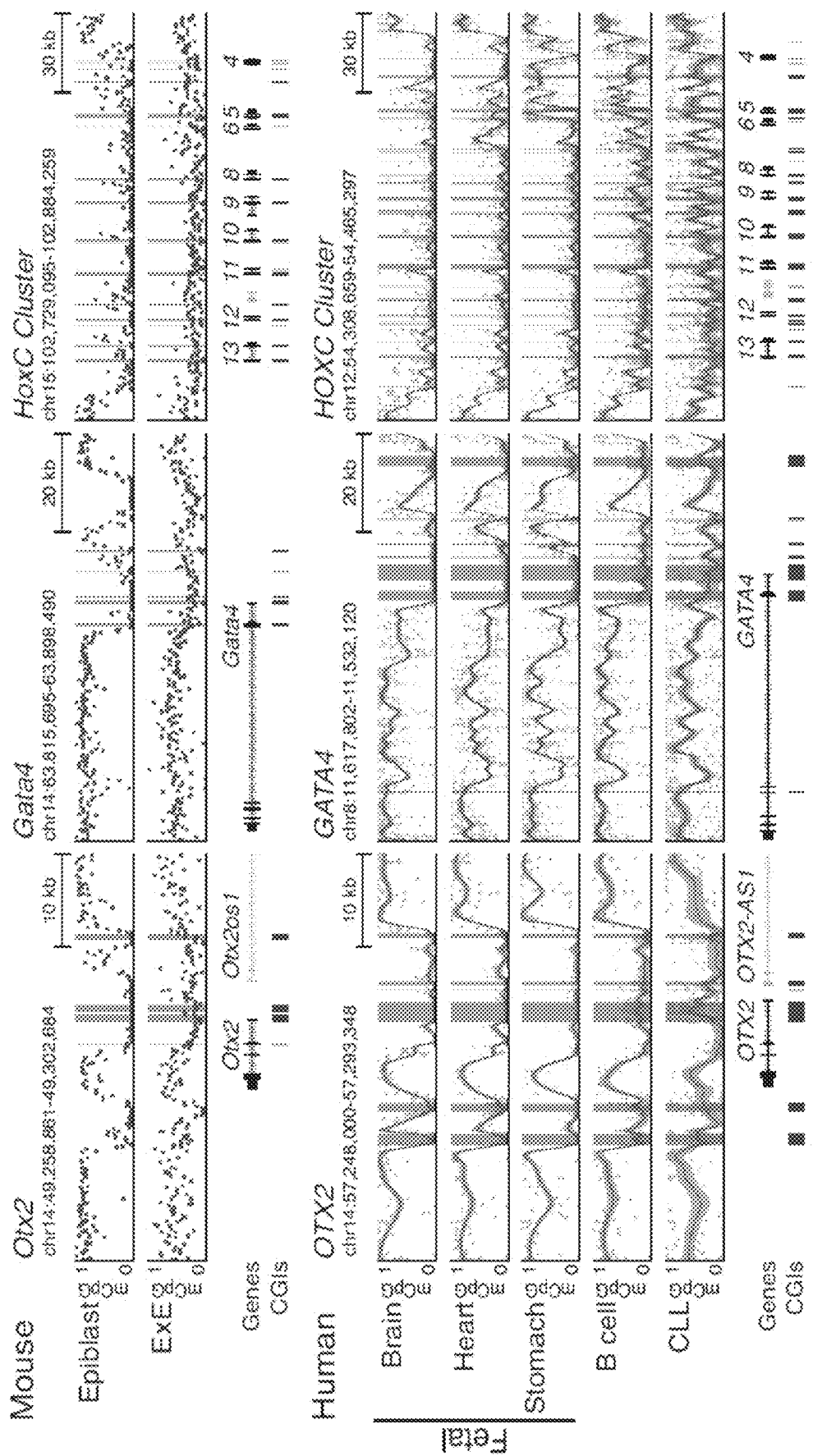
Figure 14A:
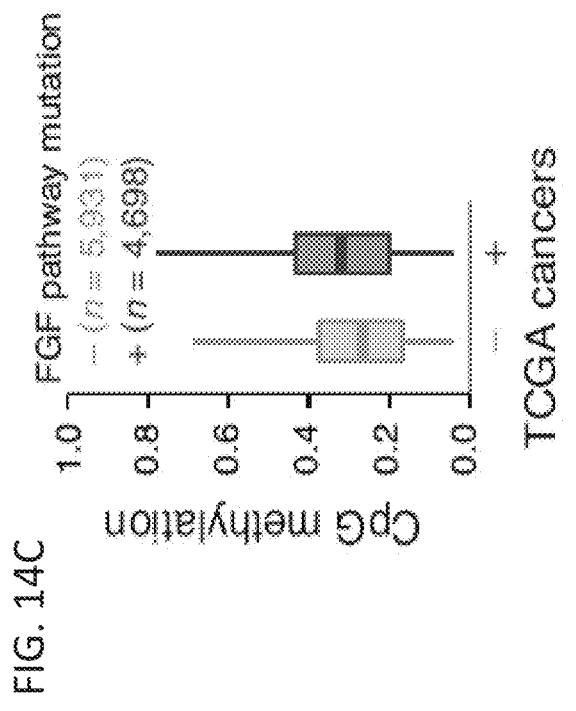
FIGS. 14A-14F demonstrate genetic features of ExE CGI methylation in cancers.
Figure 14B:
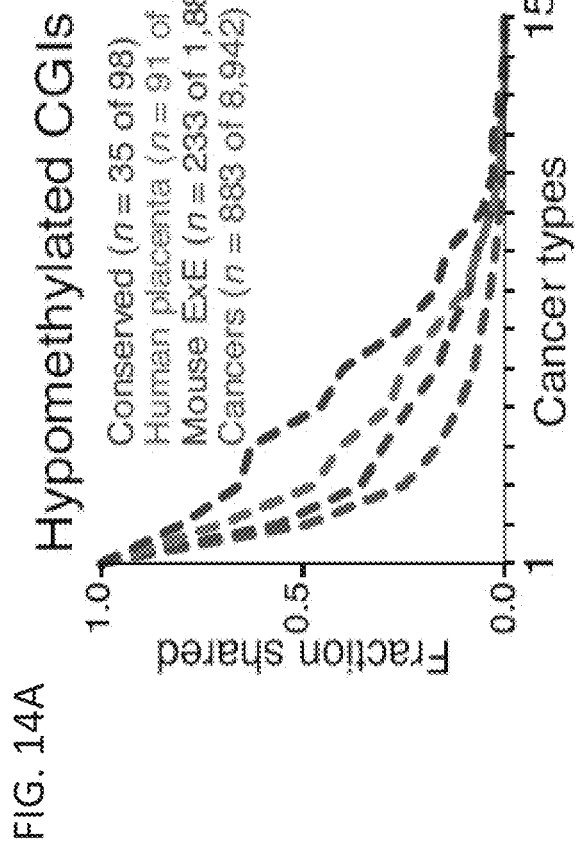
Figure 14C:
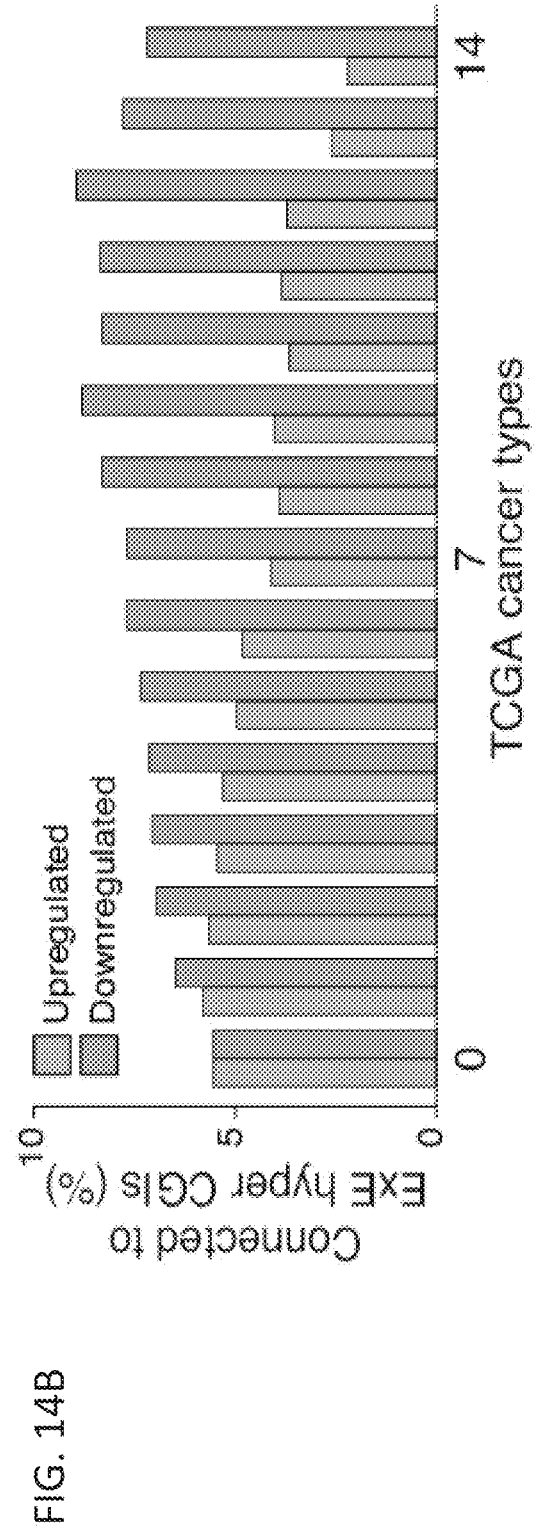
Figure 14D:
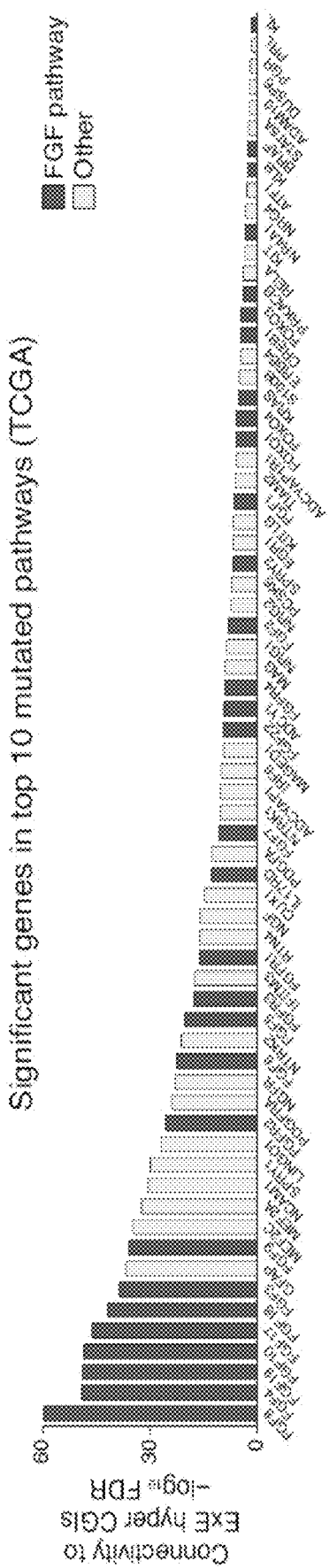
Figure 14E:
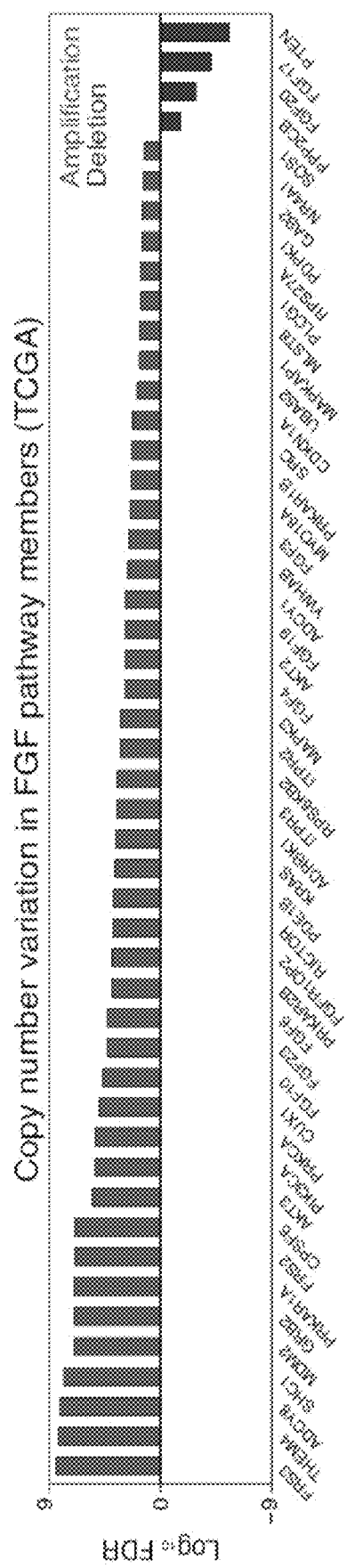

The data indicates a point in early development at which sensitivity to promiscuously used growth factors instructs a distinct epigenome that is not observed during downstream ontogeny. However, de novo CGI methylation is also a general feature of tissue culture, cancer cell lines, and primary tumours, indicating a latent vulnerability in somatic cells[5,18] (FIG. 4, FIGS. 12-13). To investigate a possible link with the subsequent re-emergence of this landscape in cancer, orthologous CGIs were mapped to compare patient-matched DNA methylation profiles from The Cancer Genome Atlas (TCGA) project, an age-matched chronic lymphocytic leukaemia (CLL) cohort, as well as data from the Encyclopedia of DNA Elements (ENCODE) and the Roadmap Epigenomics Project[14,19-21]. Of the 16 cancer types with sufficient normal biopsied samples, 15 significantly methylate ExE hyper CGIs (FIGS. 4A-4B). The signal is surprisingly robust and segregates cancer and normal tissue when measured as a feature across patients or when examining CGI-level changes (FIG. 4B, FIG. 12). 84% of ExE hyper CGIs are methylated in at least one cancer type, and they are more frequently shared as conserved, pan-cancer targets (FIGS. 4C-4D, FIGS. 14A-14B). Some direct and indirect evidence was found that CGI methylation can be influenced by FGF sensing. For example, matched mutational and methylation analyses of the entire TCGA dataset (n=10,629 cancers) show a 19.3% increase in the average methylation of ExE hyper CGIs when any FGF pathway member is mutated (from 0.275 to 0.328, FIG. 14C). Similarly, statistical assessment of the connectivity between the ExE hyper CGIs and the 10 most mutated pathways in cancer reveals a notable enrichment for FGFR signaling in disease (enrichment z-score=3.88, FIGS. 14D-14E). Over the more expansive, but less internally controlled, ENCODE and Roadmap data, cancers and immortalized cell lines are clearly separated from primary tissues by their ExE hyper CGI methylation status (FIG. 4E). Notably, mature adaptive immune cells and endodermal lineages are generally more susceptible to low-level methylation within these regions, suggesting a pre-existing heterogeneity even in normal populations.

Figure 14F:
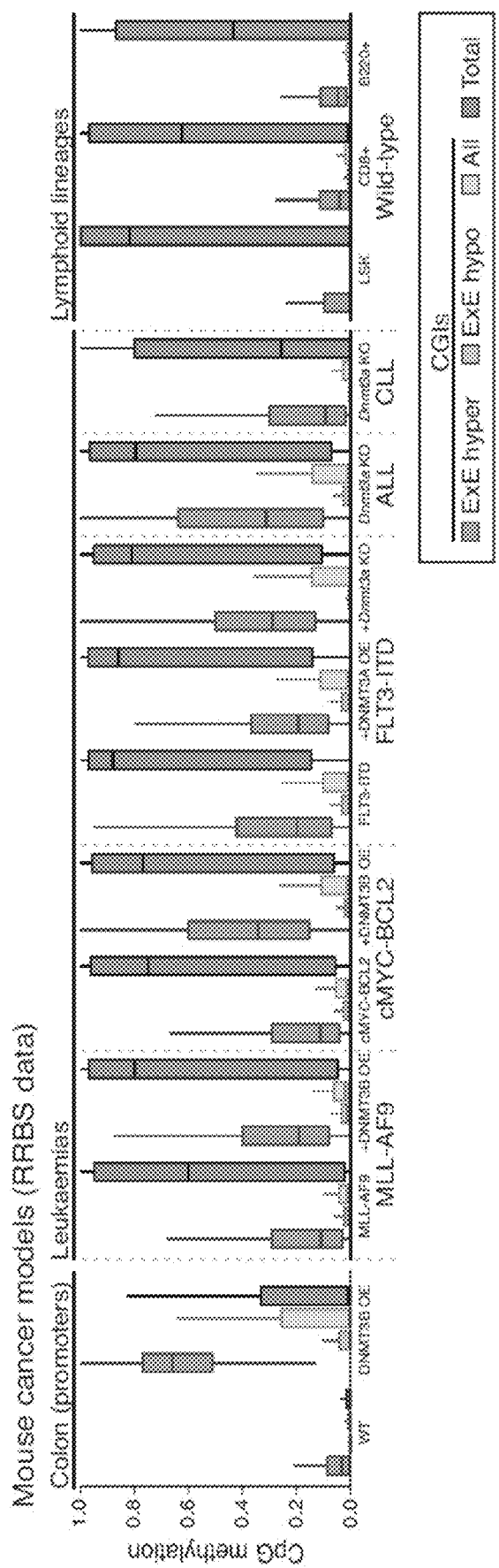

The developmental acquisition of an epigenetic landscape that partitions extraembryonic tissues within the embryo human cancers is presented. This landscape co-occurs with the establishment of the first major signaling axes, can be partially directed from the hypomethylated ICM in vitro, and appears to be determined by disparate regulation of the DNMTs and associated cofactors. Notably, de novo methylation of CGIs in the ExE requires PRC2, which indicates a transient, biochemical interaction with DNMT3B or an upstream role in either determining the ExE state or priming CGIs for suppression. The coordination of this alternative, and presumably more permanent, repressive mechanism warrants further investigation and shares features with the somatic transition to cancer. Most obviously, FGF sensing passes through RAS/MAPK/ERK signaling, which has extensive oncogenic potential and putative roles in the establishment of the cancer methylome[22-24]. Similarly, the ExE displays attenuated de novo methylation activity directed wholly by DNMT3B, broadly resembling the high frequency of somatic DNMT3A mutations in acute myeloid leukemia and myelodysplastic syndrome or DNMT3B-directed CGI methylation during colorectal transformation[25-28]. Transgenic mouse cancer models confirm conserved ExE hyper CGI methylation in similar contexts (FIG. 14F). The extraembryonic landscape depends on extrinsic cues with numerous downstream developmental functions, which may provide a latent opportunity for spontaneous state transition without genetic perturbation in later development. If so, the likelihood of such a transition may relate to how closely a given regulatory network resembles the one governing extraembryonic specification. Whether or not additional morphological and molecular features of placental development that appear analogous to cancer hallmarks[29,30]—such as immunosuppression, tissue invasion, and angiogenesis—proceed as part or downstream of this primary epigenetic switch remains unexplored, but would provide a parsimonious developmental foundation for their systematic emergence during transformation.

Additional details and supplemental information are provided in Smith et al., "Epigenetic restriction of extraembryonic lineages mirrors the somatic transition to cancer" *Nature* 549, 543-547 (28 Sep. 2017), incorporated herein by reference in its entirety, including the extended data and supplementary information.

Example 2: Haplotype-Level Methylation Significantly Reduces Background Noise in Normal Cells It has recently been demonstrated that disordered methylation is frequently observed in cancer. This is one of the reasons why single CpG-based diagnosis has low sensitivity because methylation may occur in nearby CpG sites. For example, the overall sensitivity of single CpG-based diagnosis is only 60% for SEPT9 in colorectal cancer. Moreover, diagnosis of early cancers (with <0.1% ctDNA) requires nearly zero background. However, normal cells acquire low-level methylation (~1%) due to stochastic processes when measured at single CpG sites.

It was found that DNA methylation haplotypes provide a better choice for diagnosis purposes. Here, a haplotype refers to a combination of CpG sites found on the same chromosome. Similarly, a DNA methylation haplotype represents the DNA methylation status of CpG sites on the same chromosome. In bulk bisulfate sequencing, DNA methylation status of thousands/millions of cells was measured. Though fragments of DNA were sequenced, every single fragment is guaranteed to come from a single chromosome and a single cell. Thus, the methylation pattern of CpGs on each fragment represents a single DNA methylation haplotype.

Figures 15A, 15B, 15C:
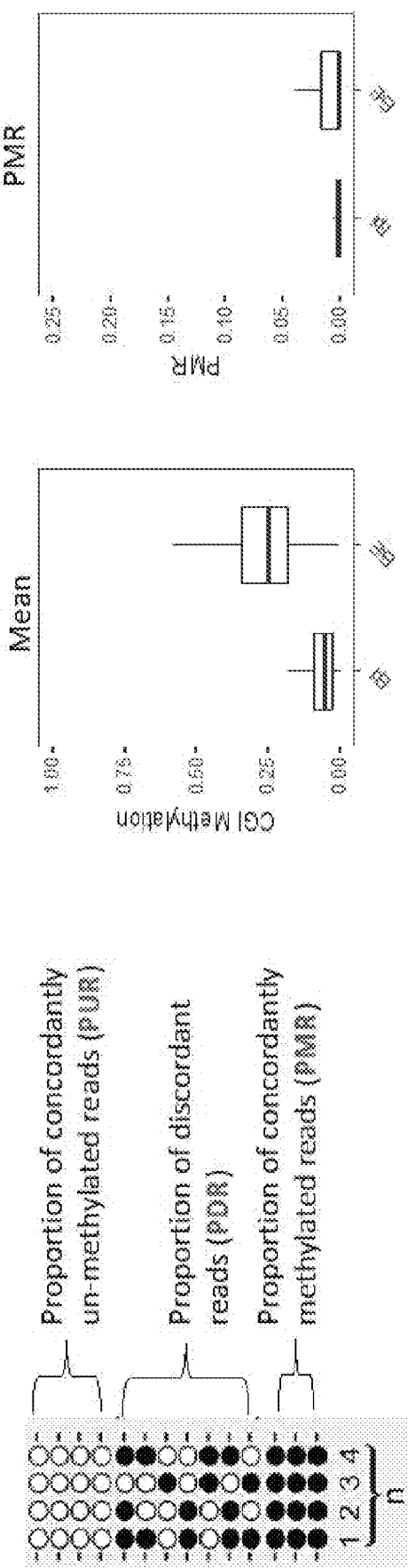
FIGS. 15A-15C demonstrate haplotype-level methylation increases signal-to-noise in circulating tumor DNA (ctDNA) detection.
Figure 16A:
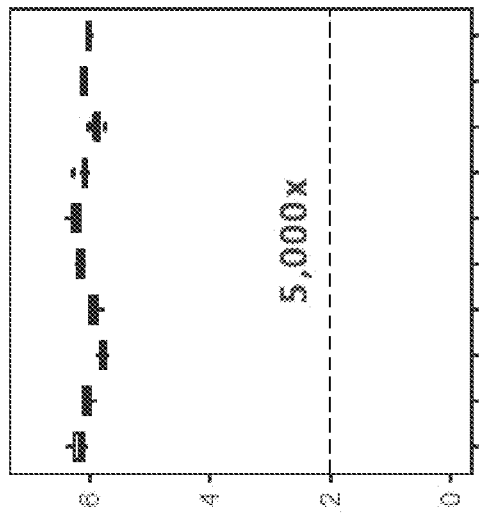
FIGS. 16A-16D demonstrate detection of low-frequency tumors (0.01%) from cell free DNA (cfDNA) through simulation. Sequencing reads were simulated from tumor-like ExE tissue and normal-like Epi tissue. To detect ctDNA in early cancer patients, the fraction of tumor-like reads covers 1% (FIG. 16A), 0.1% (FIG. 16B), and 0.01% (FIG. 16C). Negative controls were also included, in which no tumor-like reads were simulated (FIG. 16D). Rank sum test-based detection p-values were shown in Y-axis. Coverages of simulation were shown in each panel, which guarantees 5× coverage of tumor-like DNA.
Figure 16B:
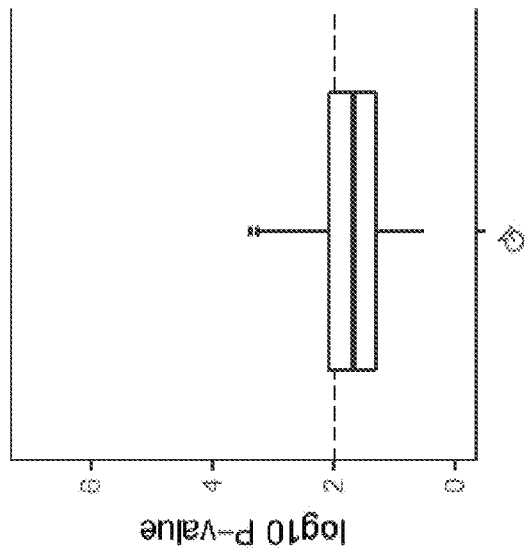
Figure 16C:
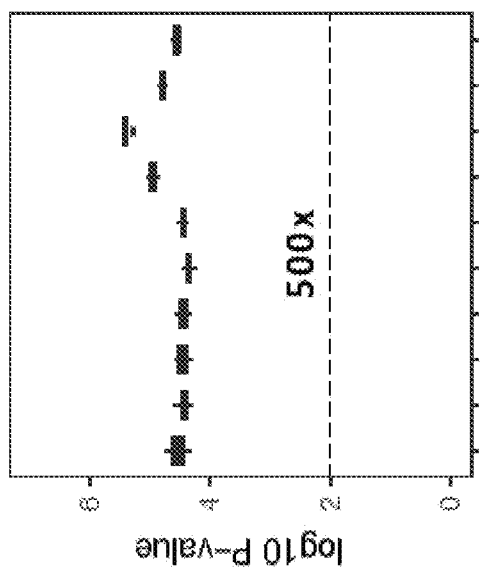
Figure 16D:
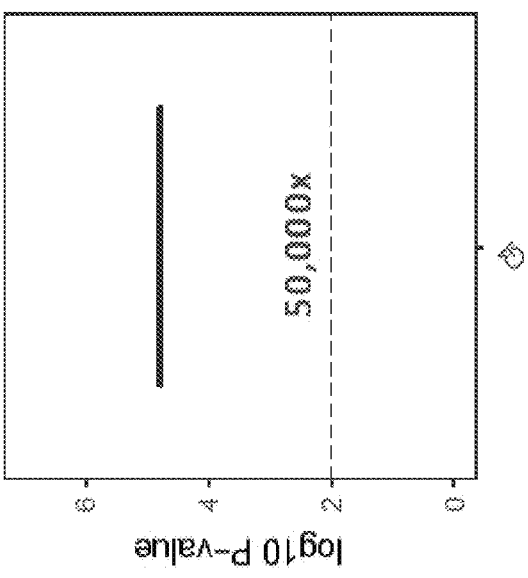
Figure 17A:
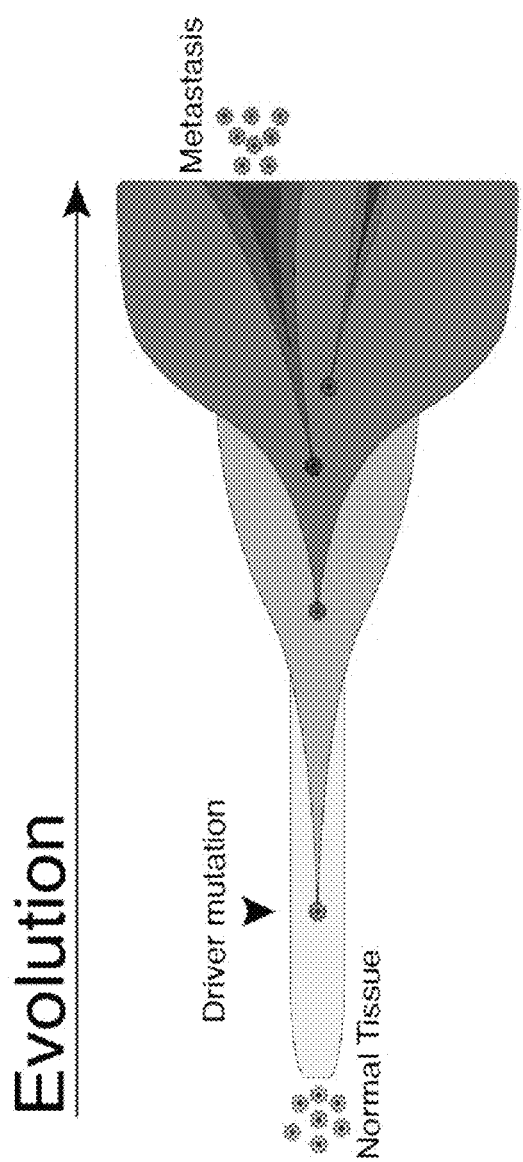
FIGS. 17A-17B provide a genetic model of cancer.
Figure 17B:
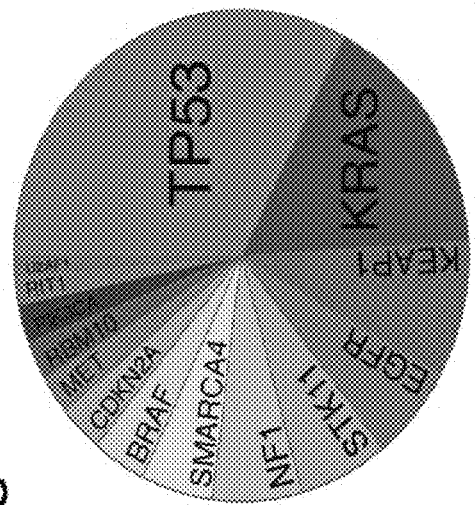
Figures 18A, 18B:
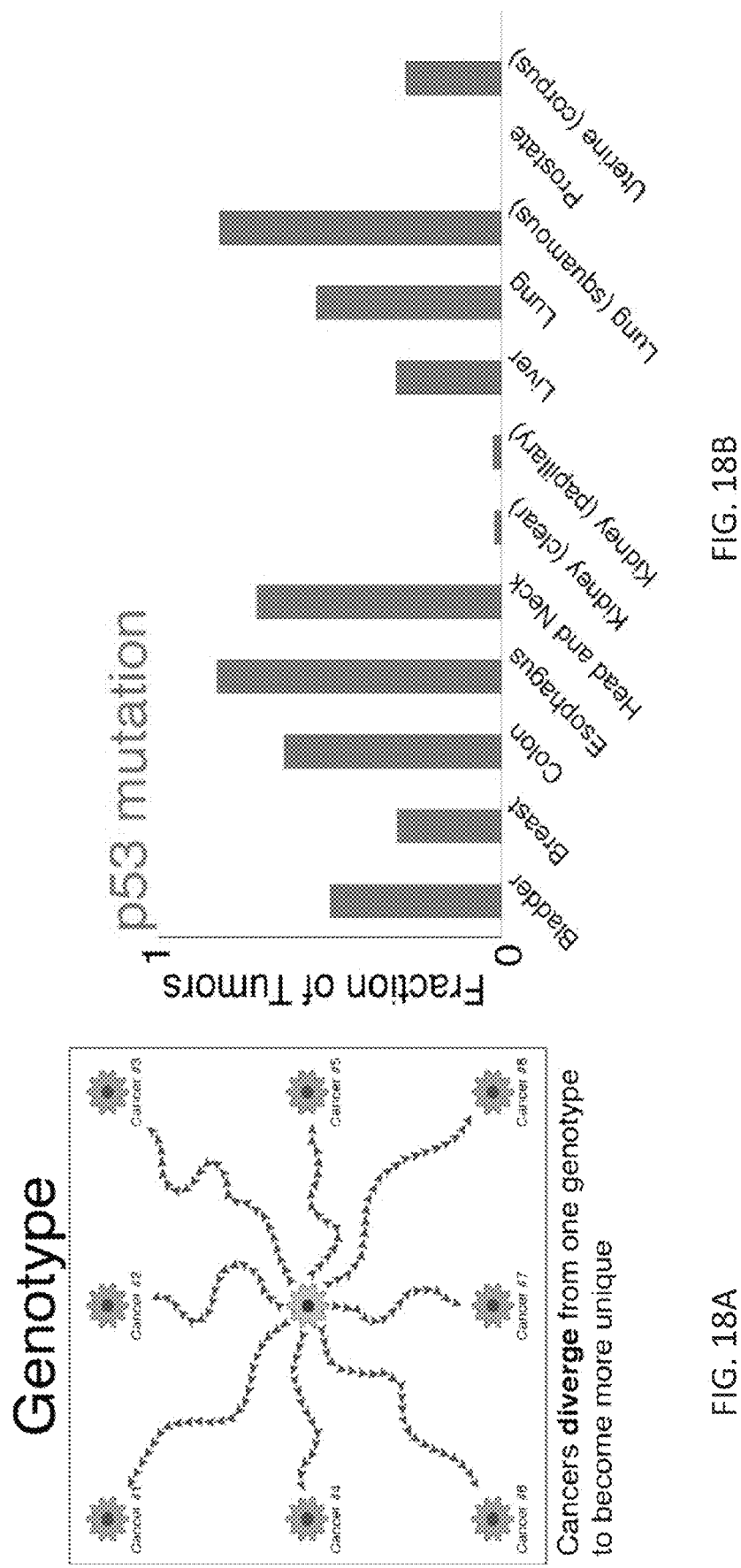
FIGS. 18A-18D demonstrate a developmental framework for universal cancer diagnosis using a methylation signature. Cancer cells may diverge from one genotype to become more unique (FIG. 18A). As an example, a p53 mutation may be detectable in a varying fraction of tumors over a number of cancer types (FIG. 18B). Cancer cells will converge in a stepwise fashion towards a common state (FIG. 18C). A methylation signature may be detectable in a large fraction of tumors for a variety of cancer types (FIG. 18D).
Figures 18C, 18D:
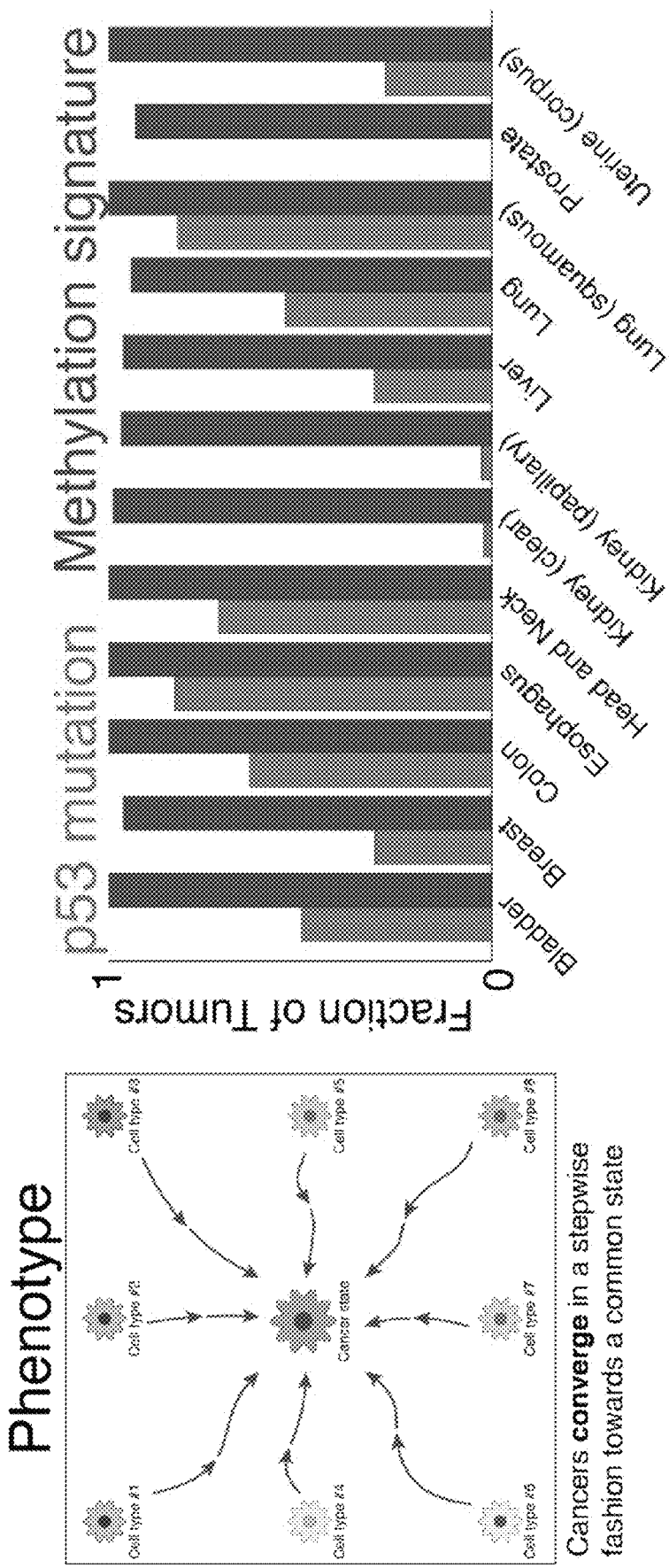
Figure 19:
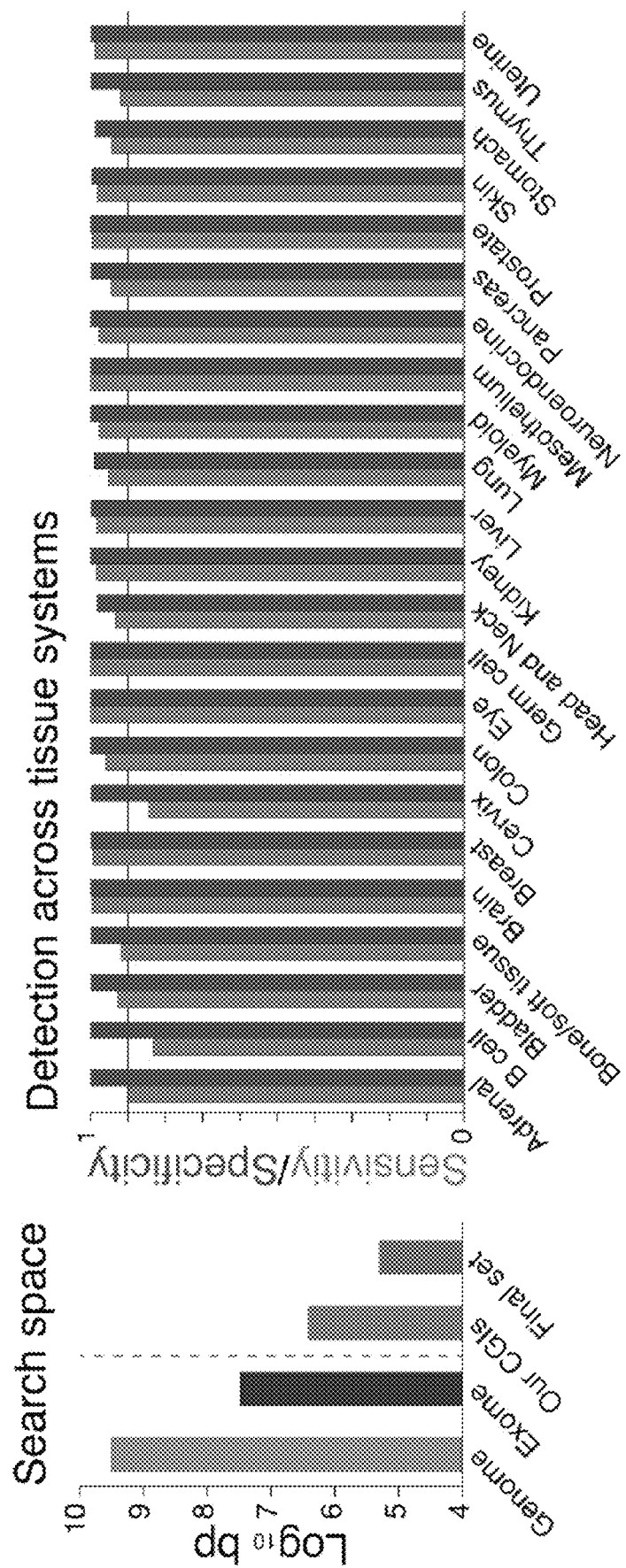
FIG. 19 shows precise molecular detection for predicting cancer tissues of origin using a novel methylation signature. The search space is identified (left panel) and detection of sensitivity/specificity across tissue systems using a novel methylation signature is provided (right panel).

For example, as shown in FIG. 15A, for a locus with 4 CpG sites, if it is determined that 14 reads cover this locus, then it was stated that 14 DNA methylation haplotypes were observed. Traditionally, only the aggregated methylation in these 4 sites is measured as a fraction of methylated CpGs divided by all CpGs measured (0.57, 0.43, 0.43 and 0.5 in this example) (FIG. 15A). In contrast, haplotypes were checked instead. Specifically, these haplotypes were classified into three groups, concordantly un-methylated haplotypes, disordered haplotypes and concordantly methylated haplotypes. Since next generation sequencing is usually applied for DNA methylation, sequencing reads and haplotypes were utilized interchangeably.

To normalize the total sequencing depth, the proportion of concordantly unmethylated reads (PUR), proportion of disordered reads (PDR) and proportion of concordantly methylated reads (PMR) was calculated. So PUR, PDR and PMR always range from 0 to 1, and PUR+PDR+PMR=1. Currently, PUR/PDR/PMR is calculated for regions with at least 4 CpG sites and covers at least 20×.

PUR/PDR/PMR can also be calculated with other parameter settings too. For example, with advances in sequencing technologies, longer reads that cover more CpGs may be sequenced. Alternatively, utilizing current technology, in CpG dense regions (CpG Islands, promoters, enhancers), a shorter read may cover more CpG sites. It also can be used on sequencing reads generated by all sequencing platforms, including Sanger sequencing, next generation sequencing and single-molecular sequencing.

Cancer-like tissues (ExE) and normal-like tissues (Epi) were checked, and it was found that fully methylated reads/haplotypes are very rare in normal cells and thus significantly reduce background noise (FIG. 15C). In contrast, notable background methylation is observed when current method mean methylation is used (FIG. 15B).

Example 3: Detection of Low Frequency Tumors (0.01%) from cfDNA Through Simulation It has been shown that in early stages of cancer, ctDNA only represents 0.01% to 1% of cfDNA from plasma. This is challenging in view of traditional methods of methylation analysis. Established herein is a novel way to predict ctDNA from cfDNA with a resolution as high as 0.01%, in which five copies of tumor DNA are present (FIG. 16). According to the simulations, the presence of 0.01% ctDNA can be predicted with 100% sensitivity and 95% specificity, with a p-value cutoff of $10^{-4}$.

A simulation was performed by mixing sequencing reads from tumor-like tissues (ExE), with fractions ranging from 1%, 0.1% and 0.01%, with reads from normal-like tissues (Epi). (Note: only reads that locate in a CpG Island and that distinguish tumor and normal were sampled (see Example 1)). 0.01% of tumor DNA mimic the fraction of circulating tumor DNA (ctDNA) among cell free DNA in early cancer patients. Random dropout of tumor reads in simulation mimiced the experimental dropout during sample preparation or sequencing. In every simulated sample (mixture of tumor-like reads and norm-like reads), PMR was calculated for each CpG Island, and then compared to background (pure normal-like tissue). If the signal was significantly higher in the simulated sample (by rank sum test), it was concluded that this sample contained tumor DNA.

Methods
Data Reporting

No statistical methods were used to predetermine sample size. The experiments were not randomized and the investigators were not blinded to allocation during experiments and outcome assessment.

Sample Isolation and Library Preparation

Preparation of preimplantation and post implantation samples was performed as described in ref 31. In brief, B6D2F1 hybrid females between 5 and 8 weeks old (Charles River) were serially primed with 5 IU pregnant mare gonadotropin (Sigma) followed by 5 IU human chorionic gonadotropin (Millipore) after 46 h, and subsequently mated with B6D2F1 male mice ≤6 months old. For preimplantation time points, zygotes from mated females were isolated from the oviduct the following morning (E0.5) and cultured in KSOM media (Millipore) droplets under mineral oil until E2.25. The 8-cell sample was collected by careful monitoring of 4-cell embryos from ~E2 onwards, and emergent 8-cell embryos were swapped into KSOM supplemented with 1 μg ml$^{-1}$ aphidicolin (Sigma) to ensure synchronization and minimal entry into the fourth replication cycle. 8-cell embryos were collected within 4 h of the first apparent embryo of this stage. Prior to collection, embryos were serially transferred through Acidic Tyrode's solution (Sigma) to remove the zona pellucida and carefully pipetted with a drawn glass capillary through 0.25% Trypsin-EDTA (Life Technologies) to remove maternal polar bodies. E3.5 blastocysts were also treated with Acidic Tyrode's solution to remove the zona, and the ICM and trophectoderm of matched samples were dissected using standard micromanipulation equipment (Eppendorf) and a Hamilton Thorne XYClone laser with 300 μs pulsing at 100% intensity. Isolation of post implantation tissues was performed as described[32]. The deciduae of mated female mice were isolated on the morning of E6.5 and the conceptuses removed. Then, under a stereomicroscope, the embryo was carefully bisected along the extraembryonic-embryonic axis, removing the ectoplacental cone from the extraembryonic ectoderm when apparent. After separation, the epiblast and the ExE were incubated for 15 min at 4° C. in 0.5% trypsin, 2.5% pancreatin dissolved in PBS and allowed to rest for 5-10 min in KSOM at room temperature. Finally, the visceral endoderm was removed by drawing the embryo through a narrow, flame-drawn glass capillary and only samples with no apparent contamination were collected. On average, matched ExE and epiblast or ICM and trophectoderm samples from 5-10 embryos or from 20 or more 8-cell embryos were collected per assay.

DNA for whole-genome bisulfite sequencing was isolated as described previously[33], and libraries were prepared using the Accel-NGS Bisulfite DNA library kit (Swift Biosciences) according to the manufacturer's protocol. Final libraries were generated from 10-12 PCR cycles. RNA was purified using the RNeasy Micro Kit (Qiagen) and RNA-seq libraries were generated using the SMRTseq v4 Ultra Low Input Kit (Clontech) according to the manufacturer's protocol with 10-11 long-distance PCR cycles. Libraries were generated from 150 pg of the subsequent cDNA using the Nextera XT DNA library preparation kit (Illumina) and 12 PCR cycles. ATAC-seq libraries were generated as described previously[34] using a 10 μl reaction and incubation with the TN5 transposase mixture (Nextera DNA library preparation kit, Illumina) for 45 min. The reaction was stopped according to the protocol described previously[35] and purified using silane beads (Thermo Fisher). Tagmented DNA was amplified for 12-14 cycles to generate the library. WGBS libraries were sequenced as a pool using the HiSeq X Ten platform (Illumina), and RNA-seq and ATAC-seq data were sequenced using the HiSeq 2500 (Illumina).

Outgrowth Experiments

To generate controlled outgrowth data, ICM were immunosurgically isolated from BDF1×129S1/SvImJ strain blastocysts at 96 h post fertilization as described[31]. In brief, oocytes were isolated by hormone priming from B6D2F1 females 12-14 h after administration of human chorionic gonadotropin and fertilized by intracytoplasmic sperm injection using piezo-actuated injection of 129S1/SvImJ strain sperm[36]. At 96 h post-fertilization, blastocysts were stripped of their zona pellucida by brief incubation in Acidic Tyrode's solution and incubated for 30 min in 1:10 diluted whole mouse antisera (Sigma) in $CO_2$-equilibrated KSOM, followed by destruction of the trophectoderm by culture in 1:10 diluted guinea pig complement sera (Sigma). After 15 min at 37° C., the ICM separates from the complement-lysed trophectoderm and could be cleanly isolated by brief pulsing through a narrow glass capillary. ICM were isolated in batches of ~12 per drop. Once isolated, ICM were then plated into basal N2/B27 media supplemented with 1,000 U ml$^{-1}$ leukaemia inhibitory factor (made in house) and one of the following conditions; '2i' supplemented with 1 μM PD0325901 and 3 μM CHIR99021 (Reagents Direct)[37]; 'PD0325901' supplemented with 1 μM PD0325901 and 10 ng ml$^{-1}$ BMP4 to promote outgrowth expansion (Peprotech)[38]; 'FGF plus CHIR' supplemented with 25 ng ml$^{-1}$ mouse recombinant FGF4 (R&D systems) and 3 μM CHIR99021; and 'FGF' supplemented with 25 ng ml$^{-1}$ FGF4 only. FGF4 was selected because it is the most highly expressed FGF family member in the preimplantation embryo and we sought to direct specific remethylation changes as is observed in vivo. ICM were placed into gelatin-treated tissue culture dishes plated with irradiated CF-1 strain embryonic fibroblasts to promote attachment. The primary outgrowth from the ICM, characterized as a centrally expanding, three-dimensional mass, was isolated after four days of culture. In all cases but the 2i condition, an outer layer of differentiated cells was apparent and removed using an identical strategy to that of removal of the visceral endoderm from E6.5 samples described above. However, under the FGF plus CHIR condition, the 'outer layer' was often of the same size or larger than the internal outgrowth, and only became defined during the latter portion of culture (see FIG. 9B). As such, we collected both interior and exterior portions as they could clearly be distinguished as mutually ICM-derived. After incubation and either isolation or removal of external cells, outgrowths were serially washed through several KSOM drops under mineral oil before being snap-frozen in minimal volume for RNA-seq and RRBS profiling.

Generation of Knockout Embryos by Zygotic CRISPR-Cas9 Injection

Zygotic injection was performed essentially as described[39]. To improve the efficiency with which null alleles were generated, three separate single-guide RNA (sgRNA) sequences were designed per target, prioritizing highly scored protospacer sequences with no high scoring off-target sites using the CHOPCHOP web tool[40] and as 5' as possible given these constraints to disrupt the coding frame Protospacer sequences were input into the following oligonucleotide primer pair and used to amplify off of the pX300 plasmid (Addgene): forward primer, AGTCAGTTAATACGACTCACTATAGN19GTTT-TAGAGCTAGAAATAGCAAG (SEQ ID NO: 1); reverse primer, AAAAAAAGCACCGACTCGGTGCCAC (SEQ ID NO: 2). Protospacer sequences that did not begin with a G to initiate T7 transcription were inserted and an additional 5' G was added. 200 ng of gel-purified, T7 promoter-containing sgRNA templates were used to generate sgRNAs by in vitro transcription using the MEGAshortscript T7 transcription kit (Thermo Fisher), followed by purification with phenol:chloroform and ethanol precipitation. Translation-competent spCas9 RNA was in vitro transcribed from a similarly designed, T7 promoter-driven template using the mMESSAGE mMACHINE T7 Ultra kit (Thermo Fisher) and purified using the RNA Clean and Concentrator Kit (Zymo Research). RNA was resuspended in an injection buffer comprising 5 mM Tris-HCl and 0.1 mM EDTA at pH 7.4. Zygotes were isolated from hormone-primed B6D2F1 females mated with B6D2F1 males as described above. Shortly after the formation of visible pronuclei (pronuclear stage 3), zygotes were cytoplasmically injected with 100 ng $\mu l^{-1}$ of all three targeted sgRNAs pooled 1:1:1 and 200 ng$^{-1}$ Cas9 mRNA. At E3.5, cavitated blastocysts were transferred in clutches of 10-15 into one uterine horn of pseudopregnant CD-1 strain mice (Charles River) that had been mated with vasectomized male Swiss-Weber strain mice (Taconic) two days previously. To account for the ~1 day offset in developmental progression that results from uterine transfer, appropriately E6.5 stage conceptuses were isolated 4 days after uterine transfer and epiblast and extraembryonic ectoderm tissue were isolated as described above before snap-freezing in minimal volume. Each replicate consisted of at least 4 embryos and all experimental series include replicates generated from at least 2 rounds of zygotic injection. Care was taken to ensure epiblast and extraembryonic ectoderm tissue from matched embryos were included for each replicate set, and RRBS data in which both fractions did not cover >1 million CpGs at ≥5× coverage each were excluded from further analysis. Disruption of the target allele was confirmed by PCR amplification from the primary cDNA using primers that flank all three protospacer sequences to capture multiple simultaneous perturbations or truncations in phase.

Dual RNA-Seq and RRBS Profiling

Genomic DNA and mRNA purifications from low input samples were performed as described previously with modifications[41]. In brief, the cells were mixed with 15 µl of RLT plus buffer (Qiagen) containing 1 U µl$^{-1}$ of SUPERase. In RNase inhibitor (ThermoFisher), 1% β-mercaptoethanol (Sigma), and were then transferred to 1 well in a 96-well DNA LoBind plate (Eppendorf). After adding 10 µl of M-280 streptavidin bead-conjugated reverse transcription primer to each sample, the reaction was incubated at 72° C. for 3 min in a thermocycler followed by incubation at room temperature for 25 min with gentle rotation. The genomic DNA and mRNA were separated in a DynaMag-96 Side Magnet (Thermo Fisher). The bead-tagged mRNA was subjected to reverse transcription as described previously[41] and the genomic DNA in the supernatant was transferred to a fresh 96-well DNA LoBind plate. After reverse transcription, the cDNA was PCR amplified and the RNA-seq library was generated according to the Smart-seq2 protocol[42]. Indexed RNA-seq libraries were pooled and sequenced in an Illumina Hiseq2500 sequencer.

Genomic DNA was isolated using 1× Agencourt AMPure beads (Beckman Coulter) and was eluted with 15 µl of low Tris-EDTA buffer. The RRBS library was generated as reported previously with modifications[43]. We used the CutSmart buffer (New England Biolabs) for all three enzymatic reactions including MspI digestion, end-repair/A-tailing and T4 DNA ligation. To minimize DNA loss, the DNA purification step was eliminated after each enzymatic reaction. In brief, the genomic DNA was digested by 16 units of MspI (New England Biolabs) for 80 min at 37° C., and followed by heat inactivation at 65° C. for 15 min. The digested DNA fragments were end-repaired and A-tailed by adding 4 units of Klenow fragment (3'→5' exo-) (New England Biolabs), 0.03 mM dCTP, 0.03 mM dGTP and 0.3 mM dATP; the reaction was carried out at 30° C. for 25 min and 37° C. for 25 min, followed by incubation at 70° C. for 10 min to inactive the enzyme. We then ligated the A-tailed DNA fragments with indexed adapters overnight at 16° C., by adding 2,000 U of T4 DNA ligase, 0.75 mM ATP and 7 nM of the adapters. The T4 ligase was heat-inactivated at 65° C. for 15 min before pooling libraries together. To remove adaptor dimers, the library pool was cleaned up using 1.8× AMPure beads and the adaptor-tagged DNA fragments were eluted to 30 µl of low Tris-EDTA buffer. The bisulfite conversion of the adaptor-tagged DNA fragments was conducted using a Qiagen EpiTect Fast Bisulfite Conversion Kit following the manufacturer's instructions with a minor modification. We extended the bisulfite conversion time from 2 cycles of 10 min to 2 cycles of 20 min to achieve bisulfite conversion rates >99%. The bisulfite-converted DNA fragments were PCR amplified according to the following thermocycler settings: 98° C. for 45 s, 6 cycles of 98° C. for 20 s, 58° C. for 30 s, 72° C. for 1 min, and then 8-10 cycles of 98° C. for 20 s, 65° C. for 30 s, 72° C. for 1 min, followed by a final extension cycle of 5 min at 72° C. The PCR-amplified library DNA was cleaned up using 1.3× AMPure beads and the RRBS libraries were paired-end sequenced for 2×100 cycles. Only instances in which the matched pool of Epiblast and ExE from a given replicate both had >1 million CpGs covered at ≥5× were included for downstream analysis.

For each sample, 10 µl of M-280 streptavidin beads (Thermo Fisher) were prepared as per the manufacturer's recommendations. Specifically, after washing with Solution A (0.1 M NaOH, 0.05 M NaCl) and B (0.1 M NaCl) sequentially, the beads were resuspended in 10 µl of 2× binding and washing buffer (10 mM Tris-HCl, 1 mM EDTA, 2 M NaCl) and then mixed with an equal volume of 2 µM of reverse transcription primer[41]. The mixture was incubated for 15 min at room temperature with gentle rotation. The bead-bound reverse transcription primer was collected using a magnet and was subsequently resuspended in 10 µl of binding buffer (10 mM Tris-HCl (pH 8.0), 167 mM NaCl, 0.05% Tween-20).

Estimating Methylation Levels

The methylation level of each sampled cytosine was estimated as the number of reads reporting a C, divided by the total number of reads reporting a C or T. Single CpG methylation levels were limited to those CpGs that had at least fivefold coverage. For 100 bp tiles, reads for all the CpGs that were covered more than fivefold within the tile were pooled and used to estimate the methylation level as described for single CpGs. The CpG density for a given single CpG is the number of CpGs 50 bp up- and downstream of that CpG. The CpG density for a 100 bp tile is the number of CpGs in the tile. The methylation level reported for a sample is the average methylation by pooling all reads across replicates.

Genomic Features

LINE, LTR and SINE annotations were downloaded from the UCSC (University of California, Santa Cruz) browser (mm9) RepeatMasker tracks. CGI annotations were downloaded from the UCSC browser (mm9) CpG Islands track. Gene annotations (exon, 5' exon, intron) were downloaded from the UCSC browser (mm9) RefSeq track. Promoters (TSSs) are defined as ±2 kb of the RefSeq annotation. Corresponding human annotations were downloaded from the UCSC browser for hg19. In each case, the methylation level of an individual feature is estimated by averaging methylation for all CpGs within the feature that are covered greater than fivefold. Assignment of CGIs to a given TSS (CGI promoters) included annotated CGIs that fell within this boundary. Methylation was estimated for 'core TSS' sequences defined as ±1 kb of the RefSeq annotation and only included CpGs measured at ≥5× in both samples (WGBS) or pooled samples (RRBS). For FIG. 2B, FIG. 7F, and FIG. 9C, promoters for all isoforms are included and the maximally different alternative TSS was reported. The methylation levels of all annotated TSSs were calculated and reported in this manner, with the mean transcripts per million (TPM) estimate for the gene reported for all associated TSSs.

Identification of Differentially Methylated Loci and Regions

For WGBS data, identification of differentially methylated loci was performed using the DSS package, which uses biological replicates and information from CpG sites across the genome to stabilize the estimation of the dispersion parameters[44]. Only CpGs that were covered at least fivefold across all samples were considered for a given comparison. A false discovery rate (FDR) cut-off of 5% was used to identify differentially methylated CpGs. A CGI was called as differentially methylated if it was covered by at least 5 CpGs and 80% of them were significantly hyper/hypo methylated. For TCGA Illumina Infinium HumanMethylation450K BeadChip data, given that most cancer types have more than 20 cancer and normal samples, Wilcoxon rank-sum test was used to identify differentially methylated CpGs, with a FDR cut-off of 5%. All statistical tests throughout this study are two-sided. A CGI was called as differentially methylated if 80% of covered CpGs were significantly hyper/hypo methylated. For RRBS data, a simple cut-off of 10% difference in CGI-level methylation was used to call differential methylation.

Gene Expression Analysis

Alignment was performed using TopHat2 against mouse genome assembly mm9 with default settings. Isoform-level expression was quantified by kallisto, which performs pseudoalignment of reads against cDNA sequence of transcripts. Gene-level expression was estimated as the sum of expression of associated isoforms. Refseq mRNA sequences were downloaded from the UCSC genome browser. Expression levels were reported as transcripts per million (TPM).

Pathway Enrichment

Pathway enrichment was performed by a hypergeometric test using the GSEA online tool. The P value was adjusted for multiple hypothesis testing according to Benjamini and Hochberg, with 5% as a cut-off. Regulation by PRC2 in human ES cells taken from ref. 45.

Connectivity Analysis

We used GRAIL (gene relationships across implicated loci)[46] to test whether a query gene is functionally related to a set of seed genes. GRAIL uses text-mining to quantify the relatedness between two genes in the genome, by which a global gene network is built. It has been demonstrated that genes that function in the same pathway tend to distribute in a coherent subnetwork. In this study, we built a subnetwork using ExE hyper CGI-associated genes, which were significantly enriched in several pathways. To predict whether a query gene is functionally related to the ExE hyper subnetwork, we project this gene to the global network, and test whether connection of this gene to the subnetwork is random or statistically significant.

ATAC-Seq Data Processing

Reads were aligned to mouse genome mm9 using BWA with default parameters. Duplicates were removed by the function MarkDuplicates from the Picard tool kit. Reads with low mapping quality (<10) or in the mitochondrial chromosome were removed. NucleoATAC was used to generate insert density, which was normalized by the total number of insertions in each sample47.

Orthology Mapping Between Human and Mouse

Mouse mm9 CGIs were mapped to human hg19 segments using liftOver with chain file mm9ToHg19.over.chain. Then human orthologous CGIs were defined as the nearest CGIs to the mapped segments.

Data Availability

All datasets have been deposited in the Gene Expression Omnibus and are accessible under GSE84236. Additional data include: Roadmap and ENCODE samples from RnBeads Methylome Resource (rnbeads.mpiinf.mpg.de/methylomes.php), mouse adult tissues from GSE42836, and CLL and normal B lymphocytes from GSE58889.

TABLE 1

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
| --- | --- | --- |
| chr1: 1181756-1182470 | 3 | Mouse ExE ortholog |
| chr1: 1470604-1471450 | 0 | Mouse ExE ortholog |
| chr1: 2772126-2772665 | 1 | Mouse ExE ortholog |
| chr1: 4713989-4716555 | 9 | Mouse ExE ortholog |
| chr1: 18436551-18437673 | 5 | Mouse ExE ortholog |
| chr1: 18956895-18959829 | 12 | Mouse ExE ortholog |
| chr1: 18962842-18963481 | 7 | Mouse ExE ortholog |
| chr1: 18967251-18968119 | 0 | Mouse ExE ortholog |
| chr1: 19203874-19204234 | 1 | Mouse ExE ortholog |
| chr1: 21616380-21617101 | 0 | Mouse ExE ortholog |
| chr1: 25255527-25259005 | 5 | Mouse ExE ortholog |
| chr1: 29585897-29586598 | 1 | Mouse ExE ortholog |
| chr1: 34628783-34630976 | 7 | Mouse ExE ortholog |
| chr1: 39980365-39981768 | 13 | Mouse ExE ortholog |
| chr1: 40235767-40237190 | 0 | Mouse ExE ortholog |
| chr1: 41831976-41832542 | 0 | Mouse ExE ortholog |
| chr1: 46951168-46951792 | 12 | Mouse ExE ortholog |
| chr1: 47909712-47911020 | 13 | Mouse ExE ortholog |
| chr1: 53742297-53742845 | 2 | Mouse ExE ortholog |
| chr1: 55505060-55506015 | 3 | Mouse ExE ortholog |
| chr1: 61515875-61516831 | 1 | Mouse ExE ortholog |
| chr1: 63782394-63790471 | 2 | Mouse ExE ortholog |
| chr1: 65731411-65731849 | 7 | Mouse ExE ortholog |
| chr1: 66258440-66258918 | 12 | Mouse ExE ortholog |
| chr1: 77747314-77748224 | 7 | Mouse ExE ortholog |
| chr1: 91172102-91172771 | 10 | Mouse ExE ortholog |
| chr1: 91176404-91176701 | 14 | Mouse ExE ortholog |
| chr1: 92945907-92952609 | 1 | Mouse ExE ortholog |
| chr1: 115880167-115881332 | 6 | Mouse ExE ortholog |
| chr1: 116380359-116382364 | 3 | Mouse ExE ortholog |
| chr1: 156105707-156106171 | 5 | Mouse ExE ortholog |
| chr1: 156338758-156339251 | 0 | Mouse ExE ortholog |
| chr1: 156358050-156358252 | 10 | Mouse ExE ortholog |
| chr1: 156390403-156391581 | 1 | Mouse ExE ortholog |
| chr1: 160340604-160340843 | 13 | Mouse ExE ortholog |
| chr1: 161695637-161697298 | 0 | Mouse ExE ortholog |
| chr1: 177133392-177133846 | 10 | Mouse ExE ortholog |
| chr1: 180198119-180204975 | 0 | Mouse ExE ortholog |
| chr1: 197887088-197887791 | 8 | Mouse ExE ortholog |
| chr1: 201252452-201253648 | 3 | Mouse ExE ortholog |
| chr1: 202678881-202679769 | 6 | Mouse ExE ortholog |
| chr1: 214156000-214156851 | 10 | Mouse ExE ortholog |
| chr1: 214158726-214159080 | 9 | Mouse ExE ortholog |
| chr1: 221057463-221057757 | 11 | Mouse ExE ortholog |
| chr1: 221067447-221068185 | 12 | Mouse ExE ortholog |
| chr1: 226075150-226075680 | 12 | Mouse ExE ortholog |
| chr1: 248020330-248021252 | 5 | Mouse ExE ortholog |
| chr10: 50602989-50606783 | 8 | Mouse ExE ortholog |
| chr10: 50817601-50820356 | 11 | Mouse ExE ortholog |
| chr10: 71331926-71333392 | 7 | Mouse ExE ortholog |
| chr10: 88122924-88127364 | 5 | Mouse ExE ortholog |
| chr10: 94820026-94823252 | 11 | Mouse ExE ortholog |
| chr10: 101279941-101280382 | 6 | Mouse ExE ortholog |
| chr10: 101281181-101282116 | 8 | Mouse ExE ortholog |
| chr10: 102419147-102419668 | 11 | Mouse ExE ortholog |

TABLE 1-continued

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
|---|---|---|
| chr10: 102473206-102474026 | 9 | Mouse ExE ortholog |
| chr10: 102484200-102484476 | 11 | Mouse ExE ortholog |
| chr10: 102489343-102491011 | 2 | Mouse ExE ortholog |
| chr10: 102507482-102509646 | 4 | Mouse ExE ortholog |
| chr10: 102893660-102895059 | 13 | Mouse ExE ortholog |
| chr10: 102896342-102896665 | 13 | Mouse ExE ortholog |
| chr10: 102899822-102900263 | 13 | Mouse ExE ortholog |
| chr10: 102975969-102978096 | 4 | Mouse ExE ortholog |
| chr10: 105361784-105362188 | 0 | Mouse ExE ortholog |
| chr10: 105420685-105421076 | 6 | Mouse ExE ortholog |
| chr10: 106399567-106402812 | 13 | Mouse ExE ortholog |
| chr10: 118899247-118900329 | 14 | Mouse ExE ortholog |
| chr10: 119000435-119001530 | 7 | Mouse ExE ortholog |
| chr10: 119311204-119312104 | 10 | Mouse ExE ortholog |
| chr10: 119312766-119313563 | 5 | Mouse ExE ortholog |
| chr10: 124905634-124906161 | 12 | Mouse ExE ortholog |
| chr10: 124907283-124911035 | 11 | Mouse ExE ortholog |
| chr10: 129534410-129537366 | 10 | Mouse ExE ortholog |
| chr11: 725596-726870 | 6 | Mouse ExE ortholog |
| chr11: 8190226-8190671 | 10 | Mouse ExE ortholog |
| chr11: 17740789-17743779 | 7 | Mouse ExE ortholog |
| chr11: 20181200-20182325 | 14 | Mouse ExE ortholog |
| chr11: 20622720-20623399 | 13 | Mouse ExE ortholog |
| chr11: 31825743-31826967 | 14 | Mouse ExE ortholog |
| chr11: 31839363-31839813 | 14 | Mouse ExE ortholog |
| chr11: 31848487-31848776 | 14 | Mouse ExE ortholog |
| chr11: 32452144-32452708 | 13 | Mouse ExE ortholog |
| chr11: 32454874-32457311 | 9 | Mouse ExE ortholog |
| chr11: 36397926-36399398 | 0 | Mouse ExE ortholog |
| chr11: 44327240-44327932 | 2 | Mouse ExE ortholog |
| chr11: 46299544-46300216 | 0 | Mouse ExE ortholog |
| chr11: 46366876-46367101 | 3 | Mouse ExE ortholog |
| chr11: 64136814-64138187 | 0 | Mouse ExE ortholog |
| chr11: 65352231-65353134 | 13 | Mouse ExE ortholog |
| chr11: 69517840-69519929 | 0 | Mouse ExE ortholog |
| chr11: 69831571-69832484 | 4 | Mouse ExE ortholog |
| chr11: 70672834-70673055 | 8 | Mouse ExE ortholog |
| chr11: 72532612-72533774 | 2 | Mouse ExE ortholog |
| chr11: 79148358-79152200 | 4 | Mouse ExE ortholog |
| chr11: 124629723-124629926 | 6 | Mouse ExE ortholog |
| chr12: 3475010-3475654 | 3 | Mouse ExE ortholog |
| chr12: 5018585-5021171 | 9 | Mouse ExE ortholog |
| chr12: 6438272-6438931 | 2 | Mouse ExE ortholog |
| chr12: 15475318-15475901 | 8 | Mouse ExE ortholog |
| chr12: 29302034-29302954 | 2 | Mouse ExE ortholog |
| chr12: 45444202-45445386 | 8 | Mouse ExE ortholog |
| chr12: 49183049-49183282 | 0 | Mouse ExE ortholog |
| chr12: 49371690-49375550 | 1 | Mouse ExE ortholog |
| chr12: 49484920-49485178 | 7 | Mouse ExE ortholog |
| chr12: 53491572-53491955 | 0 | Mouse ExE ortholog |
| chr12: 54338761-54339168 | 11 | Mouse ExE ortholog |
| chr12: 54366815-54369103 | 2 | Mouse ExE ortholog |
| chr12: 54378696-54380102 | 1 | Mouse ExE ortholog |
| chr12: 54423427-54423712 | 11 | Mouse ExE ortholog |
| chr12: 54440642-54441543 | 9 | Mouse ExE ortholog |
| chr12: 54447744-54448091 | 10 | Mouse ExE ortholog |
| chr12: 54519768-54520457 | 2 | Mouse ExE ortholog |
| chr12: 57618769-57619402 | 4 | Mouse ExE ortholog |
| chr12: 58003880-58004249 | 7 | Mouse ExE ortholog |
| chr12: 58158855-58160000 | 0 | Mouse ExE ortholog |
| chr12: 63543636-63544967 | 12 | Mouse ExE ortholog |
| chr12: 75602991-75603344 | 13 | Mouse ExE ortholog |
| chr12: 99139386-99139769 | 10 | Mouse ExE ortholog |
| chr12: 101109863-101111622 | 11 | Mouse ExE ortholog |
| chr12: 106979429-106981086 | 12 | Mouse ExE ortholog |
| chr12: 113590806-113591304 | 0 | Mouse ExE ortholog |
| chr12: 113900750-113906442 | 5 | Mouse ExE ortholog |
| chr12: 113908887-113910681 | 9 | Mouse ExE ortholog |
| chr12: 113913615-113914322 | 13 | Mouse ExE ortholog |
| chr12: 114878143-114879155 | 12 | Mouse ExE ortholog |
| chr12: 114886354-114886579 | 11 | Mouse ExE ortholog |
| chr12: 115109503-115110061 | 7 | Mouse ExE ortholog |
| chr12: 117798076-117799448 | 9 | Mouse ExE ortholog |
| chr12: 120835586-120835927 | 11 | Mouse ExE ortholog |
| chr12: 122016170-122017693 | 4 | Mouse ExE ortholog |
| chr12: 130387609-130389139 | 13 | Mouse ExE ortholog |
| chr12: 130908777-130909191 | 0 | Mouse ExE ortholog |
| chr13: 27334226-27335205 | 8 | Mouse ExE ortholog |
| chr13: 28498226-28499046 | 14 | Mouse ExE ortholog |
| chr13: 36049570-36050159 | 8 | Mouse ExE ortholog |
| chr13: 36052553-36053119 | 7 | Mouse ExE ortholog |
| chr13: 79182859-79183880 | 2 | Mouse ExE ortholog |
| chr13: 84453664-84453897 | 14 | Mouse ExE ortholog |
| chr13: 108518334-108518633 | 9 | Mouse ExE ortholog |
| chr13: 109147798-109149019 | 13 | Mouse ExE ortholog |
| chr14: 36974548-36975425 | 9 | Mouse ExE ortholog |
| chr14: 36986362-36990576 | 4 | Mouse ExE ortholog |
| chr14: 37049333-37051726 | 6 | Mouse ExE ortholog |
| chr14: 37116188-37117628 | 1 | Mouse ExE ortholog |
| chr14: 38678245-38680937 | 7 | Mouse ExE ortholog |
| chr14: 54418677-54418881 | 9 | Mouse ExE ortholog |
| chr14: 57274607-57276840 | 13 | Mouse ExE ortholog |
| chr14: 57283967-57284558 | 11 | Mouse ExE ortholog |
| chr14: 69256676-69257036 | 5 | Mouse ExE ortholog |
| chr14: 74706188-74708192 | 11 | Mouse ExE ortholog |
| chr14: 95237622-95238211 | 13 | Mouse ExE ortholog |
| chr14: 105167663-105168129 | 0 | Mouse ExE ortholog |
| chr15: 33009530-33011696 | 7 | Mouse ExE ortholog |
| chr15: 40268581-40269061 | 6 | Mouse ExE ortholog |
| chr15: 45408573-45409528 | 7 | Mouse ExE ortholog |
| chr15: 47476369-47477499 | 10 | Mouse ExE ortholog |
| chr15: 49254984-49255564 | 1 | Mouse ExE ortholog |
| chr15: 60287107-60287663 | 8 | Mouse ExE ortholog |
| chr15: 60296135-60298520 | 5 | Mouse ExE ortholog |
| chr15: 67073306-67073943 | 0 | Mouse ExE ortholog |
| chr15: 74419870-74423044 | 3 | Mouse ExE ortholog |
| chr15: 79724099-79725643 | 6 | Mouse ExE ortholog |
| chr15: 89914363-89915061 | 12 | Mouse ExE ortholog |
| chr15: 89920793-89922768 | 7 | Mouse ExE ortholog |
| chr15: 89949373-89951130 | 12 | Mouse ExE ortholog |
| chr15: 91642908-91643702 | 2 | Mouse ExE ortholog |
| chr15: 96873408-96877721 | 2 | Mouse ExE ortholog |
| chr16: 2228190-2230946 | 0 | Mouse ExE ortholog |
| chr16: 3013016-3013228 | 3 | Mouse ExE ortholog |
| chr16: 3190765-3191389 | 0 | Mouse ExE ortholog |
| chr16: 22824616-22826459 | 12 | Mouse ExE ortholog |
| chr16: 48844551-48845264 | 13 | Mouse ExE ortholog |
| chr16: 49311413-49312308 | 11 | Mouse ExE ortholog |
| chr16: 49314037-49316543 | 9 | Mouse ExE ortholog |
| chr16: 49872449-49874926 | 11 | Mouse ExE ortholog |
| chr16: 51147490-51147944 | 8 | Mouse ExE ortholog |
| chr16: 51168266-51169110 | 13 | Mouse ExE ortholog |
| chr16: 54970301-54972846 | 7 | Mouse ExE ortholog |
| chr16: 55513220-55513526 | 7 | Mouse ExE ortholog |
| chr16: 58030214-58031633 | 0 | Mouse ExE ortholog |
| chr16: 62069121-62070634 | 11 | Mouse ExE ortholog |
| chr16: 67208067-67208678 | 0 | Mouse ExE ortholog |
| chr16: 67571252-67572728 | 1 | Mouse ExE ortholog |
| chr16: 68480864-68482822 | 1 | Mouse ExE ortholog |
| chr16: 86530747-86532994 | 7 | Mouse ExE ortholog |
| chr16: 86549069-86550512 | 6 | Mouse ExE ortholog |
| chr16: 86612188-86613821 | 8 | Mouse ExE ortholog |
| chr16: 88943427-88943669 | 0 | Mouse ExE ortholog |
| chr17: 12568667-12569335 | 3 | Mouse ExE ortholog |
| chr17: 14248391-14248721 | 0 | Mouse ExE ortholog |
| chr17: 32484007-32484280 | 15 | Mouse ExE ortholog |
| chr17: 35291899-35300875 | 5 | Mouse ExE ortholog |
| chr17: 37764092-37764304 | 3 | Mouse ExE ortholog |
| chr17: 40937258-40937480 | 9 | Mouse ExE ortholog |
| chr17: 43472527-43474343 | 0 | Mouse ExE ortholog |
| chr17: 45949676-45949885 | 2 | Mouse ExE ortholog |
| chr17: 46607804-46608390 | 5 | Mouse ExE ortholog |

TABLE 1-continued

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
| --- | --- | --- |
| chr17: 46620367-46621373 | 1 | Mouse ExE ortholog |
| chr17: 46631800-46632212 | 6 | Mouse ExE ortholog |
| chr17: 46669434-46669811 | 8 | Mouse ExE ortholog |
| chr17: 46691520-46692097 | 7 | Mouse ExE ortholog |
| chr17: 48194634-48195085 | 0 | Mouse ExE ortholog |
| chr17: 50235175-50236466 | 12 | Mouse ExE ortholog |
| chr17: 59485573-59485780 | 11 | Mouse ExE ortholog |
| chr17: 59528979-59530266 | 14 | Mouse ExE ortholog |
| chr17: 70116274-70119998 | 1 | Mouse ExE ortholog |
| chr17: 70120139-70120442 | 7 | Mouse ExE ortholog |
| chr17: 72855621-72858012 | 0 | Mouse ExE ortholog |
| chr17: 72915568-72916510 | 4 | Mouse ExE ortholog |
| chr17: 74017769-74018658 | 5 | Mouse ExE ortholog |
| chr17: 77805866-77809046 | 0 | Mouse ExE ortholog |
| chr17: 79314962-79320653 | 0 | Mouse ExE ortholog |
| chr17: 79859808-79860963 | 1 | Mouse ExE ortholog |
| chr18: 19744936-19752363 | 1 | Mouse ExE ortholog |
| chr18: 30349690-30352302 | 2 | Mouse ExE ortholog |
| chr18: 35144907-35147628 | 6 | Mouse ExE ortholog |
| chr18: 55103154-55108853 | 6 | Mouse ExE ortholog |
| chr18: 55922987-55924068 | 1 | Mouse ExE ortholog |
| chr18: 59000683-59001692 | 12 | Mouse ExE ortholog |
| chr18: 74153239-74155073 | 0 | Mouse ExE ortholog |
| chr18: 74961556-74963822 | 13 | Mouse ExE ortholog |
| chr19: 407011-409511 | 0 | Mouse ExE ortholog |
| chr19: 1063544-1064265 | 4 | Mouse ExE ortholog |
| chr19: 1108394-1109610 | 2 | Mouse ExE ortholog |
| chr19: 1748167-1750243 | 1 | Mouse ExE ortholog |
| chr19: 2424005-2427983 | 0 | Mouse ExE ortholog |
| chr19: 7933263-7934898 | 0 | Mouse ExE ortholog |
| chr19: 11594372-11594987 | 1 | Mouse ExE ortholog |
| chr19: 13135317-13136169 | 8 | Mouse ExE ortholog |
| chr19: 13198699-13198999 | 2 | Mouse ExE ortholog |
| chr19: 13213450-13213821 | 2 | Mouse ExE ortholog |
| chr19: 18979351-18981200 | 13 | Mouse ExE ortholog |
| chr19: 19368708-19369681 | 0 | Mouse ExE ortholog |
| chr19: 30715549-30715753 | 0 | Mouse ExE ortholog |
| chr19: 35633409-35633697 | 1 | Mouse ExE ortholog |
| chr19: 36336275-36337138 | 2 | Mouse ExE ortholog |
| chr19: 36500169-36500530 | 1 | Mouse ExE ortholog |
| chr19: 38876070-38876332 | 0 | Mouse ExE ortholog |
| chr19: 42891311-42891646 | 0 | Mouse ExE ortholog |
| chr19: 45898879-45900315 | 4 | Mouse ExE ortholog |
| chr19: 48965002-48965792 | 2 | Mouse ExE ortholog |
| chr19: 50881418-50881664 | 3 | Mouse ExE ortholog |
| chr19: 50931270-50931638 | 3 | Mouse ExE ortholog |
| chr19: 51169659-51172023 | 9 | Mouse ExE ortholog |
| chr19: 55815940-55816277 | 0 | Mouse ExE ortholog |
| chr19: 56598038-56600296 | 2 | Mouse ExE ortholog |
| chr2: 3750828-3751927 | 8 | Mouse ExE ortholog |
| chr2: 30453566-30455655 | 1 | Mouse ExE ortholog |
| chr2: 38301276-38304518 | 0 | Mouse ExE ortholog |
| chr2: 45155195-45157049 | 12 | Mouse ExE ortholog |
| chr2: 45395869-45398186 | 5 | Mouse ExE ortholog |
| chr2: 50574045-50574817 | 10 | Mouse ExE ortholog |
| chr2: 66808568-66809404 | 13 | Mouse ExE ortholog |
| chr2: 71787430-71787897 | 3 | Mouse ExE ortholog |
| chr2: 73143055-73148260 | 1 | Mouse ExE ortholog |
| chr2: 80529677-80530846 | 11 | Mouse ExE ortholog |
| chr2: 102803672-102804556 | 2 | Mouse ExE ortholog |
| chr2: 105459127-105461770 | 12 | Mouse ExE ortholog |
| chr2: 105468851-105473488 | 4 | Mouse ExE ortholog |
| chr2: 108602824-108603467 | 11 | Mouse ExE ortholog |
| chr2: 119599458-119600966 | 12 | Mouse ExE ortholog |
| chr2: 137522460-137523696 | 8 | Mouse ExE ortholog |
| chr2: 142887724-142888553 | 7 | Mouse ExE ortholog |
| chr2: 144694666-144695180 | 3 | Mouse ExE ortholog |
| chr2: 157185557-157186355 | 7 | Mouse ExE ortholog |
| chr2: 162273294-162273725 | 8 | Mouse ExE ortholog |
| chr2: 176949511-176949795 | 9 | Mouse ExE ortholog |
| chr2: 176964062-176965509 | 12 | Mouse ExE ortholog |
| chr2: 176969217-176969895 | 6 | Mouse ExE ortholog |
| chr2: 176977284-176977540 | 13 | Mouse ExE ortholog |
| chr2: 176982107-176982402 | 12 | Mouse ExE ortholog |
| chr2: 177036254-177037213 | 14 | Mouse ExE ortholog |
| chr2: 177042751-177043444 | 2 | Mouse ExE ortholog |
| chr2: 182321761-182323029 | 10 | Mouse ExE ortholog |
| chr2: 182521221-182521927 | 2 | Mouse ExE ortholog |
| chr2: 219736132-219736592 | 8 | Mouse ExE ortholog |
| chr2: 219848919-219850541 | 6 | Mouse ExE ortholog |
| chr2: 219857682-219858917 | 1 | Mouse ExE ortholog |
| chr2: 220299483-220300243 | 10 | Mouse ExE ortholog |
| chr2: 220412341-220412678 | 0 | Mouse ExE ortholog |
| chr2: 223183013-223185468 | 0 | Mouse ExE ortholog |
| chr2: 237071794-237078762 | 7 | Mouse ExE ortholog |
| chr2: 241758141-241760783 | 3 | Mouse ExE ortholog |
| chr20: 3145121-3145746 | 5 | Mouse ExE ortholog |
| chr20: 21485932-21496714 | 5 | Mouse ExE ortholog |
| chr20: 21686199-21687689 | 12 | Mouse ExE ortholog |
| chr20: 22557517-22559240 | 8 | Mouse ExE ortholog |
| chr20: 33296514-33298242 | 0 | Mouse ExE ortholog |
| chr20: 37352130-37357372 | 13 | Mouse ExE ortholog |
| chr20: 39994545-39995810 | 7 | Mouse ExE ortholog |
| chr20: 44657463-44659243 | 12 | Mouse ExE ortholog |
| chr20: 44685771-44687610 | 9 | Mouse ExE ortholog |
| chr20: 51589707-51590020 | 4 | Mouse ExE ortholog |
| chr20: 52789252-52790986 | 3 | Mouse ExE ortholog |
| chr20: 57415135-57417153 | 5 | Mouse ExE ortholog |
| chr21: 31311386-31312106 | 11 | Mouse ExE ortholog |
| chr21: 32624144-32624382 | 0 | Mouse ExE ortholog |
| chr21: 38065179-38066185 | 10 | Mouse ExE ortholog |
| chr22: 19967279-19967808 | 0 | Mouse ExE ortholog |
| chr22: 29709281-29712013 | 0 | Mouse ExE ortholog |
| chr22: 31198491-31199033 | 1 | Mouse ExE ortholog |
| chr22: 31500396-31501239 | 12 | Mouse ExE ortholog |
| chr22: 37212769-37213467 | 0 | Mouse ExE ortholog |
| chr22: 37911979-37912258 | 1 | Mouse ExE ortholog |
| chr22: 38476836-38478839 | 6 | Mouse ExE ortholog |
| chr22: 42305617-42307254 | 0 | Mouse ExE ortholog |
| chr22: 42322043-42322909 | 3 | Mouse ExE ortholog |
| chr22: 44726724-44727590 | 1 | Mouse ExE ortholog |
| chr22: 46318693-46319087 | 1 | Mouse ExE ortholog |
| chr22: 46440393-46441019 | 1 | Mouse ExE ortholog |
| chr3: 3840513-3842772 | 8 | Mouse ExE ortholog |
| chr3: 6902823-6903516 | 13 | Mouse ExE ortholog |
| chr3: 13114627-13115245 | 11 | Mouse ExE ortholog |
| chr3: 19189688-19190100 | 6 | Mouse ExE ortholog |
| chr3: 49947621-49948430 | 2 | Mouse ExE ortholog |
| chr3: 55508336-55508708 | 4 | Mouse ExE ortholog |
| chr3: 62354291-62355012 | 13 | Mouse ExE ortholog |
| chr3: 62357639-62359774 | 11 | Mouse ExE ortholog |
| chr3: 71834068-71834653 | 4 | Mouse ExE ortholog |
| chr3: 87841796-87842563 | 6 | Mouse ExE ortholog |
| chr3: 137482964-137484454 | 7 | Mouse ExE ortholog |
| chr3: 137489594-137491004 | 10 | Mouse ExE ortholog |
| chr3: 147108511-147111703 | 13 | Mouse ExE ortholog |
| chr3: 147113608-147114479 | 15 | Mouse ExE ortholog |
| chr3: 147130342-147130577 | 15 | Mouse ExE ortholog |
| chr3: 147131066-147131333 | 14 | Mouse ExE ortholog |
| chr3: 154146347-154146965 | 13 | Mouse ExE ortholog |
| chr3: 157821232-157821604 | 15 | Mouse ExE ortholog |
| chr3: 170303044-170303249 | 12 | Mouse ExE ortholog |
| chr3: 172165372-172166738 | 14 | Mouse ExE ortholog |
| chr4: 4868440-4869173 | 9 | Mouse ExE ortholog |
| chr4: 25090106-25090510 | 12 | Mouse ExE ortholog |
| chr4: 41749184-41749811 | 13 | Mouse ExE ortholog |
| chr4: 47034427-47034940 | 7 | Mouse ExE ortholog |
| chr4: 54966163-54968063 | 3 | Mouse ExE ortholog |
| chr4: 81119095-81119391 | 11 | Mouse ExE ortholog |
| chr4: 90228714-90229010 | 1 | Mouse ExE ortholog |
| chr4: 94755786-94756310 | 13 | Mouse ExE ortholog |
| chr4: 100870377-100871994 | 0 | Mouse ExE ortholog |

TABLE 1-continued

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
|---|---|---|
| chr4: 107956555-107957453 | 11 | Mouse ExE ortholog |
| chr4: 109093038-109094546 | 3 | Mouse ExE ortholog |
| chr4: 114900355-114900810 | 2 | Mouse ExE ortholog |
| chr4: 122301567-122302290 | 10 | Mouse ExE ortholog |
| chr4: 128544031-128544903 | 10 | Mouse ExE ortholog |
| chr4: 144620822-144622218 | 9 | Mouse ExE ortholog |
| chr4: 147559205-147561901 | 14 | Mouse ExE ortholog |
| chr4: 156680095-156681386 | 6 | Mouse ExE ortholog |
| chr4: 164264821-164265772 | 10 | Mouse ExE ortholog |
| chr4: 172733734-172735118 | 11 | Mouse ExE ortholog |
| chr4: 174430386-174430861 | 14 | Mouse ExE ortholog |
| chr4: 185939222-185942747 | 4 | Mouse ExE ortholog |
| chr5: 1879689-1879928 | 10 | Mouse ExE ortholog |
| chr5: 1881924-1887743 | 8 | Mouse ExE ortholog |
| chr5: 2748368-2757024 | 7 | Mouse ExE ortholog |
| chr5: 37834671-37835128 | 12 | Mouse ExE ortholog |
| chr5: 38257825-38259136 | 4 | Mouse ExE ortholog |
| chr5: 52777788-52777996 | 0 | Mouse ExE ortholog |
| chr5: 54527319-54527760 | 0 | Mouse ExE ortholog |
| chr5: 59189046-59189894 | 7 | Mouse ExE ortholog |
| chr5: 63256548-63257886 | 12 | Mouse ExE ortholog |
| chr5: 71014917-71015715 | 13 | Mouse ExE ortholog |
| chr5: 72529099-72529976 | 7 | Mouse ExE ortholog |
| chr5: 76932317-76933523 | 10 | Mouse ExE ortholog |
| chr5: 76934581-76935296 | 12 | Mouse ExE ortholog |
| chr5: 77805753-77806313 | 2 | Mouse ExE ortholog |
| chr5: 92923487-92924497 | 14 | Mouse ExE ortholog |
| chr5: 92939795-92940216 | 12 | Mouse ExE ortholog |
| chr5: 134363092-134365146 | 12 | Mouse ExE ortholog |
| chr5: 134366913-134367438 | 7 | Mouse ExE ortholog |
| chr5: 134374385-134376751 | 3 | Mouse ExE ortholog |
| chr5: 139138875-139139242 | 4 | Mouse ExE ortholog |
| chr5: 140052059-140053381 | 0 | Mouse ExE ortholog |
| chr5: 140305712-140307193 | 10 | Mouse ExE ortholog |
| chr5: 140798757-140799359 | 15 | Mouse ExE ortholog |
| chr5: 140810494-140812617 | 15 | Mouse ExE ortholog |
| chr5: 145718289-145720095 | 11 | Mouse ExE ortholog |
| chr5: 145725286-145725852 | 13 | Mouse ExE ortholog |
| chr5: 158523906-158524598 | 7 | Mouse ExE ortholog |
| chr5: 172665306-172666072 | 4 | Mouse ExE ortholog |
| chr5: 179228283-179229003 | 9 | Mouse ExE ortholog |
| chr6: 391188-393790 | 13 | Mouse ExE ortholog |
| chr6: 1381743-1385211 | 6 | Mouse ExE ortholog |
| chr6: 5997027-5997414 | 2 | Mouse ExE ortholog |
| chr6: 6007387-6007797 | 4 | Mouse ExE ortholog |
| chr6: 7229877-7230865 | 0 | Mouse ExE ortholog |
| chr6: 10390038-10390565 | 8 | Mouse ExE ortholog |
| chr6: 29894140-29895117 | 13 | Mouse ExE ortholog |
| chr6: 33393592-33393908 | 0 | Mouse ExE ortholog |
| chr6: 33655966-33656238 | 1 | Mouse ExE ortholog |
| chr6: 41908745-41909711 | 0 | Mouse ExE ortholog |
| chr6: 42072032-42072701 | 10 | Mouse ExE ortholog |
| chr6: 46655262-46656738 | 0 | Mouse ExE ortholog |
| chr6: 50682334-50683214 | 14 | Mouse ExE ortholog |
| chr6: 50791110-50791573 | 12 | Mouse ExE ortholog |
| chr6: 55039170-55039392 | 12 | Mouse ExE ortholog |
| chr6: 99275763-99276038 | 7 | Mouse ExE ortholog |
| chr6: 101846766-101847135 | 11 | Mouse ExE ortholog |
| chr6: 108485671-108490539 | 12 | Mouse ExE ortholog |
| chr6: 108491033-108491410 | 12 | Mouse ExE ortholog |
| chr6: 108497595-108497996 | 9 | Mouse ExE ortholog |
| chr6: 117198089-117198705 | 3 | Mouse ExE ortholog |
| chr6: 117591533-117592279 | 9 | Mouse ExE ortholog |
| chr6: 134210639-134211218 | 10 | Mouse ExE ortholog |
| chr6: 134638797-134639021 | 5 | Mouse ExE ortholog |
| chr6: 137242315-137245442 | 0 | Mouse ExE ortholog |
| chr6: 137814355-137815202 | 13 | Mouse ExE ortholog |
| chr6: 138745348-138745593 | 0 | Mouse ExE ortholog |
| chr7: 1362811-1363643 | 0 | Mouse ExE ortholog |
| chr7: 6590563-6590957 | 2 | Mouse ExE ortholog |
| chr7: 6661875-6662695 | 0 | Mouse ExE ortholog |
| chr7: 19145872-19146256 | 12 | Mouse ExE ortholog |
| chr7: 20370003-20371504 | 0 | Mouse ExE ortholog |
| chr7: 20830567-20830817 | 6 | Mouse ExE ortholog |
| chr7: 26415746-26416891 | 2 | Mouse ExE ortholog |
| chr7: 27146069-27146600 | 13 | Mouse ExE ortholog |
| chr7: 27182613-27185562 | 8 | Mouse ExE ortholog |
| chr7: 27227520-27229043 | 3 | Mouse ExE ortholog |
| chr7: 27278945-27279469 | 13 | Mouse ExE ortholog |
| chr7: 27282086-27283136 | 7 | Mouse ExE ortholog |
| chr7: 30721372-30722445 | 12 | Mouse ExE ortholog |
| chr7: 37955622-37956555 | 2 | Mouse ExE ortholog |
| chr7: 49813008-49815752 | 11 | Mouse ExE ortholog |
| chr7: 56355508-56355798 | 13 | Mouse ExE ortholog |
| chr7: 87563342-87564571 | 0 | Mouse ExE ortholog |
| chr7: 90893567-90896683 | 0 | Mouse ExE ortholog |
| chr7: 95225503-95226194 | 2 | Mouse ExE ortholog |
| chr7: 96650221-96651551 | 12 | Mouse ExE ortholog |
| chr7: 96651963-96652246 | 10 | Mouse ExE ortholog |
| chr7: 97841636-97842005 | 0 | Mouse ExE ortholog |
| chr7: 113724924-113727795 | 1 | Mouse ExE ortholog |
| chr7: 130790358-130792773 | 0 | Mouse ExE ortholog |
| chr7: 136553854-136556194 | 12 | Mouse ExE ortholog |
| chr7: 155595692-155599414 | 6 | Mouse ExE ortholog |
| chr7: 155604725-155605095 | 3 | Mouse ExE ortholog |
| chr7: 156795355-156799394 | 11 | Mouse ExE ortholog |
| chr8: 21905461-21905757 | 6 | Mouse ExE ortholog |
| chr8: 25900562-25905842 | 3 | Mouse ExE ortholog |
| chr8: 55366180-55367628 | 11 | Mouse ExE ortholog |
| chr8: 65710990-65711722 | 6 | Mouse ExE ortholog |
| chr8: 70981873-70984888 | 14 | Mouse ExE ortholog |
| chr8: 105478672-105479340 | 13 | Mouse ExE ortholog |
| chr8: 120428398-120429178 | 1 | Mouse ExE ortholog |
| chr8: 143545445-143546178 | 5 | Mouse ExE ortholog |
| chr8: 144808221-144810978 | 1 | Mouse ExE ortholog |
| chr8: 144990270-145002135 | 0 | Mouse ExE ortholog |
| chr9: 17906419-17907488 | 11 | Mouse ExE ortholog |
| chr9: 21970913-21971190 | 1 | Mouse ExE ortholog |
| chr9: 22005887-22006229 | 0 | Mouse ExE ortholog |
| chr9: 86152353-86153777 | 0 | Mouse ExE ortholog |
| chr9: 95477296-95477708 | 5 | Mouse ExE ortholog |
| chr9: 96713326-96718186 | 9 | Mouse ExE ortholog |
| chr9: 97401286-97402067 | 0 | Mouse ExE ortholog |
| chr9: 102590742-102591303 | 12 | Mouse ExE ortholog |
| chr9: 112081402-112082905 | 1 | Mouse ExE ortholog |
| chr9: 120175253-120177496 | 8 | Mouse ExE ortholog |
| chr9: 122131086-122132214 | 11 | Mouse ExE ortholog |
| chr9: 124413512-124414193 | 0 | Mouse ExE ortholog |
| chr9: 124987743-124991086 | 4 | Mouse ExE ortholog |
| chr9: 126773246-126780953 | 8 | Mouse ExE ortholog |
| chr9: 129372737-129378106 | 3 | Mouse ExE ortholog |
| chr9: 129386112-129389231 | 7 | Mouse ExE ortholog |
| chr9: 131154346-131155923 | 2 | Mouse ExE ortholog |
| chr9: 132459587-132460017 | 4 | Mouse ExE ortholog |
| chr9: 133534534-133542394 | 9 | Mouse ExE ortholog |
| chr9: 135039673-135039978 | 3 | Mouse ExE ortholog |
| chr9: 135455164-135458586 | 4 | Mouse ExE ortholog |
| chr9: 135461934-135462909 | 13 | Mouse ExE ortholog |
| chr9: 135464586-135466240 | 6 | Mouse ExE ortholog |
| chr9: 139096665-139096993 | 6 | Mouse ExE ortholog |
| chr9: 139396205-139397040 | 0 | Mouse ExE ortholog |
| chrX: 67352650-67352923 | 0 | Mouse ExE ortholog |
| chrX: 99891299-99891794 | 0 | Mouse ExE ortholog |
| chrX: 152612775-152613464 | 0 | Mouse ExE ortholog |
| chr1: 1474962-1475220 | 14 | Human Placenta |
| chr1: 2979275-2980758 | 8 | Human Placenta |
| chr1: 10764429-10764925 | 9 | Human Placenta |
| chr1: 12123488-12124148 | 8 | Human Placenta |
| chr1: 16860873-16862296 | 14 | Human Placenta |
| chr1: 18964180-18964401 | 9 | Human Placenta |
| chr1: 24229115-24229537 | 14 | Human Placenta |
| chr1: 32052471-32052771 | 9 | Human Placenta |

TABLE 1-continued

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
|---|---|---|
| chr1: 34642382-34643024 | 14 | Human Placenta |
| chr1: 36549554-36549965 | 11 | Human Placenta |
| chr1: 38219702-38220012 | 9 | Human Placenta |
| chr1: 38461584-38461988 | 8 | Human Placenta |
| chr1: 38941919-38942404 | 11 | Human Placenta |
| chr1: 39044059-39044561 | 8 | Human Placenta |
| chr1: 40769186-40769871 | 9 | Human Placenta |
| chr1: 41284847-41285149 | 9 | Human Placenta |
| chr1: 44031286-44031853 | 14 | Human Placenta |
| chr1: 47009575-47010132 | 13 | Human Placenta |
| chr1: 50880916-50881516 | 14 | Human Placenta |
| chr1: 50881884-50882103 | 12 | Human Placenta |
| chr1: 50892437-50893243 | 10 | Human Placenta |
| chr1: 53527572-53528974 | 9 | Human Placenta |
| chr1: 63795363-63796140 | 13 | Human Placenta |
| chr1: 65991001-65991811 | 11 | Human Placenta |
| chr1: 67218079-67218293 | 14 | Human Placenta |
| chr1: 67773329-67773767 | 9 | Human Placenta |
| chr1: 86621278-86622871 | 8 | Human Placenta |
| chr1: 91183240-91184540 | 15 | Human Placenta |
| chr1: 91185156-91185577 | 15 | Human Placenta |
| chr1: 91190489-91192804 | 11 | Human Placenta |
| chr1: 91300979-91301891 | 15 | Human Placenta |
| chr1: 110610265-110613303 | 11 | Human Placenta |
| chr1: 113265573-113265787 | 8 | Human Placenta |
| chr1: 113286332-113287172 | 9 | Human Placenta |
| chr1: 114695136-114696672 | 10 | Human Placenta |
| chr1: 119526782-119527192 | 15 | Human Placenta |
| chr1: 119529819-119530712 | 13 | Human Placenta |
| chr1: 119543056-119543454 | 14 | Human Placenta |
| chr1: 119549144-119551320 | 13 | Human Placenta |
| chr1: 145075483-145075845 | 13 | Human Placenta |
| chr1: 146552328-146552577 | 13 | Human Placenta |
| chr1: 147782066-147782473 | 13 | Human Placenta |
| chr1: 149332993-149333389 | 14 | Human Placenta |
| chr1: 155147185-155147444 | 9 | Human Placenta |
| chr1: 155264318-155265536 | 14 | Human Placenta |
| chr1: 155290606-155291001 | 10 | Human Placenta |
| chr1: 156863415-156863711 | 14 | Human Placenta |
| chr1: 164545540-164545917 | 12 | Human Placenta |
| chr1: 165324191-165326328 | 11 | Human Placenta |
| chr1: 170630456-170630851 | 13 | Human Placenta |
| chr1: 173638662-173639045 | 12 | Human Placenta |
| chr1: 175568376-175568808 | 12 | Human Placenta |
| chr1: 179544720-179545307 | 8 | Human Placenta |
| chr1: 181287300-181287873 | 8 | Human Placenta |
| chr1: 181452706-181453073 | 9 | Human Placenta |
| chr1: 200009807-200010036 | 8 | Human Placenta |
| chr1: 202162958-202163390 | 12 | Human Placenta |
| chr1: 203044722-203045390 | 12 | Human Placenta |
| chr1: 208132327-208133117 | 11 | Human Placenta |
| chr1: 214153214-214153668 | 13 | Human Placenta |
| chr1: 217310749-217311178 | 14 | Human Placenta |
| chr1: 221050448-221050864 | 13 | Human Placenta |
| chr1: 221060850-221061071 | 10 | Human Placenta |
| chr1: 225865068-225865328 | 12 | Human Placenta |
| chr1: 226127112-226127695 | 12 | Human Placenta |
| chr1: 228785986-228786204 | 15 | Human Placenta |
| chr1: 231296559-231297345 | 12 | Human Placenta |
| chr1: 243646394-243646888 | 9 | Human Placenta |
| chr10: 1778784-1780018 | 8 | Human Placenta |
| chr10: 8076002-8077261 | 8 | Human Placenta |
| chr10: 8077829-8078378 | 12 | Human Placenta |
| chr10: 15761423-15762101 | 13 | Human Placenta |
| chr10: 16561604-16563822 | 10 | Human Placenta |
| chr10: 22623350-22625875 | 9 | Human Placenta |
| chr10: 22634000-22634862 | 15 | Human Placenta |
| chr10: 22764708-22767050 | 12 | Human Placenta |
| chr10: 23461300-23461610 | 14 | Human Placenta |
| chr10: 23462224-23463889 | 12 | Human Placenta |
| chr10: 23480697-23482455 | 12 | Human Placenta |
| chr10: 23983366-23984978 | 10 | Human Placenta |
| chr10: 26504383-26507434 | 11 | Human Placenta |
| chr10: 27547668-27548402 | 9 | Human Placenta |
| chr10: 43428167-43429460 | 8 | Human Placenta |
| chr10: 48438411-48439320 | 11 | Human Placenta |
| chr10: 63212495-63213009 | 9 | Human Placenta |
| chr10: 71331449-71331691 | 13 | Human Placenta |
| chr10: 75407413-75407706 | 11 | Human Placenta |
| chr10: 76573195-76573507 | 15 | Human Placenta |
| chr10: 94180315-94180754 | 13 | Human Placenta |
| chr10: 94455524-94455896 | 8 | Human Placenta |
| chr10: 94828102-94829040 | 13 | Human Placenta |
| chr10: 99789614-99791320 | 8 | Human Placenta |
| chr10: 100992156-100992687 | 12 | Human Placenta |
| chr10: 101282725-101282934 | 8 | Human Placenta |
| chr10: 101290025-101290338 | 14 | Human Placenta |
| chr10: 102279162-102279730 | 12 | Human Placenta |
| chr10: 102475276-102475579 | 8 | Human Placenta |
| chr10: 102891010-102891794 | 12 | Human Placenta |
| chr10: 102905714-102906693 | 11 | Human Placenta |
| chr10: 102996034-102996646 | 12 | Human Placenta |
| chr10: 103043990-103044480 | 12 | Human Placenta |
| chr10: 108923780-108924805 | 12 | Human Placenta |
| chr10: 109674196-109674964 | 13 | Human Placenta |
| chr10: 110671724-110672326 | 12 | Human Placenta |
| chr10: 111216604-111217083 | 12 | Human Placenta |
| chr10: 118030732-118034230 | 9 | Human Placenta |
| chr10: 118892161-118892639 | 12 | Human Placenta |
| chr10: 118893527-118894432 | 12 | Human Placenta |
| chr10: 119494493-119494991 | 10 | Human Placenta |
| chr10: 120353692-120355821 | 12 | Human Placenta |
| chr10: 121577529-121578385 | 15 | Human Placenta |
| chr10: 123922850-123923542 | 13 | Human Placenta |
| chr10: 124901907-124902617 | 12 | Human Placenta |
| chr10: 125425495-125426642 | 14 | Human Placenta |
| chr10: 125650820-125651373 | 11 | Human Placenta |
| chr10: 125732220-125732843 | 14 | Human Placenta |
| chr10: 130338695-130338994 | 12 | Human Placenta |
| chr10: 130508443-130508658 | 10 | Human Placenta |
| chr10: 134597357-134602649 | 11 | Human Placenta |
| chr11: 626728-628037 | 9 | Human Placenta |
| chr11: 636435-636668 | 9 | Human Placenta |
| chr11: 636906-640628 | 8 | Human Placenta |
| chr11: 2890388-2891337 | 8 | Human Placenta |
| chr11: 14995128-14995908 | 10 | Human Placenta |
| chr11: 20618197-20619920 | 14 | Human Placenta |
| chr11: 27743472-27744564 | 12 | Human Placenta |
| chr11: 31827696-31827921 | 14 | Human Placenta |
| chr11: 31841315-31842003 | 14 | Human Placenta |
| chr11: 31847132-31847958 | 13 | Human Placenta |
| chr11: 43568921-43569854 | 10 | Human Placenta |
| chr11: 44325657-44326517 | 9 | Human Placenta |
| chr11: 60718428-60718888 | 9 | Human Placenta |
| chr11: 64478843-64479598 | 14 | Human Placenta |
| chr11: 64815040-64815722 | 13 | Human Placenta |
| chr11: 65409636-65410127 | 13 | Human Placenta |
| chr11: 65816404-65816665 | 14 | Human Placenta |
| chr11: 68622108-68622339 | 9 | Human Placenta |
| chr11: 70508328-70508617 | 9 | Human Placenta |
| chr11: 71952112-71952528 | 11 | Human Placenta |
| chr11: 88241710-88242562 | 10 | Human Placenta |
| chr11: 89224416-89224718 | 11 | Human Placenta |
| chr11: 105481126-105481422 | 12 | Human Placenta |
| chr11: 115630398-115631117 | 8 | Human Placenta |
| chr11: 119293320-119293943 | 13 | Human Placenta |
| chr11: 123066517-123066986 | 13 | Human Placenta |
| chr11: 128419198-128419513 | 10 | Human Placenta |
| chr11: 128694084-128694688 | 8 | Human Placenta |
| chr11: 131780328-131781532 | 12 | Human Placenta |
| chr11: 132813562-132814395 | 9 | Human Placenta |
| chr11: 132934059-132934291 | 11 | Human Placenta |

TABLE 1-continued

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
| --- | --- | --- |
| chr11: 132952538-132953307 | 8 | Human Placenta |
| chr11: 133994709-133995090 | 9 | Human Placenta |
| chr12: 186863-187610 | 9 | Human Placenta |
| chr12: 3308812-3310270 | 8 | Human Placenta |
| chr12: 5153012-5154346 | 9 | Human Placenta |
| chr12: 14134626-14135242 | 8 | Human Placenta |
| chr12: 41086522-41087102 | 9 | Human Placenta |
| chr12: 48399168-48399372 | 8 | Human Placenta |
| chr12: 52115410-52115679 | 11 | Human Placenta |
| chr12: 52408381-52408675 | 13 | Human Placenta |
| chr12: 52652018-52652743 | 13 | Human Placenta |
| chr12: 53107912-53108471 | 10 | Human Placenta |
| chr12: 53359192-53359507 | 12 | Human Placenta |
| chr12: 54071053-54071265 | 10 | Human Placenta |
| chr12: 54321301-54321721 | 12 | Human Placenta |
| chr12: 54354529-54355491 | 12 | Human Placenta |
| chr12: 54359658-54359906 | 12 | Human Placenta |
| chr12: 54424610-54425173 | 8 | Human Placenta |
| chr12: 65218245-65219143 | 8 | Human Placenta |
| chr12: 65514878-65515863 | 9 | Human Placenta |
| chr12: 72665683-72667551 | 10 | Human Placenta |
| chr12: 81102034-81102716 | 14 | Human Placenta |
| chr12: 81471569-81472119 | 10 | Human Placenta |
| chr12: 103696090-103696418 | 13 | Human Placenta |
| chr12: 104697348-104697984 | 11 | Human Placenta |
| chr12: 106974412-106974951 | 11 | Human Placenta |
| chr12: 113013099-113013529 | 14 | Human Placenta |
| chr12: 113515164-113515970 | 9 | Human Placenta |
| chr12: 113916433-113916717 | 14 | Human Placenta |
| chr12: 114833911-114834210 | 9 | Human Placenta |
| chr12: 114838312-114838889 | 8 | Human Placenta |
| chr12: 114843022-114843610 | 10 | Human Placenta |
| chr12: 114845861-114847650 | 14 | Human Placenta |
| chr12: 114851957-114852360 | 9 | Human Placenta |
| chr12: 114881649-114881937 | 10 | Human Placenta |
| chr12: 114885105-114885418 | 13 | Human Placenta |
| chr12: 119212110-119212393 | 10 | Human Placenta |
| chr12: 123754049-123754373 | 14 | Human Placenta |
| chr12: 127210778-127211651 | 14 | Human Placenta |
| chr12: 127940451-127940907 | 14 | Human Placenta |
| chr12: 129337870-129338653 | 11 | Human Placenta |
| chr12: 131199824-131200157 | 8 | Human Placenta |
| chr12: 132905449-132906206 | 9 | Human Placenta |
| chr13: 20875518-20876214 | 9 | Human Placenta |
| chr13: 28366549-28368505 | 9 | Human Placenta |
| chr13: 28549839-28550246 | 13 | Human Placenta |
| chr13: 36044844-36045481 | 13 | Human Placenta |
| chr13: 51417371-51418149 | 14 | Human Placenta |
| chr13: 53419897-53422872 | 13 | Human Placenta |
| chr13: 58203586-58204322 | 11 | Human Placenta |
| chr13: 58206526-58208930 | 14 | Human Placenta |
| chr13: 79181944-79182222 | 14 | Human Placenta |
| chr13: 93879245-93880877 | 8 | Human Placenta |
| chr13: 100547633-100548911 | 8 | Human Placenta |
| chr13: 100641334-100642188 | 12 | Human Placenta |
| chr13: 102568425-102569495 | 10 | Human Placenta |
| chr13: 112707804-112708696 | 13 | Human Placenta |
| chr13: 112709884-112712665 | 14 | Human Placenta |
| chr13: 112715359-112716234 | 10 | Human Placenta |
| chr13: 112717125-112717421 | 14 | Human Placenta |
| chr13: 112720564-112723582 | 14 | Human Placenta |
| chr13: 112726281-112728248 | 11 | Human Placenta |
| chr13: 112758598-112760491 | 14 | Human Placenta |
| chr13: 112760865-112761113 | 8 | Human Placenta |
| chr14: 24044886-24046760 | 8 | Human Placenta |
| chr14: 24641053-24642220 | 13 | Human Placenta |
| chr14: 24803678-24804353 | 12 | Human Placenta |
| chr14: 29236835-29237832 | 15 | Human Placenta |
| chr14: 29254365-29255069 | 14 | Human Placenta |
| chr14: 33402094-33404079 | 8 | Human Placenta |
| chr14: 36973169-36973740 | 13 | Human Placenta |
| chr14: 36983440-36983738 | 11 | Human Placenta |
| chr14: 36990873-36991209 | 12 | Human Placenta |
| chr14: 36993488-36994488 | 9 | Human Placenta |
| chr14: 37053134-37053690 | 14 | Human Placenta |
| chr14: 37126786-37128274 | 8 | Human Placenta |
| chr14: 37135513-37136348 | 10 | Human Placenta |
| chr14: 38724254-38725537 | 15 | Human Placenta |
| chr14: 48143433-48145589 | 13 | Human Placenta |
| chr14: 51338712-51339146 | 11 | Human Placenta |
| chr14: 52734207-52735486 | 12 | Human Placenta |
| chr14: 57260878-57262123 | 12 | Human Placenta |
| chr14: 57264638-57265561 | 12 | Human Placenta |
| chr14: 57278709-57279116 | 14 | Human Placenta |
| chr14: 58331676-58333121 | 11 | Human Placenta |
| chr14: 60973772-60974123 | 13 | Human Placenta |
| chr14: 60975732-60978180 | 12 | Human Placenta |
| chr14: 61103978-61104663 | 12 | Human Placenta |
| chr14: 62279476-62280019 | 9 | Human Placenta |
| chr14: 77736733-77737772 | 11 | Human Placenta |
| chr14: 85997468-85998637 | 10 | Human Placenta |
| chr14: 85999532-86000478 | 8 | Human Placenta |
| chr14: 92789494-92790712 | 9 | Human Placenta |
| chr14: 95239375-95239679 | 14 | Human Placenta |
| chr14: 95826675-95826941 | 9 | Human Placenta |
| chr14: 101192851-101193499 | 11 | Human Placenta |
| chr14: 101923575-101925995 | 11 | Human Placenta |
| chr14: 103655241-103655928 | 11 | Human Placenta |
| chr15: 23157794-23158624 | 12 | Human Placenta |
| chr15: 27112030-27113479 | 12 | Human Placenta |
| chr15: 27215951-27216856 | 12 | Human Placenta |
| chr15: 33602816-33604003 | 10 | Human Placenta |
| chr15: 35046443-35047480 | 12 | Human Placenta |
| chr15: 37390175-37390380 | 13 | Human Placenta |
| chr15: 53076187-53077926 | 11 | Human Placenta |
| chr15: 53079220-53079579 | 13 | Human Placenta |
| chr15: 53080458-53083699 | 12 | Human Placenta |
| chr15: 53087211-53087488 | 9 | Human Placenta |
| chr15: 53097561-53098476 | 13 | Human Placenta |
| chr15: 59157045-59157594 | 11 | Human Placenta |
| chr15: 76630029-76630970 | 11 | Human Placenta |
| chr15: 79574830-79575211 | 8 | Human Placenta |
| chr15: 89147660-89149198 | 9 | Human Placenta |
| chr15: 89312719-89313183 | 8 | Human Placenta |
| chr15: 89903446-89903720 | 12 | Human Placenta |
| chr15: 89910521-89912177 | 8 | Human Placenta |
| chr15: 89952271-89953061 | 11 | Human Placenta |
| chr15: 96895306-96895729 | 8 | Human Placenta |
| chr15: 96903311-96903711 | 9 | Human Placenta |
| chr15: 96904722-96905050 | 9 | Human Placenta |
| chr15: 96909815-96910030 | 8 | Human Placenta |
| chr15: 96959341-96960531 | 8 | Human Placenta |
| chr15: 100913438-100914022 | 10 | Human Placenta |
| chr16: 3067521-3068358 | 9 | Human Placenta |
| chr16: 3220438-3221356 | 9 | Human Placenta |
| chr16: 6068914-6070401 | 11 | Human Placenta |
| chr16: 10912159-10912719 | 10 | Human Placenta |
| chr16: 20084707-20085305 | 9 | Human Placenta |
| chr16: 23724270-23724775 | 8 | Human Placenta |
| chr16: 24267040-24267527 | 8 | Human Placenta |
| chr16: 31053479-31053800 | 11 | Human Placenta |
| chr16: 49309123-49309353 | 13 | Human Placenta |
| chr16: 49316997-49317263 | 11 | Human Placenta |
| chr16: 51183699-51188763 | 10 | Human Placenta |
| chr16: 54325040-54325703 | 10 | Human Placenta |
| chr16: 55364823-55365483 | 8 | Human Placenta |
| chr16: 66612749-66613412 | 10 | Human Placenta |
| chr16: 67918679-67918909 | 8 | Human Placenta |
| chr16: 71459781-71460338 | 13 | Human Placenta |
| chr16: 82660651-82661813 | 10 | Human Placenta |
| chr16: 84002269-84002860 | 8 | Human Placenta |
| chr17: 934417-935088 | 11 | Human Placenta |

TABLE 1-continued

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
| --- | --- | --- |
| chr17: 1173535-1174733 | 10 | Human Placenta |
| chr17: 1880789-1881116 | 9 | Human Placenta |
| chr17: 5000369-5001205 | 15 | Human Placenta |
| chr17: 6616422-6617471 | 10 | Human Placenta |
| chr17: 6679205-6679710 | 13 | Human Placenta |
| chr17: 7832532-7833164 | 13 | Human Placenta |
| chr17: 7905927-7907445 | 9 | Human Placenta |
| chr17: 12877270-12877773 | 8 | Human Placenta |
| chr17: 14201726-14202052 | 13 | Human Placenta |
| chr17: 15820620-15821325 | 14 | Human Placenta |
| chr17: 19883325-19883610 | 11 | Human Placenta |
| chr17: 21367114-21367592 | 9 | Human Placenta |
| chr17: 27899511-27900067 | 11 | Human Placenta |
| chr17: 33776553-33776888 | 12 | Human Placenta |
| chr17: 36717727-36718593 | 11 | Human Placenta |
| chr17: 37321482-37322099 | 9 | Human Placenta |
| chr17: 43037166-43037740 | 12 | Human Placenta |
| chr17: 46604362-46604881 | 9 | Human Placenta |
| chr17: 46627787-46628444 | 8 | Human Placenta |
| chr17: 46673532-46674181 | 10 | Human Placenta |
| chr17: 46697413-46697701 | 8 | Human Placenta |
| chr17: 46796234-46797292 | 11 | Human Placenta |
| chr17: 46800533-46800746 | 10 | Human Placenta |
| chr17: 46824785-46825372 | 12 | Human Placenta |
| chr17: 48041282-48043064 | 10 | Human Placenta |
| chr17: 48545570-48546900 | 11 | Human Placenta |
| chr17: 59531723-59535254 | 8 | Human Placenta |
| chr17: 70111979-70112308 | 12 | Human Placenta |
| chr17: 70112824-70114271 | 12 | Human Placenta |
| chr17: 71948478-71949255 | 8 | Human Placenta |
| chr17: 73749618-73750178 | 11 | Human Placenta |
| chr17: 74533281-74534566 | 8 | Human Placenta |
| chr18: 904578-909574 | 13 | Human Placenta |
| chr18: 11148307-11149936 | 13 | Human Placenta |
| chr18: 11750953-11752756 | 9 | Human Placenta |
| chr18: 12254147-12255089 | 8 | Human Placenta |
| chr18: 13641584-13642415 | 8 | Human Placenta |
| chr18: 13868532-13869026 | 12 | Human Placenta |
| chr18: 43608140-43608510 | 10 | Human Placenta |
| chr18: 44336183-44337110 | 11 | Human Placenta |
| chr18: 44337510-44338100 | 10 | Human Placenta |
| chr18: 44772992-44775577 | 15 | Human Placenta |
| chr18: 44777632-44778084 | 14 | Human Placenta |
| chr18: 44789742-44790678 | 14 | Human Placenta |
| chr18: 54788959-54789194 | 12 | Human Placenta |
| chr18: 55019707-55021605 | 15 | Human Placenta |
| chr18: 55094825-55096310 | 14 | Human Placenta |
| chr18: 56887091-56887665 | 9 | Human Placenta |
| chr18: 56939624-56941540 | 10 | Human Placenta |
| chr18: 70533965-70536871 | 11 | Human Placenta |
| chr18: 72916107-72917233 | 10 | Human Placenta |
| chr18: 73167402-73167920 | 12 | Human Placenta |
| chr18: 74799144-74800038 | 10 | Human Placenta |
| chr18: 76732970-76734765 | 11 | Human Placenta |
| chr18: 76737005-76741244 | 13 | Human Placenta |
| chr18: 77547965-77549038 | 14 | Human Placenta |
| chr18: 77557780-77558948 | 10 | Human Placenta |
| chr19: 870774-871318 | 10 | Human Placenta |
| chr19: 3868586-3869217 | 10 | Human Placenta |
| chr19: 5829048-5829474 | 8 | Human Placenta |
| chr19: 8674332-8674764 | 12 | Human Placenta |
| chr19: 10406934-10407342 | 9 | Human Placenta |
| chr19: 10463626-10464378 | 8 | Human Placenta |
| chr19: 12666243-12666682 | 9 | Human Placenta |
| chr19: 12767749-12767980 | 13 | Human Placenta |
| chr19: 12831793-12832225 | 10 | Human Placenta |
| chr19: 12880574-12880888 | 13 | Human Placenta |
| chr19: 13124959-13125259 | 9 | Human Placenta |
| chr19: 13616752-13617267 | 13 | Human Placenta |
| chr19: 14089570-14089796 | 14 | Human Placenta |
| chr19: 19371675-19372393 | 12 | Human Placenta |
| chr19: 21769189-21769786 | 10 | Human Placenta |
| chr19: 33625467-33625805 | 11 | Human Placenta |
| chr19: 36246328-36247982 | 9 | Human Placenta |
| chr19: 36523391-36523887 | 11 | Human Placenta |
| chr19: 38700333-38700577 | 8 | Human Placenta |
| chr19: 39737689-39739288 | 9 | Human Placenta |
| chr19: 39754973-39756540 | 11 | Human Placenta |
| chr19: 40314926-40315144 | 9 | Human Placenta |
| chr19: 44203558-44203987 | 12 | Human Placenta |
| chr19: 44278273-44278777 | 12 | Human Placenta |
| chr19: 45260352-45261809 | 8 | Human Placenta |
| chr19: 46001830-46002686 | 10 | Human Placenta |
| chr19: 46318490-46319266 | 12 | Human Placenta |
| chr19: 46915311-46915802 | 12 | Human Placenta |
| chr19: 47151768-47153125 | 9 | Human Placenta |
| chr19: 49669275-49669552 | 8 | Human Placenta |
| chr19: 51601822-51602260 | 9 | Human Placenta |
| chr19: 51815157-51815458 | 11 | Human Placenta |
| chr19: 54412710-54413087 | 13 | Human Placenta |
| chr19: 54481412-54481955 | 15 | Human Placenta |
| chr19: 54483021-54483572 | 9 | Human Placenta |
| chr19: 55597977-55598887 | 8 | Human Placenta |
| chr19: 56988313-56989741 | 12 | Human Placenta |
| chr19: 58094739-58095764 | 11 | Human Placenta |
| chr19: 58545115-58545897 | 13 | Human Placenta |
| chr19: 58554354-58554587 | 13 | Human Placenta |
| chr2: 467849-468659 | 14 | Human Placenta |
| chr2: 3286324-3286530 | 8 | Human Placenta |
| chr2: 5831187-5831413 | 15 | Human Placenta |
| chr2: 19560963-19561650 | 10 | Human Placenta |
| chr2: 20870006-20871280 | 14 | Human Placenta |
| chr2: 25499763-25500429 | 12 | Human Placenta |
| chr2: 31805293-31806403 | 12 | Human Placenta |
| chr2: 45169505-45171884 | 11 | Human Placenta |
| chr2: 45227644-45228783 | 8 | Human Placenta |
| chr2: 45240372-45241579 | 8 | Human Placenta |
| chr2: 54086776-54087266 | 13 | Human Placenta |
| chr2: 63282514-63283122 | 14 | Human Placenta |
| chr2: 63283936-63284147 | 13 | Human Placenta |
| chr2: 63285949-63287097 | 8 | Human Placenta |
| chr2: 66652691-66654218 | 9 | Human Placenta |
| chr2: 66672431-66673636 | 10 | Human Placenta |
| chr2: 80549578-80549798 | 10 | Human Placenta |
| chr2: 87015974-87018182 | 9 | Human Placenta |
| chr2: 87088816-87089037 | 11 | Human Placenta |
| chr2: 97192977-97193383 | 10 | Human Placenta |
| chr2: 105480197-105480760 | 13 | Human Placenta |
| chr2: 106681982-106682403 | 13 | Human Placenta |
| chr2: 107103833-107104053 | 11 | Human Placenta |
| chr2: 114033359-114033617 | 11 | Human Placenta |
| chr2: 114034594-114036041 | 9 | Human Placenta |
| chr2: 114256775-114258043 | 14 | Human Placenta |
| chr2: 118981769-118982466 | 10 | Human Placenta |
| chr2: 119592602-119593845 | 12 | Human Placenta |
| chr2: 119599059-119599299 | 14 | Human Placenta |
| chr2: 119602616-119604486 | 8 | Human Placenta |
| chr2: 119606569-119606826 | 10 | Human Placenta |
| chr2: 119611296-119611881 | 12 | Human Placenta |
| chr2: 119616133-119616826 | 13 | Human Placenta |
| chr2: 119914126-119916663 | 12 | Human Placenta |
| chr2: 124782252-124783255 | 11 | Human Placenta |
| chr2: 127413696-127414171 | 9 | Human Placenta |
| chr2: 127782613-127782829 | 14 | Human Placenta |
| chr2: 128421719-128422182 | 8 | Human Placenta |
| chr2: 130763483-130763764 | 13 | Human Placenta |
| chr2: 132182327-132183101 | 8 | Human Placenta |
| chr2: 139537692-139538650 | 10 | Human Placenta |
| chr2: 154727906-154728271 | 13 | Human Placenta |
| chr2: 154728944-154729328 | 12 | Human Placenta |
| chr2: 162279835-162280709 | 10 | Human Placenta |
| chr2: 162283581-162284677 | 13 | Human Placenta |

TABLE 1-continued

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
| --- | --- | --- |
| chr2: 171671598-171671804 | 13 | Human Placenta |
| chr2: 171678546-171680358 | 10 | Human Placenta |
| chr2: 176931575-176932663 | 9 | Human Placenta |
| chr2: 176936246-176936809 | 9 | Human Placenta |
| chr2: 176944087-176948446 | 8 | Human Placenta |
| chr2: 176949993-176950336 | 13 | Human Placenta |
| chr2: 176956504-176956707 | 11 | Human Placenta |
| chr2: 177012371-177012675 | 15 | Human Placenta |
| chr2: 177016416-177016632 | 11 | Human Placenta |
| chr2: 177024501-177025692 | 12 | Human Placenta |
| chr2: 198029068-198029438 | 14 | Human Placenta |
| chr2: 200333687-200334172 | 12 | Human Placenta |
| chr2: 207506774-207507422 | 13 | Human Placenta |
| chr2: 220173870-220174283 | 14 | Human Placenta |
| chr2: 223159725-223160487 | 10 | Human Placenta |
| chr2: 223162946-223163912 | 13 | Human Placenta |
| chr2: 223167205-223167560 | 10 | Human Placenta |
| chr2: 223168653-223169008 | 12 | Human Placenta |
| chr2: 223176493-223177515 | 13 | Human Placenta |
| chr2: 233251361-233253414 | 12 | Human Placenta |
| chr2: 237068071-237068834 | 11 | Human Placenta |
| chr2: 238864315-238865170 | 12 | Human Placenta |
| chr2: 241459632-241460047 | 15 | Human Placenta |
| chr20: 690575-691099 | 13 | Human Placenta |
| chr20: 2539133-2539877 | 9 | Human Placenta |
| chr20: 2729997-2730797 | 8 | Human Placenta |
| chr20: 2780978-2781497 | 13 | Human Placenta |
| chr20: 5296266-5297798 | 11 | Human Placenta |
| chr20: 9496471-9496893 | 9 | Human Placenta |
| chr20: 10198135-10198984 | 10 | Human Placenta |
| chr20: 17206528-17206952 | 11 | Human Placenta |
| chr20: 17208550-17208756 | 13 | Human Placenta |
| chr20: 21376358-21378245 | 14 | Human Placenta |
| chr20: 21694472-21695344 | 11 | Human Placenta |
| chr20: 22548967-22549720 | 11 | Human Placenta |
| chr20: 25063838-25065525 | 9 | Human Placenta |
| chr20: 32856659-32857248 | 8 | Human Placenta |
| chr20: 36012595-36013439 | 9 | Human Placenta |
| chr20: 36226617-36226841 | 12 | Human Placenta |
| chr20: 41817475-41819212 | 8 | Human Placenta |
| chr20: 48184193-48184833 | 8 | Human Placenta |
| chr20: 57089460-57090237 | 13 | Human Placenta |
| chr20: 57426729-57427047 | 9 | Human Placenta |
| chr20: 61703526-61704022 | 11 | Human Placenta |
| chr21: 19617098-19617874 | 12 | Human Placenta |
| chr21: 34395128-34400245 | 11 | Human Placenta |
| chr21: 38076762-38077685 | 8 | Human Placenta |
| chr21: 38079941-38081833 | 8 | Human Placenta |
| chr21: 42218489-42219222 | 10 | Human Placenta |
| chr22: 19746155-19746369 | 11 | Human Placenta |
| chr22: 25081850-25082112 | 8 | Human Placenta |
| chr22: 37465056-37465331 | 11 | Human Placenta |
| chr22: 38379093-38379964 | 14 | Human Placenta |
| chr22: 39262338-39263211 | 8 | Human Placenta |
| chr22: 42685894-42686095 | 11 | Human Placenta |
| chr22: 44257942-44258612 | 9 | Human Placenta |
| chr22: 44287497-44288061 | 8 | Human Placenta |
| chr22: 48884884-48887043 | 11 | Human Placenta |
| chr22: 50496441-50497393 | 11 | Human Placenta |
| chr3: 238891-240140 | 9 | Human Placenta |
| chr3: 6904133-6904641 | 13 | Human Placenta |
| chr3: 9177691-9178189 | 9 | Human Placenta |
| chr3: 11034446-11035384 | 9 | Human Placenta |
| chr3: 12838471-12838782 | 8 | Human Placenta |
| chr3: 22413492-22414365 | 13 | Human Placenta |
| chr3: 26664104-26664796 | 12 | Human Placenta |
| chr3: 27771638-27771942 | 9 | Human Placenta |
| chr3: 32861141-32861429 | 10 | Human Placenta |
| chr3: 44063314-44063837 | 10 | Human Placenta |
| chr3: 44596535-44597018 | 8 | Human Placenta |
| chr3: 46618307-46618669 | 12 | Human Placenta |
| chr3: 62356119-62356378 | 14 | Human Placenta |
| chr3: 62356773-62357315 | 13 | Human Placenta |
| chr3: 62362610-62363082 | 14 | Human Placenta |
| chr3: 63263989-63264205 | 14 | Human Placenta |
| chr3: 64253533-64253819 | 10 | Human Placenta |
| chr3: 75667777-75669067 | 12 | Human Placenta |
| chr3: 75955759-75956308 | 9 | Human Placenta |
| chr3: 113160299-113160641 | 11 | Human Placenta |
| chr3: 121902742-121903645 | 12 | Human Placenta |
| chr3: 126113547-126113967 | 14 | Human Placenta |
| chr3: 127633993-127634588 | 9 | Human Placenta |
| chr3: 127794369-127796136 | 9 | Human Placenta |
| chr3: 128719865-128721245 | 8 | Human Placenta |
| chr3: 129693127-129694841 | 12 | Human Placenta |
| chr3: 133393118-133393657 | 12 | Human Placenta |
| chr3: 138656627-138659107 | 9 | Human Placenta |
| chr3: 147126988-147128999 | 14 | Human Placenta |
| chr3: 147138916-147139564 | 15 | Human Placenta |
| chr3: 147142181-147142391 | 12 | Human Placenta |
| chr3: 157812053-157812764 | 15 | Human Placenta |
| chr3: 170303532-170303768 | 14 | Human Placenta |
| chr3: 184056419-184056671 | 12 | Human Placenta |
| chr3: 185911344-185912228 | 9 | Human Placenta |
| chr3: 186078710-186080111 | 8 | Human Placenta |
| chr3: 192125821-192127994 | 8 | Human Placenta |
| chr4: 107146-107898 | 15 | Human Placenta |
| chr4: 206377-206892 | 15 | Human Placenta |
| chr4: 682724-683079 | 9 | Human Placenta |
| chr4: 961347-962155 | 14 | Human Placenta |
| chr4: 4859632-4860191 | 14 | Human Placenta |
| chr4: 5709985-5710495 | 13 | Human Placenta |
| chr4: 5891981-5892365 | 13 | Human Placenta |
| chr4: 5894071-5895116 | 13 | Human Placenta |
| chr4: 13524062-13526083 | 11 | Human Placenta |
| chr4: 15779998-15780729 | 9 | Human Placenta |
| chr4: 24801109-24801902 | 10 | Human Placenta |
| chr4: 41869174-41869459 | 12 | Human Placenta |
| chr4: 41875445-41875794 | 14 | Human Placenta |
| chr4: 41880224-41880500 | 13 | Human Placenta |
| chr4: 41882450-41882964 | 14 | Human Placenta |
| chr4: 46995128-46995872 | 14 | Human Placenta |
| chr4: 54975387-54976202 | 12 | Human Placenta |
| chr4: 57521621-57522703 | 8 | Human Placenta |
| chr4: 66535193-66535620 | 13 | Human Placenta |
| chr4: 81109887-81110460 | 13 | Human Placenta |
| chr4: 85403830-85404524 | 14 | Human Placenta |
| chr4: 85413997-85414874 | 11 | Human Placenta |
| chr4: 85422929-85423190 | 9 | Human Placenta |
| chr4: 93226348-93227007 | 10 | Human Placenta |
| chr4: 110222970-110224257 | 10 | Human Placenta |
| chr4: 111554965-111555504 | 13 | Human Placenta |
| chr4: 134069162-134070442 | 9 | Human Placenta |
| chr4: 140201064-140201449 | 8 | Human Placenta |
| chr4: 151504011-151505085 | 11 | Human Placenta |
| chr4: 154709512-154710827 | 10 | Human Placenta |
| chr4: 154712073-154712706 | 8 | Human Placenta |
| chr4: 154713537-154714240 | 11 | Human Placenta |
| chr4: 155663809-155664315 | 11 | Human Placenta |
| chr4: 156129168-156130209 | 11 | Human Placenta |
| chr4: 158143296-158144053 | 12 | Human Placenta |
| chr4: 169799086-169799625 | 9 | Human Placenta |
| chr4: 174422024-174422443 | 12 | Human Placenta |
| chr4: 174427891-174428192 | 11 | Human Placenta |
| chr4: 174437914-174438346 | 12 | Human Placenta |
| chr4: 174439812-174440249 | 13 | Human Placenta |
| chr4: 174448333-174448845 | 12 | Human Placenta |
| chr4: 174450046-174451469 | 11 | Human Placenta |
| chr4: 174451828-174452962 | 11 | Human Placenta |
| chr4: 174459200-174460054 | 8 | Human Placenta |
| chr4: 185937242-185937750 | 11 | Human Placenta |
| chr4: 187219320-187219745 | 8 | Human Placenta |

TABLE 1-continued

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
| --- | --- | --- |
| chr4: 188916605-188916876 | 14 | Human Placenta |
| chr4: 190938106-190938848 | 13 | Human Placenta |
| chr4: 190939801-190940591 | 12 | Human Placenta |
| chr5: 1874907-1879032 | 12 | Human Placenta |
| chr5: 2738953-2741237 | 10 | Human Placenta |
| chr5: 3590644-3592000 | 10 | Human Placenta |
| chr5: 3594467-3603054 | 12 | Human Placenta |
| chr5: 11384681-11385521 | 9 | Human Placenta |
| chr5: 31193952-31194419 | 8 | Human Placenta |
| chr5: 45695394-45696510 | 12 | Human Placenta |
| chr5: 50685453-50686148 | 13 | Human Placenta |
| chr5: 54519054-54519628 | 9 | Human Placenta |
| chr5: 63255044-63255407 | 13 | Human Placenta |
| chr5: 72526203-72526497 | 12 | Human Placenta |
| chr5: 72594147-72595808 | 9 | Human Placenta |
| chr5: 72676120-72678421 | 9 | Human Placenta |
| chr5: 76923887-76924502 | 15 | Human Placenta |
| chr5: 76936126-76936984 | 8 | Human Placenta |
| chr5: 77140542-77140914 | 13 | Human Placenta |
| chr5: 77146998-77147785 | 13 | Human Placenta |
| chr5: 77253832-77254049 | 13 | Human Placenta |
| chr5: 77268350-77268787 | 8 | Human Placenta |
| chr5: 87968635-87968907 | 13 | Human Placenta |
| chr5: 87980878-87981272 | 12 | Human Placenta |
| chr5: 87985470-87985810 | 11 | Human Placenta |
| chr5: 88185224-88185589 | 9 | Human Placenta |
| chr5: 115697134-115697589 | 8 | Human Placenta |
| chr5: 122430676-122431443 | 9 | Human Placenta |
| chr5: 134385967-134386370 | 13 | Human Placenta |
| chr5: 140346105-140346931 | 8 | Human Placenta |
| chr5: 140787447-140788044 | 14 | Human Placenta |
| chr5: 140864527-140864748 | 10 | Human Placenta |
| chr5: 146888750-146889840 | 8 | Human Placenta |
| chr5: 148033472-148034080 | 10 | Human Placenta |
| chr5: 158478378-158478630 | 8 | Human Placenta |
| chr5: 159399004-159399928 | 8 | Human Placenta |
| chr5: 170735169-170739863 | 10 | Human Placenta |
| chr5: 170741603-170742751 | 13 | Human Placenta |
| chr5: 170743178-170744107 | 11 | Human Placenta |
| chr5: 172110282-172111166 | 12 | Human Placenta |
| chr5: 172659049-172660277 | 13 | Human Placenta |
| chr5: 172660720-172661133 | 12 | Human Placenta |
| chr5: 172661486-172662228 | 9 | Human Placenta |
| chr5: 172672311-172672971 | 13 | Human Placenta |
| chr5: 174158680-174159729 | 11 | Human Placenta |
| chr5: 175085004-175085756 | 11 | Human Placenta |
| chr5: 178421225-178422337 | 14 | Human Placenta |
| chr5: 180486154-180486892 | 9 | Human Placenta |
| chr6: 1378445-1379318 | 12 | Human Placenta |
| chr6: 1393049-1394170 | 12 | Human Placenta |
| chr6: 1619093-1621094 | 9 | Human Placenta |
| chr6: 4079052-4079443 | 12 | Human Placenta |
| chr6: 5999149-5999787 | 10 | Human Placenta |
| chr6: 10381558-10382354 | 11 | Human Placenta |
| chr6: 10881846-10882051 | 14 | Human Placenta |
| chr6: 26614013-26614851 | 11 | Human Placenta |
| chr6: 27228100-27228364 | 13 | Human Placenta |
| chr6: 29595298-29595795 | 12 | Human Placenta |
| chr6: 30095173-30095610 | 14 | Human Placenta |
| chr6: 30139718-30140263 | 11 | Human Placenta |
| chr6: 33048416-33048814 | 12 | Human Placenta |
| chr6: 35479388-35479678 | 15 | Human Placenta |
| chr6: 37616722-37617179 | 15 | Human Placenta |
| chr6: 38682949-38683265 | 13 | Human Placenta |
| chr6: 41528266-41528900 | 10 | Human Placenta |
| chr6: 42145847-42146053 | 11 | Human Placenta |
| chr6: 42879279-42879623 | 14 | Human Placenta |
| chr6: 50787286-50788091 | 12 | Human Placenta |
| chr6: 50810642-50810994 | 13 | Human Placenta |
| chr6: 50813314-50813699 | 12 | Human Placenta |
| chr6: 50818180-50818431 | 12 | Human Placenta |
| chr6: 70992040-70992912 | 10 | Human Placenta |
| chr6: 72298274-72298528 | 11 | Human Placenta |
| chr6: 78172231-78174088 | 13 | Human Placenta |
| chr6: 85472702-85474132 | 11 | Human Placenta |
| chr6: 99290279-99290771 | 11 | Human Placenta |
| chr6: 100038655-100039477 | 9 | Human Placenta |
| chr6: 100897080-100897621 | 15 | Human Placenta |
| chr6: 100903491-100903713 | 11 | Human Placenta |
| chr6: 100905444-100905697 | 14 | Human Placenta |
| chr6: 100905952-100906686 | 12 | Human Placenta |
| chr6: 100914946-100915245 | 9 | Human Placenta |
| chr6: 106429111-106429772 | 15 | Human Placenta |
| chr6: 106433984-106434459 | 9 | Human Placenta |
| chr6: 108495654-108495986 | 14 | Human Placenta |
| chr6: 110299365-110301267 | 8 | Human Placenta |
| chr6: 117869097-117869530 | 8 | Human Placenta |
| chr6: 127441553-127441760 | 8 | Human Placenta |
| chr6: 137809342-137810204 | 13 | Human Placenta |
| chr6: 137816474-137817223 | 9 | Human Placenta |
| chr6: 150335525-150336278 | 12 | Human Placenta |
| chr6: 150358872-150359394 | 12 | Human Placenta |
| chr6: 154360586-154361008 | 10 | Human Placenta |
| chr6: 161188084-161188639 | 8 | Human Placenta |
| chr6: 166579973-166583423 | 12 | Human Placenta |
| chr6: 166666837-166667541 | 9 | Human Placenta |
| chr6: 168841438-168841699 | 8 | Human Placenta |
| chr6: 170732119-170732442 | 14 | Human Placenta |
| chr7: 751712-752150 | 13 | Human Placenta |
| chr7: 12151220-12151559 | 11 | Human Placenta |
| chr7: 19184818-19185033 | 14 | Human Placenta |
| chr7: 23287221-23287508 | 11 | Human Placenta |
| chr7: 27134097-27134303 | 9 | Human Placenta |
| chr7: 27147589-27148389 | 13 | Human Placenta |
| chr7: 27198182-27198514 | 9 | Human Placenta |
| chr7: 27203915-27206462 | 9 | Human Placenta |
| chr7: 27260101-27260467 | 10 | Human Placenta |
| chr7: 27291119-27292197 | 10 | Human Placenta |
| chr7: 32110063-32110910 | 13 | Human Placenta |
| chr7: 35296921-35298218 | 10 | Human Placenta |
| chr7: 42267546-42267823 | 10 | Human Placenta |
| chr7: 43152020-43153340 | 8 | Human Placenta |
| chr7: 53286851-53287192 | 10 | Human Placenta |
| chr7: 54612324-54612558 | 14 | Human Placenta |
| chr7: 70596228-70598382 | 12 | Human Placenta |
| chr7: 71800757-71802768 | 10 | Human Placenta |
| chr7: 72838383-72838815 | 11 | Human Placenta |
| chr7: 73894815-73895110 | 8 | Human Placenta |
| chr7: 89747892-89749036 | 9 | Human Placenta |
| chr7: 97361132-97363018 | 10 | Human Placenta |
| chr7: 100075303-100075551 | 8 | Human Placenta |
| chr7: 100817759-100817975 | 9 | Human Placenta |
| chr7: 100823307-100823701 | 11 | Human Placenta |
| chr7: 101005899-101007443 | 9 | Human Placenta |
| chr7: 103085710-103086132 | 10 | Human Placenta |
| chr7: 103968783-103969959 | 9 | Human Placenta |
| chr7: 121940006-121940648 | 14 | Human Placenta |
| chr7: 121950249-121950927 | 11 | Human Placenta |
| chr7: 121956543-121957341 | 11 | Human Placenta |
| chr7: 124404174-124404432 | 11 | Human Placenta |
| chr7: 127990926-127992616 | 11 | Human Placenta |
| chr7: 128555329-128556650 | 12 | Human Placenta |
| chr7: 129422997-129423355 | 12 | Human Placenta |
| chr7: 142494563-142495248 | 9 | Human Placenta |
| chr7: 143582125-143582610 | 10 | Human Placenta |
| chr7: 149389654-149389976 | 14 | Human Placenta |
| chr7: 149744402-149746469 | 13 | Human Placenta |
| chr7: 152621916-152622149 | 11 | Human Placenta |
| chr7: 153748407-153750444 | 14 | Human Placenta |
| chr7: 154001964-154002281 | 13 | Human Placenta |
| chr7: 155164557-155167854 | 11 | Human Placenta |
| chr7: 155174128-155175248 | 9 | Human Placenta |

TABLE 1-continued

Characterization of genomic location of the feature, the number of cancer types as reported in the disclosure in which they are specifically methylated, and one of two additional designations - their orthology to regions that are methylated during mouse development (Mouse ExE ortholog) or their specific methylation in human placenta and at least 8 of the 15 human cancer types examined.

| Human CGI (hg19) | # Cancers | Group |
|---|---|---|
| chr7: 155241323-155243757 | 11 | Human Placenta |
| chr7: 155258827-155261403 | 8 | Human Placenta |
| chr7: 155302253-155303158 | 8 | Human Placenta |
| chr7: 156409023-156409294 | 8 | Human Placenta |
| chr7: 156409577-156409865 | 9 | Human Placenta |
| chr7: 156801418-156801632 | 8 | Human Placenta |
| chr7: 156871054-156871297 | 11 | Human Placenta |
| chr7: 158936507-158938492 | 14 | Human Placenta |
| chr8: 4848968-4852635 | 8 | Human Placenta |
| chr8: 9760750-9761643 | 12 | Human Placenta |
| chr8: 9762661-9764748 | 12 | Human Placenta |
| chr8: 11536767-11538961 | 11 | Human Placenta |
| chr8: 11557852-11558252 | 12 | Human Placenta |
| chr8: 11565217-11567212 | 14 | Human Placenta |
| chr8: 21644908-21647845 | 9 | Human Placenta |
| chr8: 23562475-23565175 | 13 | Human Placenta |
| chr8: 23567180-23567678 | 14 | Human Placenta |
| chr8: 24812946-24814299 | 10 | Human Placenta |
| chr8: 26721642-26724566 | 11 | Human Placenta |
| chr8: 37822486-37824008 | 12 | Human Placenta |
| chr8: 41424341-41425300 | 12 | Human Placenta |
| chr8: 49468683-49468959 | 11 | Human Placenta |
| chr8: 50822270-50822860 | 12 | Human Placenta |
| chr8: 53851701-53854426 | 9 | Human Placenta |
| chr8: 55370170-55372525 | 13 | Human Placenta |
| chr8: 55378928-55380186 | 13 | Human Placenta |
| chr8: 57358126-57359415 | 14 | Human Placenta |
| chr8: 65281903-65283043 | 14 | Human Placenta |
| chr8: 65286067-65286659 | 9 | Human Placenta |
| chr8: 65290108-65290946 | 14 | Human Placenta |
| chr8: 68864584-68864946 | 10 | Human Placenta |
| chr8: 72468560-72469561 | 13 | Human Placenta |
| chr8: 85096759-85097247 | 13 | Human Placenta |
| chr8: 86350765-86351196 | 12 | Human Placenta |
| chr8: 87081653-87082046 | 10 | Human Placenta |
| chr8: 97169731-97170432 | 11 | Human Placenta |
| chr8: 97171805-97172022 | 14 | Human Placenta |
| chr8: 98289604-98290404 | 11 | Human Placenta |
| chr8: 99960497-99961438 | 11 | Human Placenta |
| chr8: 99984584-99985072 | 10 | Human Placenta |
| chr8: 99985733-99986983 | 14 | Human Placenta |
| chr8: 101117922-101118693 | 13 | Human Placenta |
| chr8: 130995921-130996149 | 12 | Human Placenta |
| chr8: 132052203-132054749 | 13 | Human Placenta |
| chr8: 139508795-139509774 | 12 | Human Placenta |
| chr8: 142528185-142529029 | 12 | Human Placenta |
| chr8: 145103285-145108027 | 12 | Human Placenta |
| chr8: 145925410-145926101 | 13 | Human Placenta |
| chr9: 969529-973276 | 12 | Human Placenta |
| chr9: 16726859-16727273 | 8 | Human Placenta |
| chr9: 19788215-19789288 | 12 | Human Placenta |
| chr9: 23820691-23822135 | 8 | Human Placenta |
| chr9: 23850910-23851522 | 12 | Human Placenta |
| chr9: 32782936-32783625 | 11 | Human Placenta |
| chr9: 36739534-36739782 | 14 | Human Placenta |
| chr9: 37002489-37002957 | 14 | Human Placenta |
| chr9: 77112712-77113583 | 9 | Human Placenta |
| chr9: 77113709-77113927 | 13 | Human Placenta |
| chr9: 79633326-79636030 | 9 | Human Placenta |
| chr9: 79637814-79638169 | 13 | Human Placenta |
| chr9: 91792662-91793611 | 10 | Human Placenta |
| chr9: 96108466-96108992 | 15 | Human Placenta |
| chr9: 96710811-96711717 | 13 | Human Placenta |
| chr9: 98111364-98112362 | 12 | Human Placenta |
| chr9: 100610696-100611517 | 12 | Human Placenta |
| chr9: 100619984-100620192 | 11 | Human Placenta |
| chr9: 104499849-104501076 | 8 | Human Placenta |
| chr9: 115822071-115823416 | 13 | Human Placenta |
| chr9: 120507227-120507642 | 9 | Human Placenta |
| chr9: 123656750-123656972 | 15 | Human Placenta |
| chr9: 134429866-134430491 | 10 | Human Placenta |
| chr9: 136294738-136295236 | 15 | Human Placenta |
| chr9: 137967110-137967727 | 10 | Human Placenta |
| chr9: 139715663-139716441 | 13 | Human Placenta |

REFERENCES

1. Smith, Z. D. & Meissner, A. DNA methylation: roles in mammalian development. Nat. Rev. Genet. 14, 204-220 (2013).
2. Ohm, J. E. et al. A stem cell-like chromatin pattern may predispose tumor suppressor genes to DNA hypermethylation and heritable silencing. Nat. Genet. 39, 237-242 (2007).
3. Schlesinger, Y. et al. Polycomb-mediated methylation on Lys27 of histone H3 premarks genes for de novo methylation in cancer. Nat. Genet. 39, 232-236 (2007).
4. Widschwendter, M. et al. Epigenetic stem cell signature in cancer. Nat. Genet. 39, 157-158 (2007).
5. Feinberg, A. P., Ohlsson, R. & Henikoff, S. The epigenetic progenitor origin of human cancer. Nat. Rev. Genet. 7, 21-33 (2006).
6. Flavahan, W. A., Gaskell, E. & Bernstein, B. E. Epigenetic plasticity and the hallmarks of cancer. Science 357, eaal2380 (2017).
7. Schroeder, D. I. et al. The human placenta methylome. Proc. Natl Acad. Sci. USA 110, 6037-6042 (2013).
8. Branco, M. R. et al. Maternal DNA methylation regulates early trophoblast development. Dev. Cell 36, 152-163 (2016).
9. Deaton, A. M. & Bird, A. CpG islands and the regulation of transcription. Genes Dev. 25, 1010-1022 (2011).
10. Arnold, S. J. & Robertson, E. J. Making a commitment: cell lineage allocation and axis patterning in the early mouse embryo. Nat. Rev. Mol. Cell Biol. 10, 91-103 (2009).
11. Hon, G. C. et al. Epigenetic memory at embryonic enhancers identified in DNA methylation maps from adult mouse tissues. Nat. Genet. 45, 1198-1206 (2013).
12. Ziller, M. J. et al. Charting a dynamic DNA methylation landscape of the human genome. Nature 500, 477-481 (2013).
13. Landan, G. et al. Epigenetic polymorphism and the stochastic formation of differentially methylated regions in normal and cancerous tissues. Nat. Genet. 44, 1207-1214 (2012).
14. Landau, D. A. et al. Locally disordered methylation forms the basis of intratumor methylome variation in chronic lymphocytic leukemia. Cancer Cell 26, 813-825 (2014).
15. Arman, E., Haffner-Krausz, R., Chen, Y., Heath, J. K. & Lonai, P. Targeted disruption of fibroblast growth factor (FGF) receptor 2 suggests a role for FGF signaling in pregastrulation mammalian development. Proc. Natl Acad. Sci. USA 95, 5082-5087 (1998).
16. Leitch, H. G. et al. Naive pluripotency is associated with global DNA hypomethylation. Nat. Struct. Mol. Biol. 20, 311-316 (2013).

17. Boulard, M., Edwards, J. R. & Bestor, T. H. Abnormal X chromosome inactivation and sex-specific gene dysregulation after ablation of FBXL10. *Epigenet. Chromatin* 9, 22 (2016).
18. Meissner, A. et al. Genome-scale DNA methylation maps of pluripotent and differentiated cells. *Nature* 454, 766-770 (2008).
19. The ENCODE Project Consortium. An integrated encyclopedia of DNA elements in the human genome. *Nature* 489, 57-74 (2012).
20. Hoadley, K. A. et al. Multiplatform analysis of 12 cancer types reveals molecular classification within and across tissues of origin. *Cell* 158, 929-944 (2014).
21. Kundaje, A. et al. Integrative analysis of 111 reference human epigenomes. *Nature* 518, 317-330 (2015).
22. MacLeod, A. R., Rouleau, J. & Szyf, M. Regulation of DNA methylation by the Ras signaling pathway. *J. Biol. Chem.* 270, 11327-11337 (1995).
23. Lu, C. W. et al. Ras-MAPK signaling promotes trophectoderm formation from embryonic stem cells and mouse embryos. *Nat. Genet.* 40, 921-926 (2008).
24. Serra, R. W., Fang, M., Park, S. M., Hutchinson, L. & Green, M. R. A KRAS-directed transcriptional silencing pathway that mediates the CpG island methylator phenotype. *eLife* 3, e02313 (2014).
25. Ley, T. J. et al. DNMT3A mutations in acute myeloid leukemia. *N. Engl. J. Med.* 363, 2424-2433 (2010).
26. Walter, M. J. et al. Recurrent DNMT3A mutations in patients with myelodysplastic syndromes. *Leukemia* 25, 1153-1158 (2011).
27. Rhee, I. et al. DNMT1 and DNMT3b cooperate to silence genes in human cancer cells. *Nature* 416, 552-556 (2002).
28. Lin, H. et al. Suppression of intestinal neoplasia by deletion of Dnmt3b. *Mol. Cell. Biol.* 26, 2976-2983 (2006).
29. Novakovic, B. & Saffery, R. Placental pseudo-malignancy from a DNA methylation perspective: unanswered questions and future directions. *Front. Genet.* 4, 285 (2013).
30. Hanahan, D. & Weinberg, R. A. Hallmarks of cancer: the next generation. *Cell* 144, 646-674 (2011).
31. Smith, Z. D. et al. DNA methylation dynamics of the human preimplantation embryo. *Nature* 511, 611-615 (2014).
32. Chenoweth, J. G. & Tesar, P. J. Isolation and maintenance of mouse epiblast stem cells. *Methods Mol. Biol.* 636, 25-44 (2010).
33. Smith, Z. D. et al. A unique regulatory phase of DNA methylation in the early mammalian embryo. *Nature* 484, 339-344 (2012).
34. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. *Nat. Methods* 10, 1213-1218 (2013).
35. Lara-Astiaso, D. et al. Immunogenetics. Chromatin state dynamics during blood formation. *Science* 345, 943-949 (2014).
36. Yoshida, N. & Perry, A. C. Piezo-actuated mouse intracytoplasmic sperm injection (ICSI). *Nat. Protocols* 2, 296-304 (2007).
37. Ying, Q. L. et al. The ground state of embryonic stem cell self-renewal. *Nature* 453, 519-523 (2008).
38. Ying, Q. L., Nichols, J., Chambers, I. & Smith, A. BMP induction of Id proteins suppresses differentiation and sustains embryonic stem cell self-renewal in collaboration with STAT3. *Cell* 115, 281-292 (2003).
39. Wang, H. et al. One-step generation of mice carrying mutations in multiple genes by CRISPR/Cas-mediated genome engineering. *Cell* 153, 910-918 (2013).
40. Labun, K., Montague, T. G., Gagnon, J. A., Thyme, S. B. & Valen, E. CHOPCHOP v2: a web tool for the next generation of CRISPR genome engineering. *Nucleic Acids Res.* 44, W272-W276 (2016).
41. Macaulay, I. C. et al. G&T-seq: parallel sequencing of single-cell genomes and transcriptomes. *Nat. Methods* 12, 519-522 (2015).
42. Picelli, S. et al. Full-length RNA-seq from single cells using Smart-seq2. *Nat. Protocols* 9, 171-181 (2014).
43. Gu, H. et al. Preparation of reduced representation bisulfite sequencing libraries for genome-scale DNA methylation profiling. *Nat. Protocols* 6, 468-481 (2011).
44. Wu, H. et al. Detection of differentially methylated regions from whole-genome bisulfite sequencing data without replicates. *Nucleic Acids Res.* 43, e141 (2015).
45. Ben-Porath, I. et al. An embryonic stem cell-like gene expression signature in poorly differentiated aggressive human tumors. *Nat. Genet.* 40, 499-507 (2008).
46. Raychaudhuri, S. et al. Identifying relationships among genomic disease regions: predicting genes at pathogenic SNP associations and rare deletions. *PLoS Genet.* 5, e1000534 (2009).
47. Schep, A. N. et al. Structured nucleosome fingerprints enable high-resolution mapping of chromatin architecture within regulatory regions. *Genome Res.* 25, 1757-1770 (2015).
48. Ciruna, B. G. & Rossant, J. Expression of the T-box gene Eomesodermin during early mouse development. *Mech. Dev.* 81, 199-203 (1999).
49. Ralston, A. & Rossant, J. Cdx2 acts downstream of cell polarization to cell-autonomously promote trophectoderm fate in the early mouse embryo. *Dev. Biol.* 313, 614-629 (2008).
50. Savory, J. G. et al. Cdx2 regulation of posterior development through non-Hox targets. *Development* 136, 4099-4110 (2009).
51. Donnison, M. et al. Loss of the extraembryonic ectoderm in Elf5 mutants leads to defects in embryonic patterning. *Development* 132, 2299-2308 (2005).
52. Goldin, S. N. & Papaioannou, V. E. Paracrine action of FGF4 during periimplantation development maintains trophectoderm and primitive endoderm. *Genesis* 36, 40-47 (2003).
53. Kang, M., Piliszek, A., Artus, J. & Hadjantonakis, A. K. FGF4 is required for lineage restriction and salt-and-pepper distribution of primitive endoderm factors but not their initial expression in the mouse. *Development* 140, 267-279 (2013).
54. Nichols, J., Silva, J., Roode, M. & Smith, A. Suppression of Erk signaling promotes ground state pluripotency in the mouse embryo. *Development* 136, 3215-3222 (2009).
55. Auclair, G., Guibert, S., Bender, A. & Weber, M. Ontogeny of CpG island methylation and specificity of DNMT3 methyltransferases during embryonic development in the mouse. *Genome Biol.* 15, 545 (2014).
56. Smallwood, S. A. et al. Dynamic CpG island methylation landscape in oocytes and preimplantation embryos. *Nat. Genet.* 43, 811-814 (2011).
57. Ooi, S. K. et al. DNMT3L connects unmethylated lysine 4 of histone H3 to de novo methylation of DNA. *Nature* 448, 714-717 (2007).

58. He, J. et al. Kdm2b maintains murine embryonic stem cell status by recruiting PRC1 complex to CpG islands of developmental genes. *Nat. Cell Biol.* 15, 373-384 (2013).
59. Wu, X., Johansen, J. V. & Helin, K. Fbxl10/Kdm2b recruits polycomb repressive complex 1 to CpG islands and regulates H2A ubiquitylation. *Mol. Cell* 49, 1134-1146 (2013).
60. Blackledge, N. P. et al. Variant PRC1 complex-dependent H2A ubiquitylation drives PRC2 recruitment and polycomb domain formation. *Cell* 157, 1445-1459 (2014).
61. Boulard, M., Edwards, J. R. & Bestor, T. H. FBXL10 protects Polycomb-bound genes from hypermethylation. *Nat. Genet.* 47, 479-485 (2015).
62. Irizarry, R. A. et al. The human colon cancer methylome shows similar hypo and hypermethylation at conserved tissue-specific CpG island shores. *Nat. Genet.* 41, 178-186 (2009).
63. Steine, E. J. et al. Genes methylated by DNA methyltransferase 3b are similar in mouse intestine and human colon cancer. *J. Clin. Invest.* 121, 1748-1752 (2011).
64. Schulze, I. et al. Increased DNA methylation of Dnmt3b targets impairs leukemogenesis. *Blood* 127, 1575-1586 (2016).
65. Yang, L. et al. DNMT3A loss drives enhancer hypomethylation in FLT3-ITDassociated leukemias. *Cancer Cell* 29, 922-934 (2016); erratum 30, 363-365, (2016).
66. Mayle, A. et al. Dnmt3a loss predisposes murine hematopoietic stem cells to malignant transformation. *Blood* 125, 629-638 (2015).
67. Haney, S. L. et al. Promoter hypomethylation and expression is conserved in mouse chronic lymphocytic leukemia induced by decreased or inactivated Dnmt3a. *Cell Rep.* 15, 1190-1201 (2016).

What is claimed is:

1. A method of treating cancer in an individual, comprising:
   obtaining DNA methylation sequence reads for at least one CpG Island (CGI) from a sample from the individual;
   calculating the proportion of concordantly methylated reads (PMR) for the at least one CGI;
   comparing the PMR of the at least one CGI to a PMR of a control background of a normal tissue or epiblast, wherein the PMR of the sample is larger than the PMR of the control background thereby indicating the presence of cancer in the individual; and
   treating the cancer in the individual with a chemotherapeutic drug, surgery, or radiotherapy.

2. A method of treating cancer in an individual, comprising:
   treating the cancer in the individual with a chemotherapeutic drug, surgery, or radiotherapy, wherein the individual has been previously identified as having cancer by a method comprising:
   obtaining DNA methylation sequence reads for at least one CpG Island (CGI) from a sample from the individual;
   calculating the proportion of concordantly methylated reads (PMR) for the at least one CGI; and
   comparing the PMR of the at least one CGI to a PMR of a control background of a normal tissue or epiblast, wherein cancer is detected when the PMR of the sample is larger than the PMR of the control background.

3. The method of claim 1, wherein the cancer is selected from the group consisting of bladder urothelial carcinoma, breast invasive carcinoma, colon adenocarcinoma, colorectal adenocarcinoma, head and neck squamous cell carcinoma, kidney renal clear cell carcinoma, kidney renal papillary cell carcinoma, liver hepatocellular carcinoma, lung adenocarcinoma, lung squamous cell carcinoma, prostate adenocarcinoma, stomach and oesophageal carcinoma, thyroid carcinoma, uterine corpus endometrial carcinoma, and chronic lymphocytic leukaemia.

4. The method of claim 1, wherein the sample is selected from the group consisting of plasma, urine, stool, menstrual fluid, and lymph fluid.

5. The method of claim 1, wherein the presence of cancer is detected in the sample with a sensitivity of greater than 80%.

6. The method of claim 1, wherein the presence of cancer is detected in the sample with a sensitivity of greater than 75%.

7. The method of claim 1, wherein the presence of cancer is detected in the sample with about 100% sensitivity and about 95% specificity.

8. The method of claim 1, wherein the sample has been processed by the steps of:
   obtaining cell free DNA from the sample;
   treating the cell free DNA with bisulfite;
   amplifying at least one CpG island (CGI) from the bisulfite-treated DNA; and
   sequencing the amplified DNA using next-generation sequencing (NGS) to generate a dataset comprising a plurality of sequencing reads for the at least one CGI.

9. The method of claim 1, wherein the sample is a first sample obtained prior to the individual receiving a cancer treatment, and the method further comprises:
   using the calculated PMR of the first sample to detect an amount of circulating tumor DNA (ctDNA) in the first sample;
   obtaining DNA methylation sequence reads for the same at least one CGI from a second sample obtained after the same individual received a cancer treatment;
   calculating the PMR for the same at least one CGI from the second sample, and using the calculated PMR for the second sample to detect an amount of ctDNA in the second sample;

comparing the amount of ctDNA obtained from the first sample and the amount of ctDNA obtained from the second sample, wherein an increase in ctDNA is indicative of a subject's negative response to cancer treatment and a decrease in ctDNA is indicative of a subject's positive response to the cancer treatment.

10. The method of claim 2, wherein the cancer is selected from the group consisting of bladder urothelial carcinoma, breast invasive carcinoma, colon adenocarcinoma, colorectal adenocarcinoma, head and neck squamous cell carcinoma, kidney rental clear cell carcinoma, kidney renal papillary cell carcinoma, liver hepatocellular carcinoma, lung adenocarcinoma, lung squamous cell carcinoma, prostate adenocarcinoma, stomach and oesophageal carcinoma, thyroid carcinoma, uterine corpus endometrial carcinoma, and chronic lymphocytic leukaemia.

11. The method of claim 2, wherein the sample is selected from the group consisting of plasma, urine, stool, menstrual fluid, and lymph fluid.

12. The method of claim 2, wherein the presence of cancer is detected in the sample with a sensitivity of greater than 80%.

13. The method of claim 2, wherein the presence of cancer is detected in the sample with a sensitivity of greater than 75%.

14. The method of claim 2, wherein the presence of cancer is detected in the sample with about 100% sensitivity and about 95% specificity.

15. The method of claim 2, wherein the sample has been processed by the steps of:
obtaining cell free DNA from the sample;
treating the cell free DNA with bisulfite;
amplifying at least one CpG island (CGI) from the bisulfite-treated DNA; and
sequencing the amplified DNA using next-generation sequencing (NGS) to generate a dataset comprising a plurality of sequencing reads for the at least one CGI.

16. The method of claim 2, wherein the sample is a first sample obtained prior to the individual receiving a cancer treatment, and the method further comprises:
using the calculated PMR of the first sample to detect an amount of circulating tumor DNA (ctDNA) in the first sample;
obtaining DNA methylation sequence reads for the same at least one CGI from a second sample obtained after the same individual received a cancer treatment;
calculating the PMR for the same at least one CGI from the second sample, and using the calculated PMR for the second sample to detect an amount of ctDNA in the second sample;
comparing the amount of ctDNA obtained from the first sample and the amount of ctDNA obtained from the second sample, wherein an increase in ctDNA is indicative of a subject's negative response to cancer treatment and a decrease in ctDNA is indicative of a subject's positive response to the cancer treatment.

* * * * *

SEQUENCE LISTING

```
<160> NUMBER OF SEQ ID NOS: 20

<210> SEQ ID NO 1
<211> LENGTH: 49
<212> TYPE: DNA
<213> ORGANISM: Artificial
<220> FEATURE:
<223> OTHER INFORMATION: forward primer
<220> FEATURE:
<221> NAME/KEY: misc_feature
<222> LOCATION: (26)..(26)
<223> OTHER INFORMATION: n is a, c, g, or t

<400> SEQUENCE: 1
agtcagttaa tacgactcac tatagngttt tagagctaga aatagcaag          49

<210> SEQ ID NO 2
<211> LENGTH: 25
<212> TYPE: DNA
<213> ORGANISM: Artificial
<220> FEATURE:
<223> OTHER INFORMATION: reverse primer

<400> SEQUENCE: 2
aaaaaaagca ccgactcggt gccac                                    25

<210> SEQ ID NO 3
<211> LENGTH: 20
<212> TYPE: DNA
<213> ORGANISM: Artificial
<220> FEATURE:
<223> OTHER INFORMATION: sgRNA sequence

<400> SEQUENCE: 3
gaaactggaa gaggtaacag                                          20

<210> SEQ ID NO 4
<211> LENGTH: 20
<212> TYPE: DNA
<213> ORGANISM: Artificial
<220> FEATURE:
<223> OTHER INFORMATION: sgRNA sequence

<400> SEQUENCE: 4
gactcccgag gacagagacg                                          20

<210> SEQ ID NO 5
<211> LENGTH: 20
```

```
<212> TYPE: DNA
<213> ORGANISM: Artificial
<220> FEATURE:
<223> OTHER INFORMATION: sgRNA sequence

<400> SEQUENCE: 5
agtatcaaac caggtcgagg                                                   20

<210> SEQ ID NO 6
<211> LENGTH: 20
<212> TYPE: DNA
<213> ORGANISM: Artificial
<220> FEATURE:
<223> OTHER INFORMATION: sgRNA sequence

<400> SEQUENCE: 6
gccagtagga ggggatgctg                                                   20

<210> SEQ ID NO 7
<211> LENGTH: 20
<212> TYPE: DNA
<213> ORGANISM: Artificial
<220> FEATURE:
<223> OTHER INFORMATION: sgRNA sequence

<400> SEQUENCE: 7
ggcattggag agctggtgtg                                                   20

<210> SEQ ID NO 8
<211> LENGTH: 20
<212> TYPE: DNA
<213> ORGANISM: Artificial
<220> FEATURE:
<223> OTHER INFORMATION: sgRNA sequence

<400> SEQUENCE: 8
gcttgttgta ggtggcctgg                                                   20

<210> SEQ ID NO 9
<211> LENGTH: 20
<212> TYPE: DNA
<213> ORGANISM: Artificial
<220> FEATURE:
<223> OTHER INFORMATION: sgRNA sequence

<400> SEQUENCE: 9
agagggtgcc agcgggtatg                                                   20

<210> SEQ ID NO 10
<211> LENGTH: 20
<212> TYPE: DNA
<213> ORGANISM: Artificial
<220> FEATURE:
<223> OTHER INFORMATION: sgRNA sequence

<400> SEQUENCE: 10
gcctccccca gaatcacccg                                                   20

<210> SEQ ID NO 11
<211> LENGTH: 20
<212> TYPE: DNA
<213> ORGANISM: Artificial
<220> FEATURE:
<223> OTHER INFORMATION: sgRNA sequence

<400> SEQUENCE: 11
```

```
ggataggtg acctcgtgtg                                        20

<210> SEQ ID NO 12
<211> LENGTH: 20
<212> TYPE: DNA
<213> ORGANISM: Artificial
<220> FEATURE:
<223> OTHER INFORMATION: sgRNA sequence

<400> SEQUENCE: 12
gcctgtcgga ggcgaggagg                                       20

<210> SEQ ID NO 13
<211> LENGTH: 20
<212> TYPE: DNA
<213> ORGANISM: Artificial
<220> FEATURE:
<223> OTHER INFORMATION: sgRNA sequence

<400> SEQUENCE: 13
tgcaccatct gctgttccgg                                       20

<210> SEQ ID NO 14
<211> LENGTH: 20
<212> TYPE: DNA
<213> ORGANISM: Artificial
<220> FEATURE:
<223> OTHER INFORMATION: sgRNA sequence

<400> SEQUENCE: 14
cggcacccct tgtttgaggg                                       20

<210> SEQ ID NO 15
<211> LENGTH: 20
<212> TYPE: DNA
<213> ORGANISM: Artificial
<220> FEATURE:
<223> OTHER INFORMATION: sgRNA sequence

<400> SEQUENCE: 15
gatgctgtca gtattgagag                                       20

<210> SEQ ID NO 16
<211> LENGTH: 20
<212> TYPE: DNA
<213> ORGANISM: Artificial
<220> FEATURE:
<223> OTHER INFORMATION: sgRNA sequence

<400> SEQUENCE: 16
gatccagcaa ctgctaatag                                       20

<210> SEQ ID NO 17
<211> LENGTH: 20
<212> TYPE: DNA
<213> ORGANISM: Artificial
<220> FEATURE:
<223> OTHER INFORMATION: sgRNA sequence

<400> SEQUENCE: 17
gaaggtttgg gtctcgtggg                                       20

<210> SEQ ID NO 18
<211> LENGTH: 20
<212> TYPE: DNA
<213> ORGANISM: Artificial
```

```
<220> FEATURE:
<223> OTHER INFORMATION: sgRNA sequence

<400> SEQUENCE: 18
tgaagcagag ctgcatcatg                                                      20

<210> SEQ ID NO 19
<211> LENGTH: 20
<212> TYPE: DNA
<213> ORGANISM: Artificial
<220> FEATURE:
<223> OTHER INFORMATION: sgRNA sequence

<400> SEQUENCE: 19
gcctgcctgc ggacggagtg                                                      20

<210> SEQ ID NO 20
<211> LENGTH: 20
<212> TYPE: DNA
<213> ORGANISM: Artificial
<220> FEATURE:
<223> OTHER INFORMATION: sgRNA sequence

<400> SEQUENCE: 20
ggcagccaac ttcaccgctg                                                      20
```